United States Patent
Mehal et al.

(10) Patent No.: US 10,624,917 B2
(45) Date of Patent: Apr. 21, 2020

(54) COMPOSITIONS AND METHODS USEFUL FOR TREATING OR PREVENTING LIVER DISEASES OR DISORDERS, AND PROMOTING WEIGHT LOSS

(71) Applicant: YALE UNIVERSITY, New Haven, CT (US)

(72) Inventors: Wajahat Mehal, Guilford, CT (US); Xinshou Ouyang, West Hartford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/503,611

(22) PCT Filed: Aug. 18, 2015

(86) PCT No.: PCT/US2015/045653
§ 371 (c)(1),
(2) Date: Feb. 13, 2017

(87) PCT Pub. No.: WO2016/028753
PCT Pub. Date: Feb. 25, 2016

(65) Prior Publication Data
US 2017/0232027 A1   Aug. 17, 2017

Related U.S. Application Data

(60) Provisional application No. 62/039,619, filed on Aug. 20, 2014.

(51) Int. Cl.
*A61K 31/7048* (2006.01)
*A61K 45/06* (2006.01)
*A61K 31/575* (2006.01)

(52) U.S. Cl.
CPC ........ *A61K 31/7048* (2013.01); *A61K 31/575* (2013.01); *A61K 45/06* (2013.01)

(58) Field of Classification Search
CPC .. A61K 31/7048; A61K 45/06; A61K 31/575; A61K 2300/00
USPC .......................................................... 514/26
See application file for complete search history.

(56) References Cited

U.S. PATENT DOCUMENTS

| | | | |
|---|---|---|---|
| 5,545,623 | A | 8/1996 | Matsumori |
| 8,569,248 | B2 | 10/2013 | Pollard |
| 2008/0194575 | A1 | 8/2008 | Beraza et al. |
| 2009/0297496 | A1 | 12/2009 | Grabowski |
| 2011/0182912 | A1 | 7/2011 | Evans et al. |
| 2014/0011755 | A1 | 1/2014 | Stein et al. |
| 2014/0066392 | A1 | 3/2014 | Morrison et al. |

OTHER PUBLICATIONS

Rabadia et al. Hepaptoprotective Activity of Aqueous Extract of Digitalis purpurea in Carbon Tetra Chloride Induced Hepatotoxicity in Albino Rats. Asian Journal of Biomedical and Pharmaceutical Sciences; 4(34):64-71, 2014. Published on: Aug. 1, 2014. (Year: 2014).*
Hannerz J. Decrease of Intracranial Pressure and Weight with Digoxin in Obesity. Journal of Clinical Pharmacology, 2001;41:465-468. (Year: 2001).*
Uges D. Plasma or serum in therapeutic drug monitoring and clinical toxicology. Pharm Weekbl [Sci] 1988; 10:185-188. (Year: 1988).*
Supplemental Partial European Search Report for European Patent Application No. 15833246.0 dated Apr. 4, 2018.
Ahmed, et al.,"Digoxin and reduction in mortality and hospitalization in geriatric heart failure: importance of low doses and low serum concentrations," J Gerontol A Biol Sci Med Sci. 62(3) ,2007 ,323-329.
Cui, et al.,"Anti-hepatitis B virus activities of cinobufacini and its active components bufalin and cinobufagin in HepG2.2.15 cells," Biol Pharm Bull. 33(10) ,2010 ,1728-1732.
Guillot, et al.,"Cannabinoid receptor 2 counteracts interleukin-17-induced immune and fibrogenic responses in mouse liver," Hepatology. 59(1) ,2014 ,296-306.
Nath, et al.,"Hepatocyte-specific hypoxia-inducible factor-1α is a determinant of lipid accumulation and liver injury in alcohol-induced steatosis in mice," Hepatology. 53(5) ,2011 ,1526-1537.
Oselkin, et al.,"Low-dose cardiotonic steroids increase sodium-potassium ATPase activity that protects hippocampal slice cultures from experimental ischemia," Neurosci Lett. 473(2) ,2010 ,67-71.
Ouyang, et al.,"Adenosine is required for sustained inflammasome activation via the $A_2A$ receptor and the HIF-1α pathway," Nat Commun. 4 ,2013 ,2909.
Ouyang, et al.,"An adenosine A2a receptor/HIF-1 alpha axis Sunstains Inflammasome Activation Resulting in Liver Injury and Fibrosis That Can Be Blocked by Digoxin," Hepatology, 58, Suppl. 1 , 2013 , 338A-339A.
Ouyang, et al.,"Low dose digoxin protects from NASH and alcoholic hepatitis in mice by inhibiting a ROS-HIF-1 alpha Inflammasome pathway," Hepatology, 60, suppl. 1 ,2014 ,518A.
Zhang, et al.,"Digoxin and other cardiac glycosides inhibit HIF-1alpha synthesis and block tumor growth," Proc Natl Acad Sci U S A. 105(50) ,2008 ,19579-19586.
International Search Report and Written Opinion for PCT International Application No. PCT/US2015/045653 dated Nov. 10, 2015.
Baas, "Cardiac glycosides: a leap to lupus?", SciBX 3(46), 2010, 1-2.
Prassas, et al., "Novel therapeutic applications of cardiac glycosides", Nat Rev Drug Discov. 7(11), 2008, 926-935.

(Continued)

*Primary Examiner* — Yih-Horng Shiao
(74) *Attorney, Agent, or Firm* — Saul Ewing Arnstein & Lehr LLP; Kathryn Doyle; Domingos J. Silva

(57) ABSTRACT

The invention includes a method of preventing or treating a toxic liver disease or disorder, such as but not limited to non-alcoholic steatohepatitis (NASH), liver injury associated with or caused by alcohol consumption in a mammal afflicted with NASH, alcoholic hepatitis, drug induced liver injury, primary sclerosing cholangitis, viral hepatitis, liver fibrosis, liver cirrhosis, and other toxic liver conditions, in a subject, such as a mammal. The invention also includes a method of promoting weight loss in a subject, such as a mammal. The invention comprises administering to the subject a therapeutically effective dose of at least one cardiac glycoside or a solvate, salt, prodrug or derivative thereof.

12 Claims, 43 Drawing Sheets

Specification includes a Sequence Listing.

(56) References Cited

OTHER PUBLICATIONS

"AASLD Abstracts", Hepatology. 58(4) Suppl., 2013, 336A-339A.
Zilly, et al., "Pharmacokinetics of digoxin and methyldigoxin in patients with acute hepatitis", Med Klin. 73(13), 1978, 463-469 (Abstract Only).
Zimmermann, et al., "Interleukin-8 is activated in patients with chronic liver diseases and associated with hepatic macrophage accumulation in human liver fibrosis", PLoS One. 6(6), 2011, e21381.
Extended European Search Report for European Patent Application No. 15833246.0, dated Jul. 27, 2018.
Bai, et al.,"A comparison of the effects of digoxin, ouabain and milrinone on naloxone-precipitated withdrawal syndrome in mice", Eur J Pharmacol. 694(1-3), Nov. 2012, 69-74.
Hannerz, et al.,"Decrease of intracranial pressure and weight with digoxin in obesity", J Clin Pharmacol. 41(4), Apr. 2001, 465-468.
Shin, et al.,"Metabolic consequences of high-fat diet are attenuated by suppression of HIF-1$\alpha$", PLoS One. 7(10), Oct. 2012, e46562.
Zhang, et al.,"Bufotalin from Venenum Bufonis inhibits growth of multidrug resistant HepG2 cells through G2/M cell cycle arrest and apoptosis", Eur J Pharmacol. 692(1-3), Oct. 2012, 19-28.

\* cited by examiner

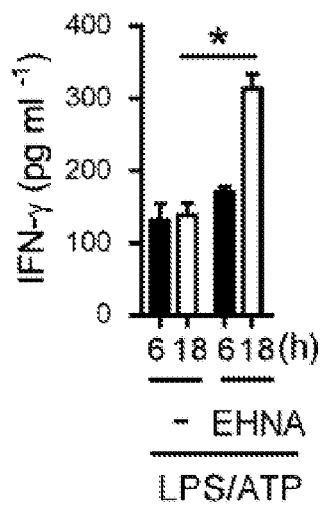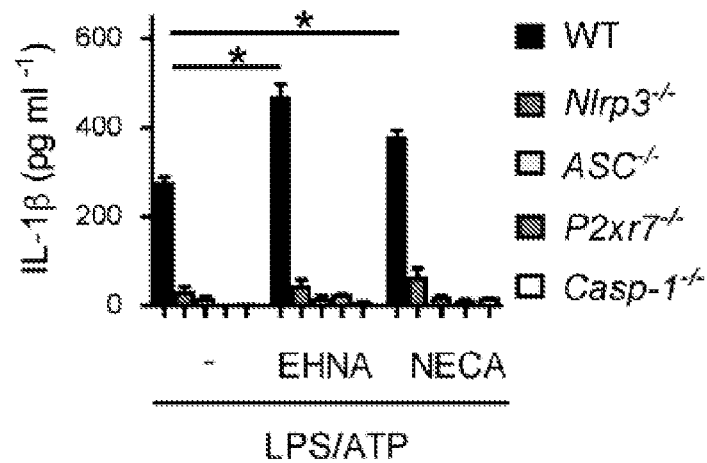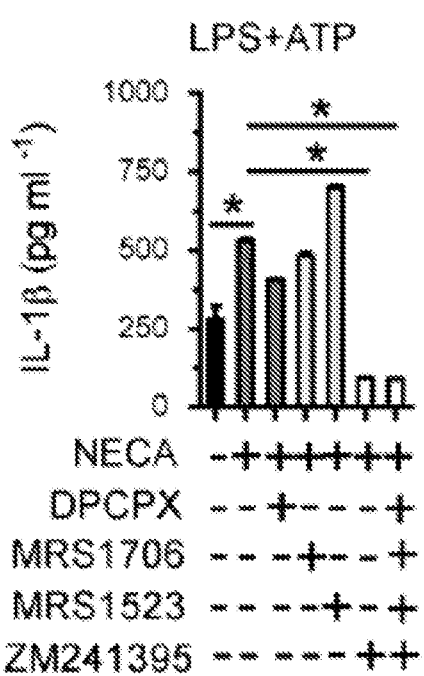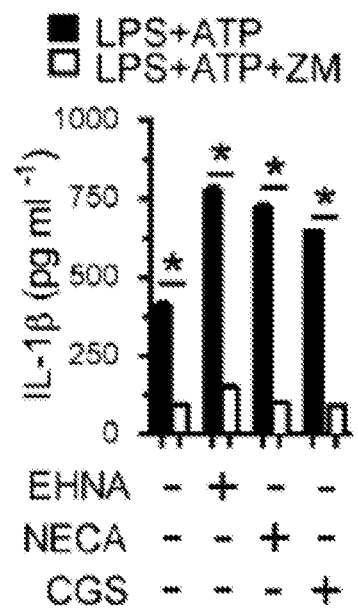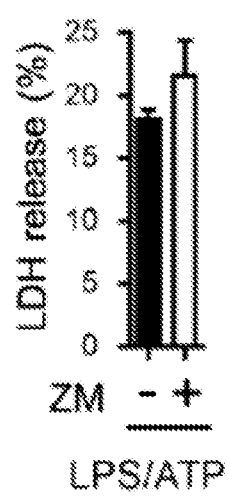

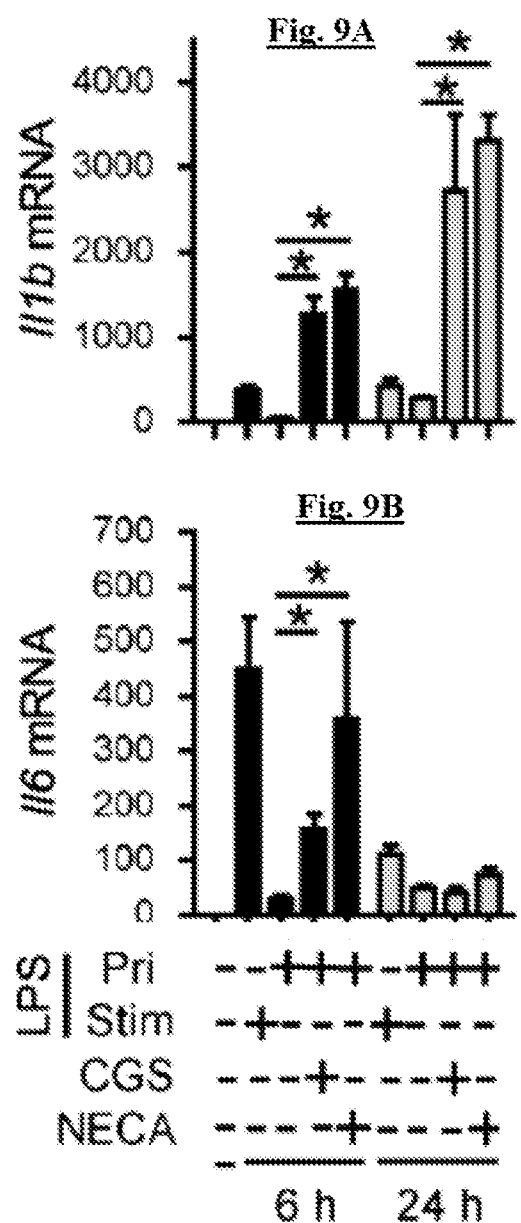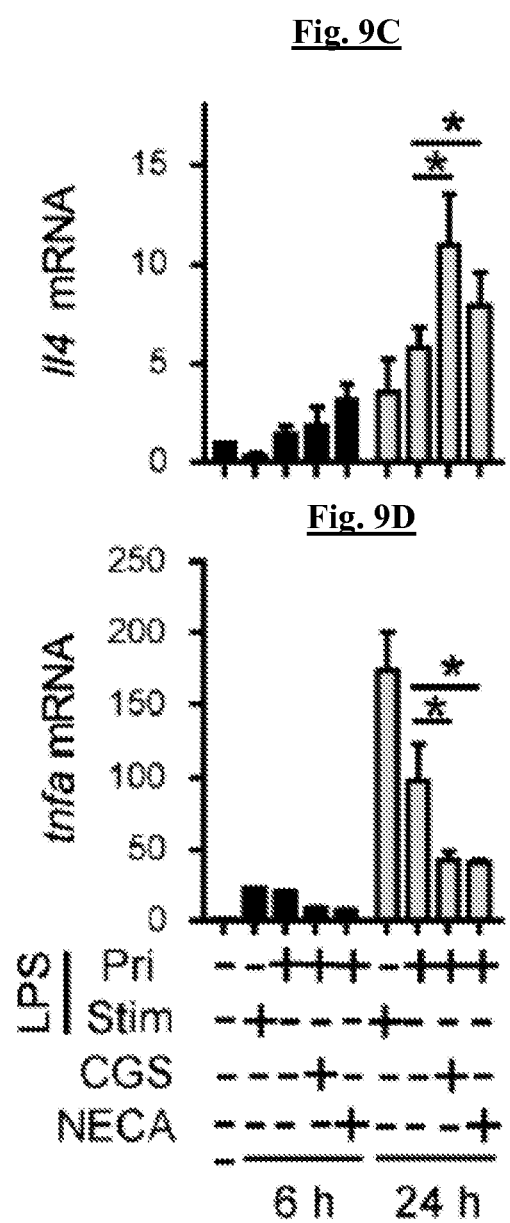

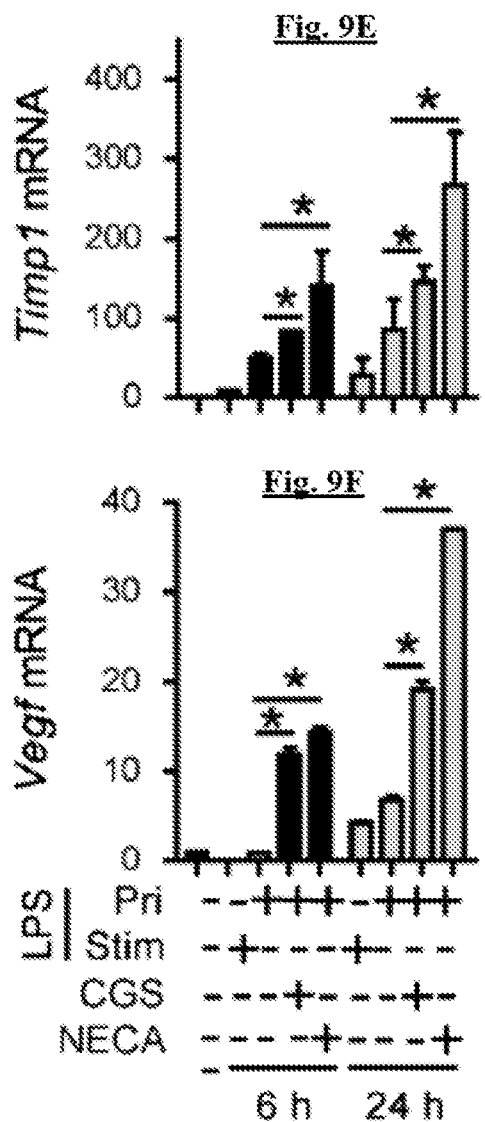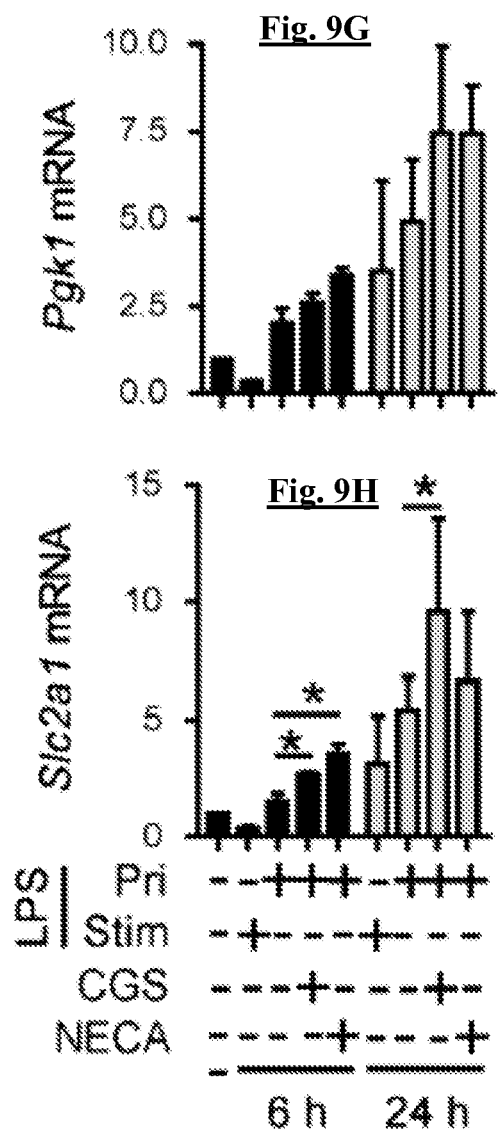

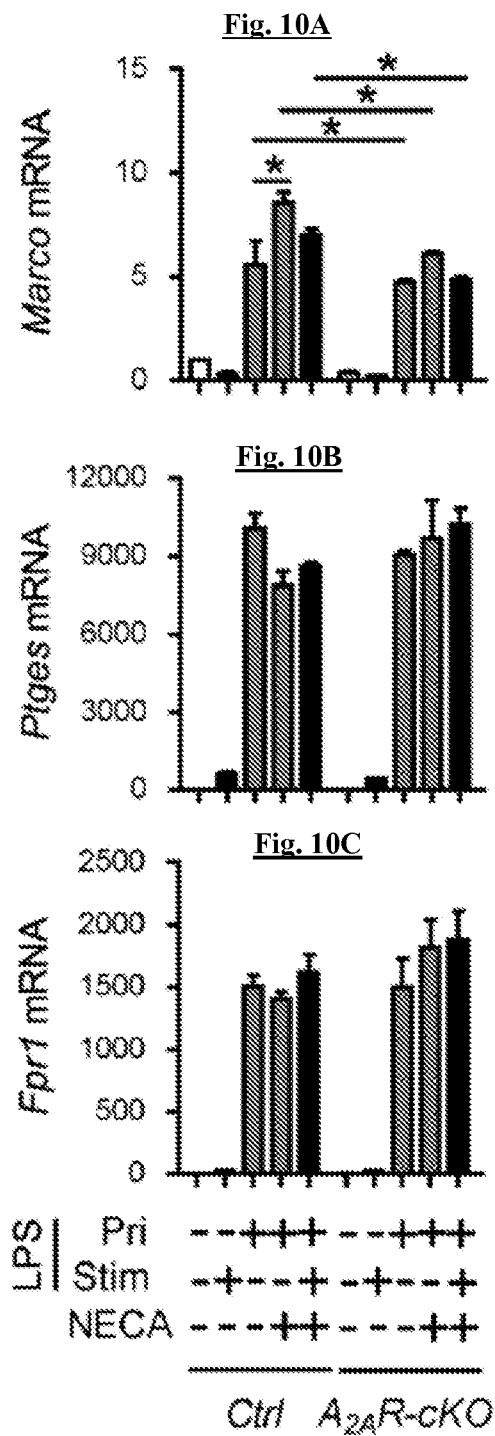

concurrent; plot on $\log_{10}$ scale concurrent; plot on $\log_{10}$ scale

Post-HFD

Fig. 25A
LPS/D-GalN
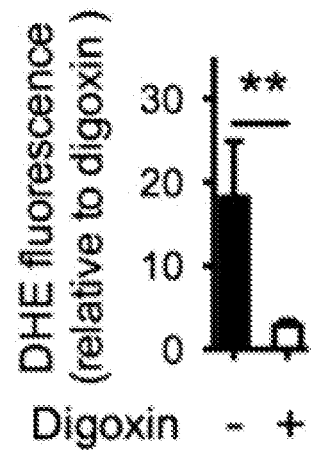
Digoxin  − +
LPS/D-GalN  + +
Fig. 25B
HFD
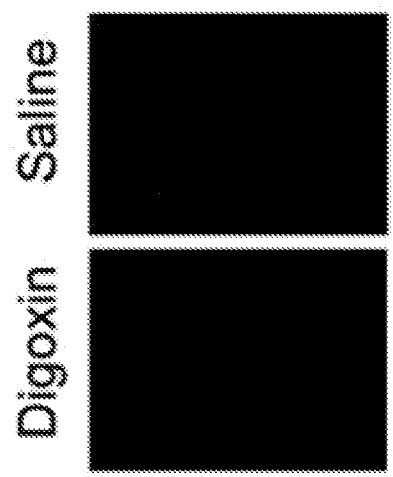
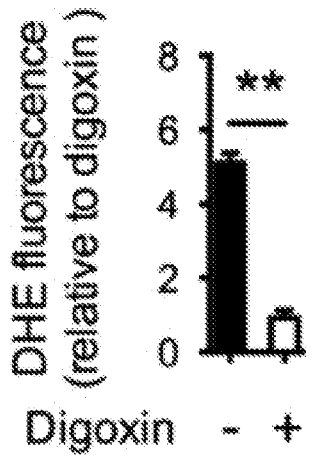
Digoxin  − +
HFD  + +

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: chemically synthesized

<400> SEQUENCE: 1
```
aaatggcctc cctctcat                                          18

<210> SEQ ID NO 2
<211> LENGTH: 18
<212> TYPE: DNA
<213> ORGANISM: Artificial Sequence
<220> FEATURE:
<223> OTHER INFORMATION: chemically synthesized

<400> SEQUENCE: 2
cctccacttg gtggtttg                                          18

<210> SEQ ID NO 3
<211> LENGTH: 20
<212> TYPE: DNA
<213> ORGANISM: Artificial Sequence
<220> FEATURE:
<223> OTHER INFORMATION: chemically synthesized

<400> SEQUENCE: 3
tgcaggagga agactttgtg                                        20

<210> SEQ ID NO 4
<211> LENGTH: 20
<212> TYPE: DNA
<213> ORGANISM: Artificial Sequence
<220> FEATURE:
<223> OTHER INFORMATION: chemically synthesized

<400> SEQUENCE: 4
cacgtggtcc attctggtag                                        20

<210> SEQ ID NO 5
<211> LENGTH: 18
<212> TYPE: DNA
<213> ORGANISM: Artificial Sequence
<220> FEATURE:
<223> OTHER INFORMATION: chemically synthesized

<400> SEQUENCE: 5
ccaggccttg acaagcta                                          18

<210> SEQ ID NO 6
<211> LENGTH: 18
<212> TYPE: DNA
<213> ORGANISM: Artificial Sequence
<220> FEATURE:
<223> OTHER INFORMATION: chemically synthesized

<400> SEQUENCE: 6
cgcggagaaa gagacaag                                          18

<210> SEQ ID NO 7
<211> LENGTH: 20
<212> TYPE: DNA
<213> ORGANISM: Artificial Sequence
<220> FEATURE:
<223> OTHER INFORMATION: chemically synthesized

<400> SEQUENCE: 7
tgcaagagac ttccatccag                                        20

<210> SEQ ID NO 8
<211> LENGTH: 20
<212> TYPE: DNA

```
<213> ORGANISM: Artificial Sequence
<220> FEATURE:
<223> OTHER INFORMATION: chemically synthesized

<400> SEQUENCE: 8
tgaagtctcc tctccggact                                                   20

<210> SEQ ID NO 9
<211> LENGTH: 19
<212> TYPE: DNA
<213> ORGANISM: Artificial Sequence
<220> FEATURE:
<223> OTHER INFORMATION: chemically synthesized

<400> SEQUENCE: 9
caagagcctc agagtgcag                                                    19

<210> SEQ ID NO 10
<211> LENGTH: 19
<212> TYPE: DNA
<213> ORGANISM: Artificial Sequence
<220> FEATURE:
<223> OTHER INFORMATION: chemically synthesized

<400> SEQUENCE: 10
ccagggacac tgacgtaga                                                    19

<210> SEQ ID NO 11
<211> LENGTH: 20
<212> TYPE: DNA
<213> ORGANISM: Artificial Sequence
<220> FEATURE:
<223> OTHER INFORMATION: chemically synthesized

<400> SEQUENCE: 11
agtaaggcct gtagctgtgc                                                   20

<210> SEQ ID NO 12
<211> LENGTH: 20
<212> TYPE: DNA
<213> ORGANISM: Artificial Sequence
<220> FEATURE:
<223> OTHER INFORMATION: chemically synthesized

<400> SEQUENCE: 12
cgctggtata aggtggtctc                                                   20
```

COMPOSITIONS AND METHODS USEFUL FOR TREATING OR PREVENTING LIVER DISEASES OR DISORDERS, AND PROMOTING WEIGHT LOSS

CROSS-REFERENCE TO RELATED APPLICATIONS

This application is a 35 U.S.C. § 371 national phase application from, and claims priority to, International Application No. PCT/US2015/045653, filed Aug. 18, 2015, and published under PCT Article 21(2) in English, which claims priority under 35 U.S.C. § 119(e) to U.S. Provisional Application No. 62/039,619, filed Aug. 20, 2014, all of which applications are hereby incorporated by reference in their entireties.

STATEMENT REGARDING FEDERALLY SPONSORED RESEARCH OR DEVELOPMENT

This invention was made with government support under grant number DK076674 and AA021912 awarded by National Institutes of Health. The government has certain rights in the invention.

BACKGROUND OF THE INVENTION

Steatohepatitis (also known as fatty liver disease) is a type of liver disease, characterized by liver inflammation with concurrent fat accumulation in the liver. Classically seen in alcoholics as part of alcoholic liver disease, steatohepatitis is also frequently found in people with diabetes and obesity and is related to metabolic syndrome.

When not associated with excessive alcohol intake, it is referred to as non-alcoholic steatohepatitis (also known as "NASH"), and is the progressive form of the relatively benign non-alcoholic fatty liver disease. Steatohepatitis of either etiology may progress to cirrhosis, and NASH is now believed to be a frequent cause of unexplained cirrhosis. NASH is also associated with lysosomal acid lipase deficiency.

Steatohepatitis is characterized microscopically by hepatic fat accumulation (steatosis), mixed lobular inflammation, ballooning degeneration of hepatocytes (sometimes with identifiable Mallory bodies), glycogenated hepatocyte nuclei, and pericellular fibrosis. The "chicken wire" pattern of the pericellular fibrosis, which affects portal areas only secondarily in later stages, is very characteristic and is identified on trichrome stains.

NASH is commonly associated with metabolic syndrome (obesity, dyslipidemia and insulin resistance). Further progression of the disease is probably caused by chronic inflammation and reactive oxygen species formation. Metabolically induced liver inflammation recruits additional inflammatory components (neutrophils, AP-1 pathway) and causes NASH. A retrospective cohort study concluded that liver failure is the main cause of morbidity and mortality in NASH-associated cirrhosis. No treatment has yet emerged as the "gold standard" for NASH.

Digoxin is a purified cardiac glycoside similar to digitoxin extracted from the foxglove plant, *Digitalis lanata*. Digoxin is widely used in the treatment of various heart conditions, namely atrial fibrillation, atrial flutter and sometimes heart failure that cannot be controlled by other medication. In such diseases, high ventricular rate leads to insufficient diastolic filling time. By slowing down the conduction in the atrioventricular (AV) node and increasing its refractory period, digoxin can reduce the ventricular rate. The arrhythmia itself is not affected, but the pumping function of the heart improves owing to improved filling.

Digoxin is a cardiac glycoside that acts as an inotropic agent; it decreases the action of the $Na^+/K^+$ ATPase channel by binding to an allosteric site. Normally $3 \times Na^+$ move out of the cardiac cell, and $2 \times K^+$ move into the cardiac cell. As a result, $Na^+$ concentration in myocyte increases and inactivates the NCX antiporter protein, wherein $Na^+$ is no longer be pumped into the myocyte. On the other hand, inactivation of NCX causes $Ca^{2+}$ concentration to increase inside the cell, as $Ca^{2+}$ cannot be pumped out. Increase in $Ca^{2+}$ concentration thus aid contraction in the heart. Digoxin also acts as a vagal agonist, with a secondary effect of decreased heart rate. Digoxin toxicity is marked by atrial tachycardia (due to ectopy) and AV block (due to its vagal stimulating properties). Digoxin further reduces the risk of certain kinds of cancer, but not at the therapeutic concentrations used to treat cardiac diseases.

There is a need in the art to identify novel therapeutic treatments that can be used to treat or prevent non-alcoholic steatohepatitis (also known as NASH) in a mammal. There is also a need in the art to identify novel therapeutic treatments that can be used to treat or prevent other liver diseases or disorders, such as, but not limited to, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions in a mammal. There is also a need in the art to identify novel therapeutic treatments that can be used to treat or prevent promote weight loss in a mammal. The present invention addresses and meets these needs.

BRIEF SUMMARY OF THE INVENTION

The invention provides a method of treating or preventing in a mammal in need thereof a liver disease or disorder selected from the group consisting of non-alcoholic steatohepatitis (NASH), liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. The invention further provides a method of promoting weight loss in a mammal in need thereof. The invention further provides a kit comprising at least one cardiac glycoside, an applicator, and an instructional material for use thereof. The invention further provides a pharmaceutical composition comprising at least one cardiac glycoside, or a solvate, salt, prodrug or derivative thereof, wherein the at least one cardiac glycoside comprises digoxin, whereby administration of the composition to a mammal affords a digoxin plasma level that is equal to or lower than about 0.8 ng/ml in the mammal. The invention further provides a pharmaceutical composition comprising at least one cardiac glycoside (or a solvate, salt, prodrug or derivative thereof) and at least one additional agent (or a solvate, salt, prodrug or derivative thereof) that treats, prevents or reduces the symptoms of a liver disease or disorder selected from the group consisting of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. The invention further provides a pharmaceutical composition comprising at least one cardiac glycoside (or a solvate, salt, prodrug or derivative thereof) and at least one additional agent that promotes weight loss (or a solvate, salt, prodrug or derivative thereof).

In certain embodiments, the method comprises administering to the mammal a therapeutically effective amount of at least one cardiac glycoside. In other embodiments, administration of the at least one cardiac glycoside to the mammal affords a cardiac glycoside plasma level in the mammal that is equal to or lower than the cardiac glycoside plasma level required to treat or prevent a cardiac disease in mammals afflicted with the cardiac disease. In yet other embodiments, administration of the composition and/or at least one cardiac glycoside to the mammal affords a cardiac glycoside plasma level in the mammal that is lower than the cardiac glycoside plasma level required to treat or prevent a cardiac disease in mammals afflicted with the cardiac disease.

In certain embodiments, the cardiac glycoside reduces fat-induced obesity in the mammal. In other embodiments, the mammal does not experience significant reduction in food intake. In yet other embodiments, the mammal is further administered at least one additional agent that promotes weight loss. In yet other embodiments, administration of the at least one cardiac glycoside to the mammal does not cause a clinically significant cardiac effect in the mammal. In yet other embodiments, the clinically significant cardiac effect comprises at least one selected from the group consisting of occurrence of atrial tachycardia, occurrence of atrioventricular block, reduction in atrioventricular node conduction, and increase in effective refractory period within the atrioventricular node. In yet other embodiments, the cardiac glycoside inhibits HIF-1α synthesis in the liver of the mammal. In yet other embodiments, the cardiac glycoside inhibits inflammation in the mammal's liver. In yet other embodiments, the cardiac glycoside inhibits liver steatosis in the mammal. In yet other embodiments, the cardiac glycoside reduces in the mammal at least one condition selected from the group consisting of liver damage and glycolysis. In yet other embodiments, the cardiac glycoside reduces fat-induced obesity in the mammal. In yet other embodiments, the cardiac glycoside improves glucose tolerance in the mammal. In yet other embodiments, the cardiac glycoside reduces one or diabetic symptoms and/or complications in the mammal.

In certain embodiments, the at least one cardiac glycoside is at least one selected from the group consisting of acetyl-digitoxin, bufalin, cinobufagerin, convallatoxin, cymarin, digitoxigenin, digotoxin, digoxigerin, digoxin, gitoxigenin, gitoxin, marinobufagenin, nerifolin, oleandrin, ouabain, periplocymarin, peruvoside, proscillaridin A, strophanthin K, and UNBS1450.

In certain embodiments, the at least one cardiac glycoside comprises digoxin. In other embodiments, the at least one cardiac glycoside comprises digoxin, and administration of the at least one cardiac glycoside to the mammal affords a digoxin plasma level that is equal to or lower than about 0.8 ng/ml. In yet other embodiments, the at least one cardiac glycoside comprises digoxin, and administration of the at least one cardiac glycoside to the mammal affords a digoxin plasma level selected from the group consisting of: about 0.02 to about 0.05 ng/ml; about 0.05 to about 0.1 ng/ml; about 0.05 to about 0.15 ng/ml; about 0.05 to about 0.2 ng/ml; about 0.05 to about 0.25 ng/ml; about 0.05 to about 0.3 ng/ml; about 0.05 to about 0.35 ng/ml; about 0.05 to about 0.4 ng/ml; about 0.05 to about 0.45 ng/ml; about 0.05 to about 0.5 ng/ml; about 0.05 to about 0.55 ng/ml; about 0.05 to about 0.6 ng/ml; about 0.05 to about 0.65 ng/ml; about 0.05 to about 0.7 ng/ml; about 0.05 to about 0.75 ng/ml; and about 0.05 to about 0.8 ng/ml.

In certain embodiments, the at least one cardiac glycoside is administered to the mammal about once a day, about every other day, about every third day, about every fourth day, about every fifth day, about every sixth day, or about once a week.

In certain embodiments, the mammal is further administered at least one additional agent that reduces the symptoms of, treats or prevents a liver disease or disorder selected from the group consisting of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. In other embodiments, the at least one additional agent comprises an anti-diabetic medicament or abeticholic acid. In yet other embodiments, the at least one cardiac glycoside is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous. In yet other embodiments, the mammal is a human.

In certain embodiments, the instructional material comprises instructions for preventing or treating in a mammal a liver disease or disorder selected from the group consisting of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. In other embodiments, the kit further comprises at least one additional agent that treats, prevents or reduces the symptoms of a liver disease or disorder selected from the group consisting of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. In yet other embodiments, the at least one additional agent comprises an anti-diabetic medicament or abeticholic acid. In yet other embodiments, the instructional material comprises instructions for promoting weight loss in a mammal. In yet other embodiments, the kit further comprises at least one additional agent that promotes weight loss. In yet other embodiments, administration to the mammal of the at least one cardiac glycoside amount described in the instructional material affords a cardiac glycoside plasma level in the mammal that is equal to or lower than the cardiac glycoside plasma level required to treat or prevent a cardiac disease in mammals afflicted with the cardiac disease.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1J illustrate the finding that adenosine stimulates IL-1β production in NLRP3 inflammasome-dependent manner. Murine peritoneal macrophages (PECs) were obtained from wild type (WT) mice (FIGS. 1A-1D, 1F-1I), Il1r−/− (FIG. 1E) or Nlrp3−/−, ASC−/−, P2xr7−/−, or Caspase-1−/− mice (FIG. 1J) and were primed with LPS for 16 hours. FIG. 1A: This was followed by treatment for 1 hour with adenosine (Ad, 100 μM), adenosine deaminase inhibitor (EHNA, 10 μM), adenosine deaminase (ADA, 10 U ml$^{-1}$), ATP diphosphohydrolase (Apyrase, 10 U ml$^{-1}$), or erythro-9-(2-hydroxy-3-nonyl) adenine (EHNA, 10 μM) (FIGS. 1B, 1F-1J)). Pan adenosine agonist (NECA, 1 μM, 10 μM) (FIGS. 1C, 1E), or (FIGS. 1D, 1I) by NECA for 1 and 6 hours, and were then pulsed with ATP for 20 min. Enzyme-linked immunosobent assay (ELISA) of IL-1β, TNF-α, IL-10 and IFN-γ secretion were measured in cell supernatants after pulsing with ATP for 5 hours (FIGS. 1A, 1C-1E, 1J) or indicated time-course (FIGS. 1B, 1G-1I). LDH assay was performed after pulsing with ATP as indicated time-course (FIG. 1F). Data are expressed as the mean±SD from at least three independent experiments. *p<0.05 determined by Student's t-test.

FIGS. 2A-2H illustrate the finding that adenosine mediates increase in IL-1β via the $A_{2A}$ receptor and amplifies signal 1 and signal 2 pathways. FIG. 2A: LPS primed PECs were treated with NECA (10 μM) in the presence or absence of three different adenosine receptor antagonists for $A_1$ (DPCPX, 10 nM), $A_{2A}$ (ZM 241385, 10 μM), $A_{2B}$ (MRS1706, 10 nM), $A_3$ (MRS1523, 5 μM), or their combinations for 1 hour, and pulsed with ATP for 20 min. FIGS. 2A-2B: $A_{2A}$ receptor specific agonist (CGS21680) and antagonist ZM 241385 increase and block IL-1β production respectively. FIG. 2C: LDH release in PECs showed no difference in the presence or absence of ZM 241385 as sampled from FIG. 2A. FIG. 2D: PEC's from $A_{2A}$ receptor deficient cells have low IL-1β production, which is not increased by NECA and CGS 21680. FIG. 2E: CGS21680 increases induction of Il1b mRNA expression, and this was decreased in $A_{2A}$ receptor deficient cells. FIG. 2F: Loss of the $A_{2A}$ receptor in macrophages results in much lower levels of Il1b protein A expression in response to LPS. FIG. 2G: CGS21680 and ZM241395 increases and decreases production of cleaved caspase-1, respectively. FIG. 2H: The production of cleaved caspase-1 is decreased in $A_{2A}$ receptor deficient macrophages. Data are expressed as the mean±SD from at least three independent experiments Immunoblots shown are representative results from at least three independent experiments. p<0.05 determined by Student's t-test.

FIG. 3A: Primed (pri) with LPS (100 ng/ml) for 16 hours followed by stimulation (stim) with LPS (100 ng/ml), or NECA (10 μM) or CGS21680 (10 μM) in the presence or absence of LPS (100 ng/ml) for 6 hours. FIG. 3B: Treated with forskolin for 6 hours as indicated doses with and without LPS priming FIG. 3C: Treated with or without NECA (10 μM), CGS21680 (10 μM) or db-cAMP (200 μM) for 6 hours. FIG. 3D: LPS primed and treated with NECA or CGS21680 in the presence and absence of SQ22536, H89 and PKi. FIG. 3E: Primed with LPS for 16 hours and treated with ATP for 20 min, followed by CGS 21680 in the presence or absence of the adenylyl cyclase and PKA inhibitors SQ22536 and H-89. FIG. 3F: Primed with LPS and treated with or without NECA (10 μM) or db-cAMP (200 μM) for 6 hours. FIG. 3G: Treated with or without CGS21680 (10 μM) for 3 hours, and transcription was stopped by adding 5 mg/ml actinomycin D, and RNA samples collected at indicated times-points. FIG. 3H: LPS primed PECs obtained from wild type or $A_{2A}$R-cKO mice were stimulated with NECA (10 μM) for 6 hours. The cells were harvested and RNA isolated after each treatment and the gene expression of Il1b and other genes as indicated quantified by real-time PCR using specific primers. FIG. 3I: Primed with LPS for 16 hours and treated with ATP for 20 min, followed by CGS 21680 in the presence or absence of SQ22536 or H-89 Immunoblot analysis of the proIL-1β caspase-1 in cell lysate was performed by specific anti-IL-13 and anti caspase-1 p10 antibodies (FIGS. 3C, 3E-3F, 3I). Data are expressed as the mean±SD from three independent experiments Immunoblots shown are representative results from at least three independent experiments. *p<0.05 determined by Student's t-test.

FIG. 4A: Consensus NFκB and HRE binding sites in the IL-1β promoter. FIG. 4B: LPS primed PECs obtained from $A_{2A}$R-cKO and controls were stimulated with or without NECA or CGS21680. FIG. 4C: LPS primed PECs obtained from HIF-1α-cKO and controls were stimulated with or without NECA at time points as indicated. Cells were harvested and RNA isolated after each treatment and gene expression of Il1b and Hif1α quantified by real-time PCR. FIG. 4D: THP-1 cells were transfected with HRE-promoter luciferase construct and β-galactosidase plasmid in the presence or absence of CREB dominant negative plasmid (CREBΔ), and then primed with LPS/PMA followed by NECA. FIG. 4E: THP-1 cells were transfected with human IL-β promoter luciferase construct and β-galactosidase plasmid in the presence or absence of CREBΔ, and then primed with LPS/PMA followed by CGS21680 or NECA. Luciferase activities were measured and normalized to β-galactosidase activity and normalized with controls. Data are mean±SD of triplicate cultures and are representative of three independent experiments. FIG. 4F: CD14-MD2-TLR4-HEK 293 cells were transfected with NFκB promoter luciferase construct and Renilla luciferase (Rluc) control reporter vector, and then treated with CGS21680, NECA or ZM241395 in the presence of LPS. Luciferase activities were measured and normalized to Rluc activity and the normalized value with controls as indicated. Data are mean±SD of triplicate cultures and are representative of three independent experiments for FIGS. 4B-4F. FIG. 4G: LPS primed PECs obtained from HIF-1α-cKO and controls were treated with or without NECA at different time points as indicated followed pulsing with ATP. Cell supernatants were collected in 5 hours after ATP pulsing. IL-1β was measured in cell supernatant by ELISA. Data are expressed as the mean±SD from three independent experiments. FIG. 4H: LPS primed PECs obtained from HIF-1α-cKO and control mice were treated with or without NECA at different time points as indicated followed by pulsing with ATP. Cell lysates were collected after ATP pulsing. HIF-1α, pro-caspase-1, Caspase-1 and pro-IL-1β was measured in cell supernatant by western blot Immunoblots shown are representative results from at least three independent experiments.

FIG. 5A: $A_{2A}$R-cKO and control mice were injected intraperitoneally with LPS (1 mg/kg) and D-galactosamine (500 mg kg$^{-1}$) for 6 hours followed by liver tissue and serum collection for H&E staining and ALT assay. FIG. 5B: Liver RNA samples were collected and Il1b gene assayed by real-time PCR using specific primers. FIG. 5C: Liver tissue lysates were assayed for procaspase-1, cleaved caspase-1 (p10), and β-actin protein level by immunoblot analysis using specific antibodies. Data are expressed as the mean±SD from 10-11 mice from each group for FIGS.

5A-5D. FIG. 5d: Serum was collected for measurement of IL-1β. FIG. 5E: $A_{2A}$R-cKO and control mice were injected intraperitoneally with single dose of TAA followed by liver tissue collection as indicated for H&E staining. FIG. 5F: Liver RNA samples were collected and Il1b gene was assayed by real-time PCR. FIG. 5G: Liver tissue was also obtained at day 7 after TAA injection and stained for H&E and Sirius red for fibrosis. FIG. 5H: Sera were collected and the serum ALT assay was performed (Data are expressed as the mean±SD from 5 mice in each group). *$p<0.05$ determined by Student's t-test. Scale bars correspond to 500 μm.

FIG. 6A: Murine bone marrow derived macrophages (BMDM) were primed with LPS for 16 hours, treated with NECA (10 μM) for 1 hour, and then pulsed with ATP. FIG. 6b: Primary murine liver Kupffer cells were primed with LPS for 16 hours, treated with NECA (10 μM) for 1 hour, and then pulsed with ATP. IL-1β secretion was measured in supernatants 5 hours after pulsing with ATP. Data are expressed as the mean±SD from at least three independent experiments. *$p<0.05$ determined by Student's t-test.

FIG. 7A: LPS primed PECs were treated with NECA (10 μM) for 1 hour, and then exposed to MSU for 6 hours. FIG. 7B: CpG-B primed PECs were treated with EHNA (10 μM) for 1 hour and then pulsed with ATP. FIG. 7C: P CpG-B primed PEC treated with ZM241385 (10 μM), and then pulsed with ATP. FIG. 7D: Pam(3)CySSK(4) primed PECs treated with ZM241385 (10 μM), and then pulsed with ATP. FIG. 7E: LPS primed PECs were treated with ZM241385 (10 μM), and then stimulated with 150 micron PMMA beads. FIG. 7F: LPS primed PECs were treated with ZM241385 (10 μM), and then exposed to MSU for 6 hours. FIG. 7G: PECs were pretreated with or without ZM241385 (10 μM) for 1 hour, and then stimulated with liver lysate for 2 hours. IL-1β secretion was measured in supernatants 5 hours after pulsing with ATP. FIG. 7H: MSU crystals were injected intraperitoneally into wild type mice with or without ZM241385, and IL-1β was quantified in the peritoneal lavage after 6 hours. Data are expressed as the mean±SD from 6 mice in each group. *$p<0.05$ determined by Student's t-test.

FIG. 8A: PEC cells obtained from Adora2afl/fl-LysM-Cre+ ($A_{2A}$R-cKO) and Adorafl/fl-LysM-Cre-control (Ctrl) mice were stimulated with LPS (100 ng ml$^{-1}$), Pam(3)CySSK(4) (10 ng ml$^{-1}$) or CpG-B (3 μM) for 6 hours. The cells were harvested and RNA isolated after each treatment, and the gene expression of Adora2a quantified by real-time PCR using specific gene primers. Data are expressed as the mean±SD from three independent experiments. FIG. 8B: PEC cells obtained from HIF-1αfl/fl-LysM-Cre+(HIF-1α-cKO) and HIF-1αfl/fl-LysM-Cre-control (Ctrl) mice were exposed to hypoxia over 12 hours. The cell lysates were analysed by immunoblotting using specific HIF-1α antibody. The immunoblot data shown are representative of three independent experiments FIGS. 9A-9H illustrate changes in expression of cytokines and tissue repair genes in peritoneal macrophages in response to adenosine agonists. LPS naive or LPS primed PECs were stimulated with LPS (100 ng ml$^{-1}$), CGS21680 (10 μM) or NECA (10 μM) at different time points as indicated. The cells were harvested and RNA isolated after each treatment, and the gene expression of ProIL-1β (Il1b) (FIG. 9A), IL-6 (Il6) (FIG. 9B), IL-4 (Il4) (FIG. 9C), TNF-α (tnfa) (FIG. 9D), TIMP-1 (Timp1) (FIG. 9E), VEGF (vegf) (FIG. 9F), PGK-1 (Pgk1) (FIG. 9G), GLUT-1 (Slc2a1) (FIG. 9H) quantified by real-time PCR using each specific gene primer set as listed. Data are expressed as the mean±SD from three independent experiments. *$p<0.05$ determined by Student's t-test.

FIGS. 10A-10F illustrate the expression of antimicrobial genes in $A_{2A}$R and Il1r deficient peritoneal macrophages by adenosine agonists. LPS naive or LPS primed PECs were stimulated with LPS (100 ng ml$^{-1}$) or NECA (10 μM) for 6 hours. The cells were harvested and RNA isolated after each treatment, and the gene expression of Marco (FIGS. 10A, 10D), Ptges (FIGS. 10B, 10E), and Fpr1 (FIGS. 10C, 10F), quantified by real-time PCR using each specific gene primer set as listed. Data are expressed as the mean±SD from three independent experiments. *$p<0.05$ determined by Student's t-test.

FIGS. 11C-11D: In 3 hours LPS primed BMDM were treated with forskolin at different dose as indicated for 1 hour, and then pulsed with ATP. The cell supernatants were collected in 5 hours after ATP pulsing for IL-1β assay by ELISA (FIG. 11C), and the cell lysates were harvested for active caspase-1 by western blot (FIG. 11D). Data are expressed as the mean±SD from three independent experiments. *$p<0.05$ determined by Student's t-test.

FIG. 12A: LPS primed PECs were stimulated NECA (10 μM) in the presence or absence of HIF-1α inhibitor CAY 10585 (30 μM) for 6 hours. The cells were harvested and RNA isolated after each treatment, and the gene expression of Il1a quantified by real-time PCR using specific gene primers. Data are expressed as the mean±SD from three independent experiments. FIG. 12B: LPS primed PECs were treated with or without CGS21680 (10 μM) or NECA (10 μM) for 1 hour, or CAY10585 and then pulsed with ATP. IL-1β secretion in cell supernatants was measured after 5 hours of ATP pulsing. Data are expressed as the mean±SD from three independent experiments. FIGS. 12C-12D: LPS primed PECs obtained from wild type or HIF-1α-cKO mice were stimulated NECA (10 μM) for 6 hours. The cells were harvested and RNA isolated after each treatment, and the gene expression of Nlrp3 and Txnip quantified by real-time PCR using each specific gene primer set. Data are expressed as the mean±SD from three independent experiments. * $p<0.05$ determined by Student's 1-test.

(FIG. 15A) Diagram of TAA (200 mg kg$^1$ body weight) injection. FIGS. 15B-15C: The liver tissue and serum were collected in 16 hours after last injection, the tissue lysates were applied for Pro- and mature IL-10 by western blot (FIG. 15B), and the serum IL-1β levels were determined by ELISA (FIG. 15C). Data are expressed as the mean±SD from 5 mice in each group. *p<0.05 determined by Student's t-test.

FIG. 16A: Wild type and Casp-1-/- mice were injected intraperitoneally with TAA with co-injection of CGS21680 (2.5 mg kg$^{-1}$ body weight) or vehicle. The liver tissues from each group were collected 3 days after first injection, and tissue collagen visualized by Sirius red staining, and the representative images are shown. Scale bar corresponds to 500 μm. FIG. 16B: Total liver RNA was extracted and Timp1 mRNA levels quantified. Data are expressed as the mean±SD from three independent experiments. * p<0.05 determined by Student's t-test.

FIG. 21A: Wild type C57BL/6 mice were supplied with high-fat diet food (Research diets D12451 45% fat) for 12 weeks with or without the concurrent IP injection of Digoxin (twice a week, 1.0 mg/kg) or PBS control. The liver tissues were performed by H & E staining, and the neutrophils were stained with CD11b/Ly6G double positive cells by FACS. Data are expressed as the mean±SD from 5 mice in each treatment group. *p<0.05 determined by Student's t-test. FIG. 21B: The serums were collected from as illustrated in FIG. 21a, and subjected to determination of serum total cholesterol level by enzyme-lined method. Data are expressed as the mean±SD from 5 mice in each treatment group. *p<0.05 determined by Student's t-test. FIG. 21C: The liver total RNA were isolated from as procedure from FIG. 21a, and subjected to illumina transcriptome analysis. Over 15 genes that most highly expressed were listed. Data are expressed as the mean±SD from 3 mice in each treatment group FIG. 22A illustrates examples of mice on high-fat diet with (DIG) and without (Ctrl) digoxin. Mice on HFD registered less weight gain (FIG. 22B). The ratio of white adipose tissue and bodyweight after 12 weeks is shown (FIG. 22C). No significant change in food intake (as the change of each 3 day's average) was observed for the mice on HFD (FIG. 22D). Data are expressed as the mean±SD from 5 mice in each treatment group. *p<0.05 determined by Student's t-test.

FIG. 24A: C57BL/6 mice were on HFD or chow concurrently with intraperitoneal injection of digoxin (1 mg/kg) and saline control twice a week for 12 weeks (FIGS. 24A, 24C, 24F, 24G), or on HFD for first 5 weeks and then started concurrently with intraperitoneal injection of digoxin (1 mg/kg) for further 3 weeks (FIGS. 24B, 24D, 24E, 24H). The liver tissues were applied for H & E staining, and graphs show quantification of NAFLD histological activity score (FIGS. 24A-24B). The liver tissue inflammation was also determined by the neutrophil and monocyte infiltration, which measured by CD11b/Ly6G and CD11b/Ly6C double positive cells using FACS (FIGS. 24F-24H). Representative FACS flows from digoxin versus saline control are shown (FIGS. 24F-24G). The quantification of neutrophils and monocytes in digoxin versus saline control was performed. Serum ALT level in digoxin versus saline control was measured (FIGS. 24C-24D). The steatosis maker of triacylglcerol (TG) accumulation in the lever after digoxin treatment versus saline control was determined (FIG. 24E). All data throughout the figure are shown as the mean±SD from 5 mice in each group. Statistical significance was determined by one-way ANOVA. *p<0.05, **p<0.01 for each digoxin group versus saline control.

FIGS. 25A-25H illustrate the finding that digoxin alleviates hepatic oxidative stress and inflammasome activation. C57BL/6 mice were injected intraperitoneally with digoxin (1 mg/kg) and PBS control for 1 hour, and then challenged with LPS (1 mg/kg)/D-GlaN (500 mg/kg) for 5 h; C57BL/6 mice were on HFD with concurrent intraperitoneal injection of digoxin (1 mg/kg) for 12 weeks. The cellular oxidative stress and intracellular ROS production was monitored by intraperitoneal injection of DHE in last 30 min before the mice sacrificed. Representative DHE stains in LPS/D-GlaN (FIG. 25A) and HFD (FIG. 25B) from digoxin versus saline control are illustrated. The quantification of DHE positive area in digoxin versus saline control was performed (FIG. 25A, lower, and FIG. 25B, lower). The total RNA from liver tissue was isolated, and applied for gene expression of proIL-1β, TNFα, NLRP3 and HIF1a (FIGS. 25C-25F). The total liver protein was applied for protein expression of HIF1α, caspase-1, proIL-1β by western blot (FIG. 25H). The serum IL-1β was measured by ELISA (FIG. 25G). All data throughout the figure are shown as the mean±SD from 5 mice in each group. Statistical significance was determined by one-way ANOVA. *p<0.05, **p<0.01 for each digoxin group versus saline control.

DETAILED DESCRIPTION OF THE INVENTION

Figure 1A:
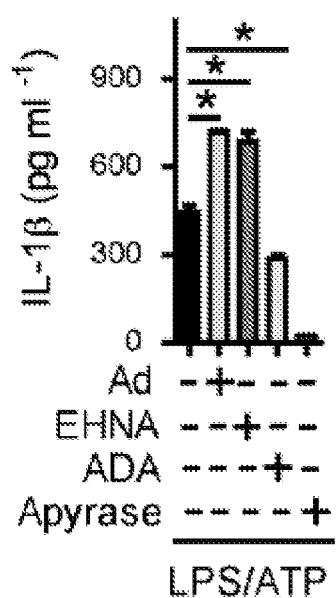

In one aspect, the present invention relates to the unexpected discovery that low doses of cardiac glycosides are effective in treating or preventing non-alcoholic steatohepatitis (NASH) in a mammal. In another aspect, the present invention relates to the unexpected discovery that low doses of cardiac glycosides are effective in treating or preventing liver diseases or disorders, such as but not limited to liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions in a mammal. In yet another aspect, the present invention relates to the unexpected discovery that low doses of cardiac glycosides are effective in treating or preventing autoimmune hepatitis, primary biliary cirrhosis, and other toxic and/or inflammatory liver conditions in a mammal. In yet another aspect, the present invention relates to the unexpected discovery that low doses of cardiac glycosides are effective in promoting weight loss in a mammal.

In certain embodiments, administration of the cardiac glycoside to the mammal inhibits inflammation in the mammal's liver. In other embodiments, administration of the cardiac glycoside to the mammal inhibits liver steatosis in the mammal. In yet other embodiments, administration of the cardiac glycoside to the mammal reduces liver damage and/or glycolysis in the mammal. In yet other embodiments, administration of the cardiac glycoside to the mammal reduces fat-induced obesity in the mammal. In yet other embodiments, administration of the cardiac glycoside to the mammal results in weight loss without reduction in food intake. In yet other embodiments, the cardiac glycoside improves glucose tolerance in the mammal. In yet other embodiments, the cardiac glycoside reduces one or more diabetic symptoms and/or complications in the mammal. In yet other embodiments, the mammal is human.

The present invention contemplates that the biological effects recited herein can be associated with the cardiac glycoside itself and/or one or more metabolites thereof formed in the body of the mammal. In certain embodiments, the present invention contemplates administering therapeutically effective amounts of the biologically active cardiac glycoside metabolite(s) to the mammal to elicit the biological effects recited herein.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein, the term "clinically significant cardiac effect" as relating to a drug dose indicates that, once administered to a subject, the drug dose does not cause significant, deleterious and/or measurable cardiac effects in the subject.

In one aspect, the terms "co-administered" and "co-administration" as relating to a subject refer to administering to the subject a compound of the invention, or a derivative, solvate, salt or prodrug salt thereof, along with a compound that may also treat the disorders or diseases contemplated within the invention. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

As used herein, the term "digoxin" refers to 4-[(3S,5R,8R,9S,10S,12R,13S,14S)-3-[(2S,4S,5R,6R)-5-[(2S,4S,5R,6R)-5-[(2S,4S,5R,6R)-4,5-dihydroxy-6-methyl-oxan-2-yl]oxy-4-hydroxy-6-methyl-oxan-2-yl]oxy-4-hydroxy-6-methyl-oxan-2-yl]oxy-12,14-dihydroxy-10,13-dimethyl-1,2,3,4,5,6,7,8,9,11,12,15,16,17-tetradecahydro cyclopenta[a]phenanthren-17-yl]-5H-furan-2-one, or a salt or solvate thereof.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "HFD" refers to high-fat diet.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

The terms "patient," "subject" or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions.

The "pharmaceutically acceptable carrier" may further include a pharmaceutically acceptable salt, prodrug, solvate or derivative of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

The term "prevent," "preventing" or "prevention," as used herein, means avoiding or delaying the onset of symptoms associated with a disease or condition in a subject that has not developed such symptoms at the time the administering of an agent or compound commences.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

By the term "specifically bind" or "specifically binds," as used herein, is meant that a first molecule preferentially binds to a second molecule (e.g., a particular receptor or enzyme), but does not necessarily bind only to that second molecule.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Disclosure

Figure 17A:
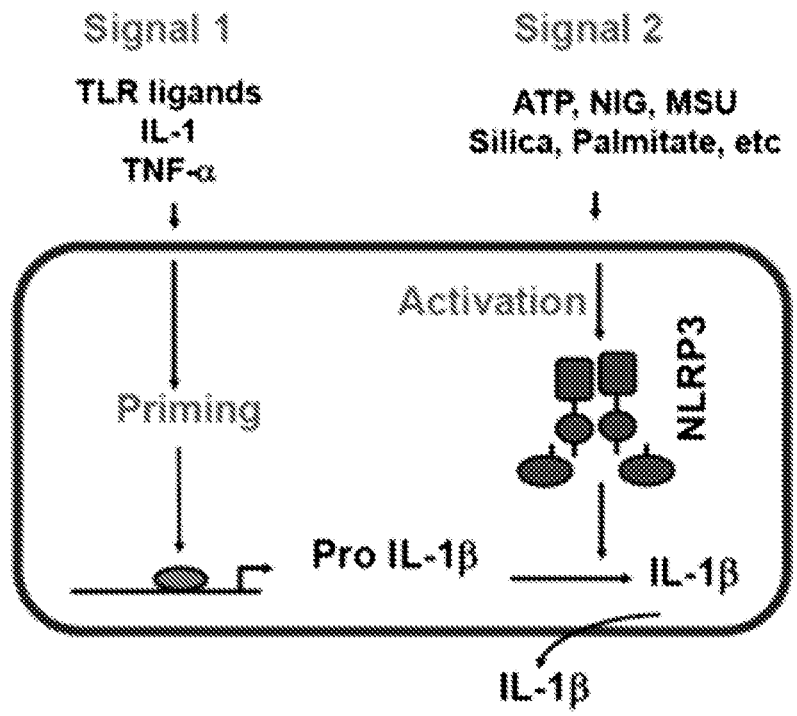
FIGS. 17A-17B illustrate the two signals (signal 1 and signal 2) involved in inflammasome activation (FIG. 17A) and the role that adenosine plays in regulating inflammasome activation (Fig. B.

The production of IL-1β is a central step in a wide range of acute and chronic inflammatory and fibrotic responses. Two distinct pathways are known to be required for initial inflammasome activation and IL-1β production (FIG. 17A). The signal 1 pathway is typically considered to be activated via Toll-like receptors, resulting in NFkβ mediated up-regulation of the Pro-ILβ gene, as well as genes for inflammasome components. A second pathway (signal 2) is required for activation of the inflammasome machinery. Signal 2 is delivered by a wide range of stimuli, which range from pathogen derived molecules such as flagellin and cytosolic DNA, and non-pathogen derived particulates such as uric acid crystals.

The above two pathways appear to provide the minimum requirements for inflammasome activation, however their activation is associated with an acute production of IL-1β that is significantly resolved within 24 hours. Inflammasome activation also has an important role in a number of chronic inflammatory and fibrotic diseases. Sustained production of IL-1β could theoretically occur within the framework of the above pathways by a greater number, concentration or duration of exposure to ligands which initiate signal 1 and 2 pathways. However, persistent exposure to PAMPs results in the development of a tolerogenic state, and signal 2 pathways such as ATP induce cell death.

Figure 17B:
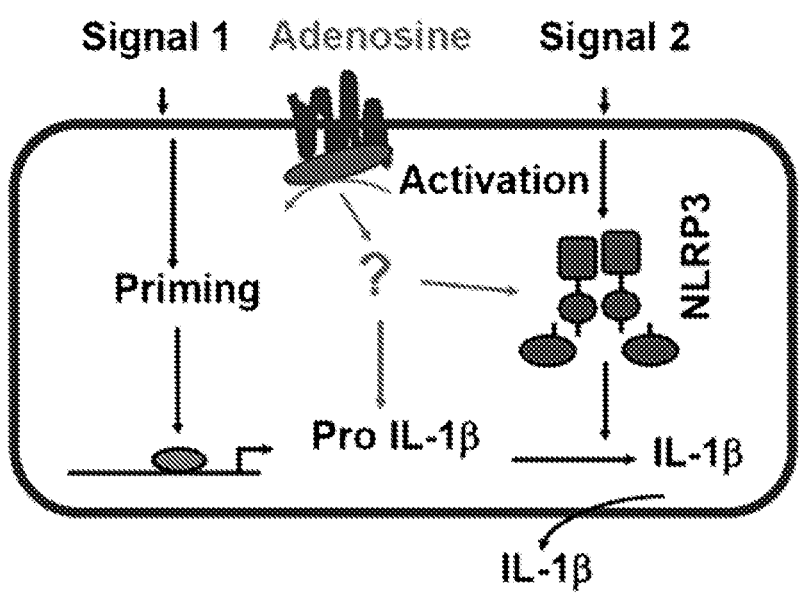
Figure 18:
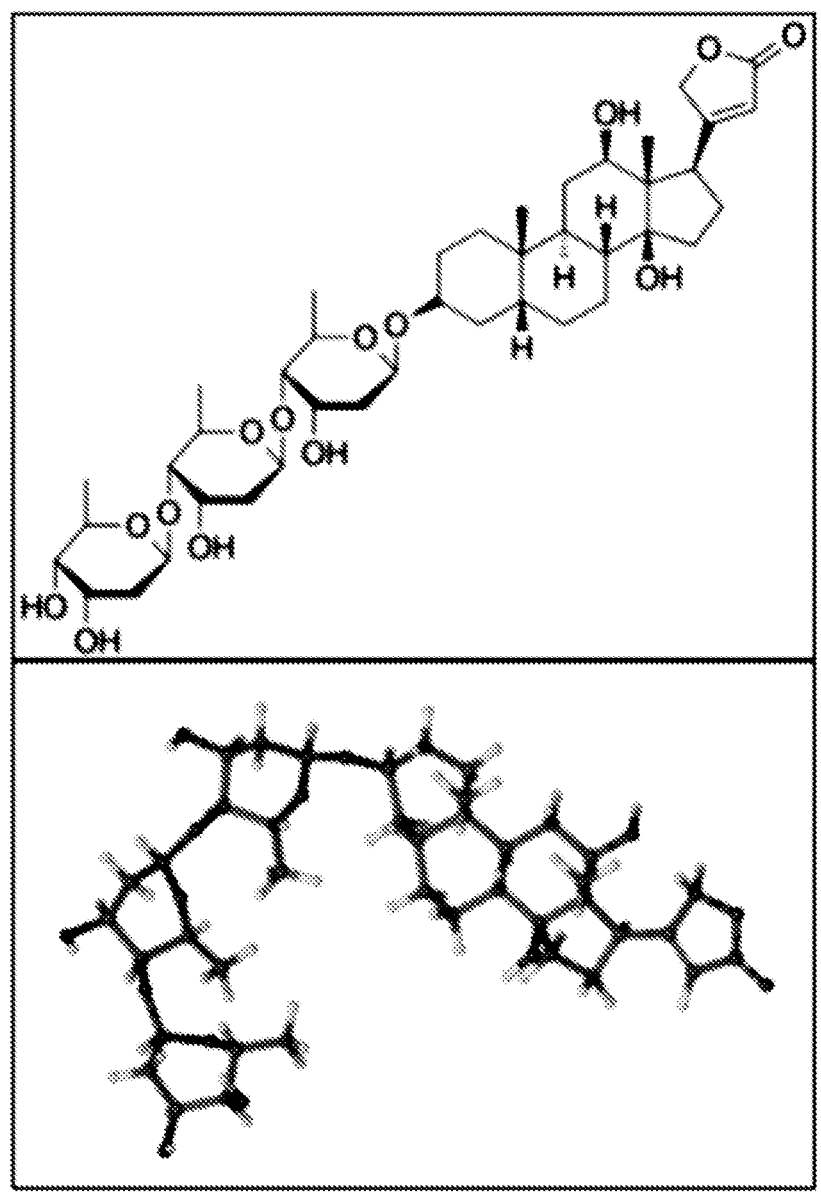
FIG. 18 illustrates the structure of digoxin.
Figure 19:
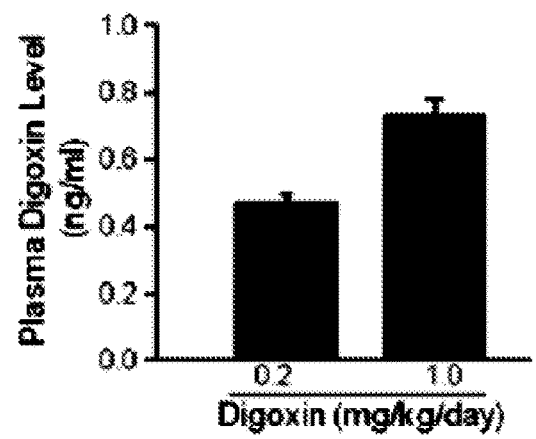
FIG. 19 is a bar graph illustrating plasma digoxin levels in mice. Saline or digoxin were daily injected in mice at a dose of 1.0 mg/kg. Plasma digoxin levels measured 24 hours after the final injection were at or below the therapeutic range for humans (0.8-2 ng/mL).
Figure 20A:
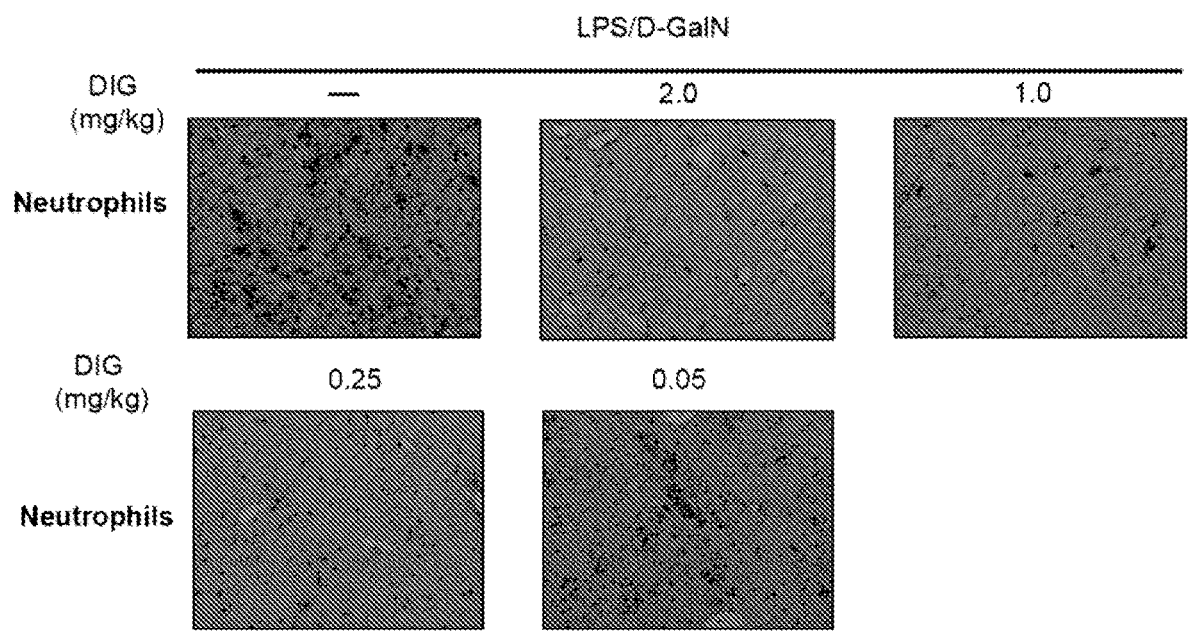
FIGS. 20A-20C illustrate the finding that digoxin inhibits inflammation in an acute liver injury model.
Figure 20B:
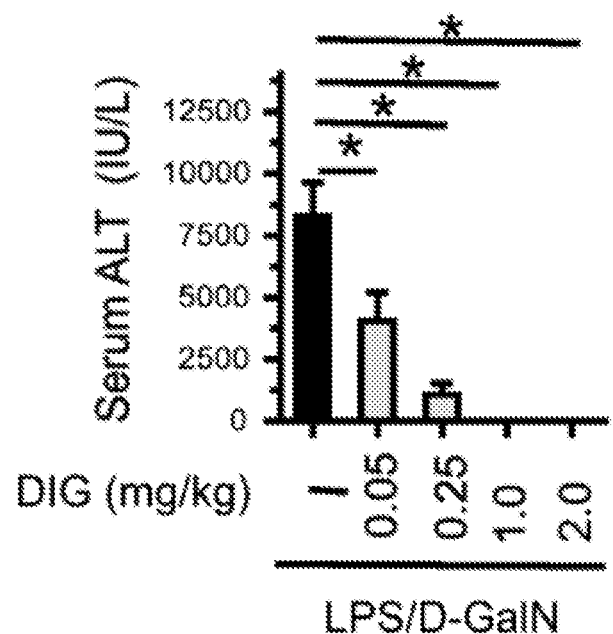
Figure 20C:
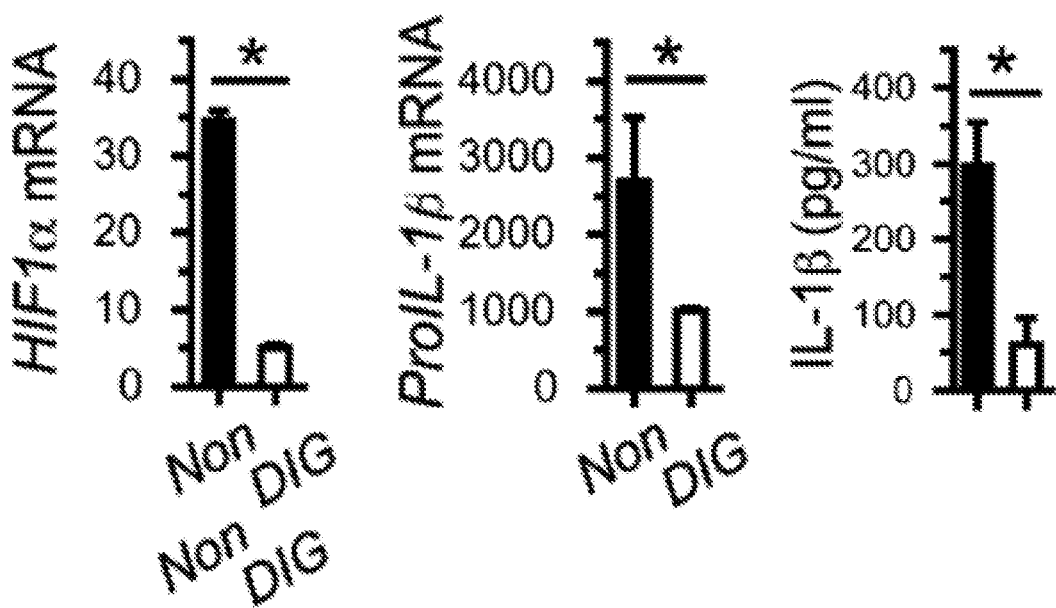
Figure 21A:
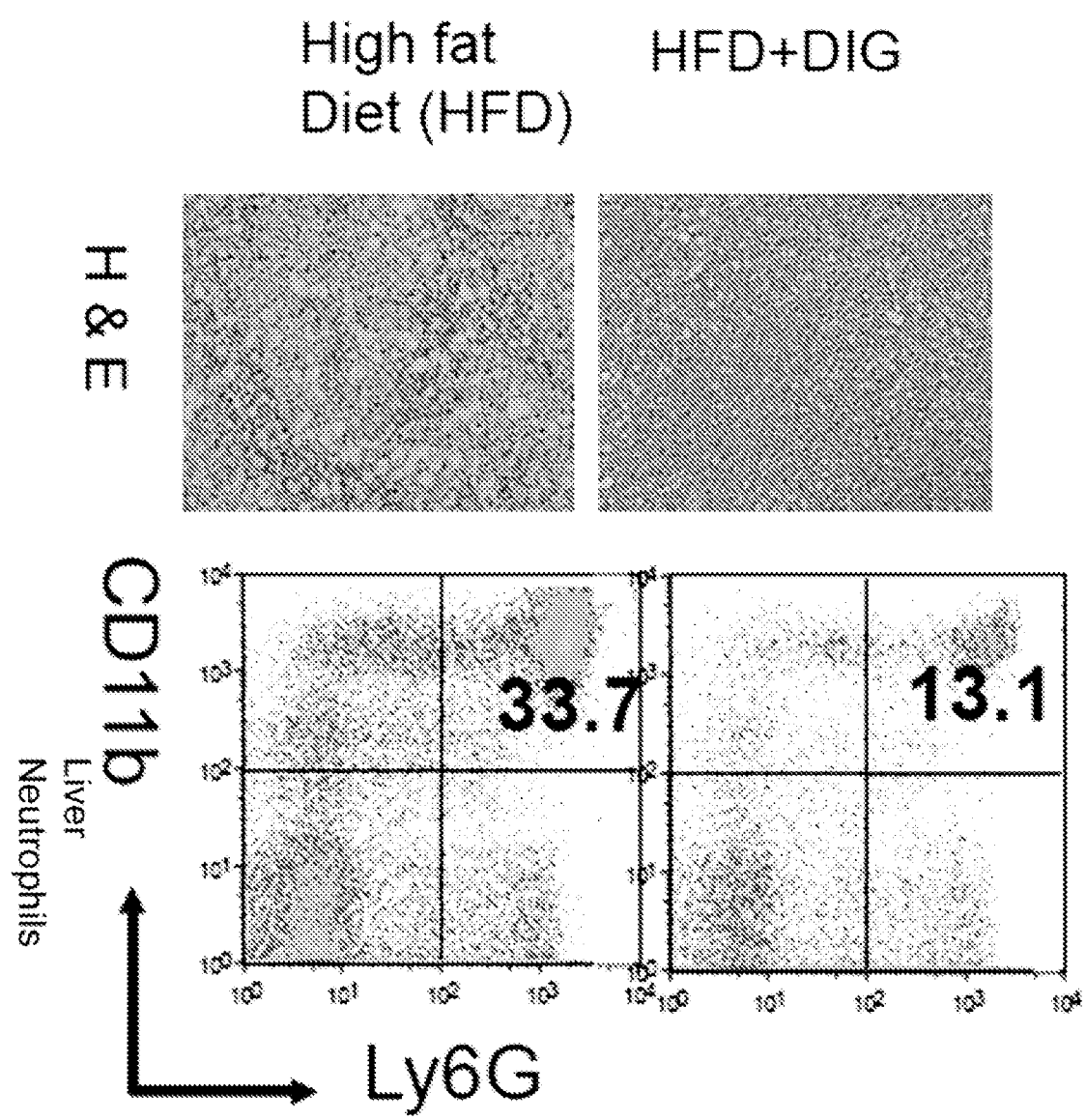
FIGS. 21A-21C illustrate the finding that digoxin reduces liver damage, inflammation, glycolysis and total cholesterol.
Figure 21B:
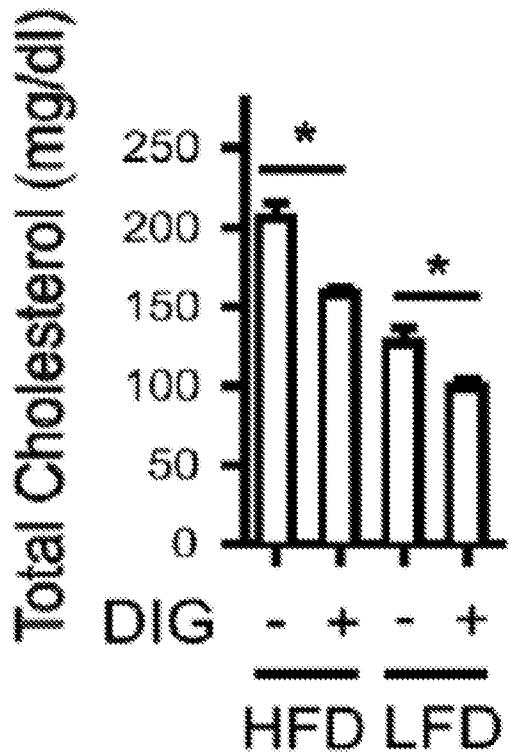
Figure 21C:
Figure 22A:
FIGS. 22A-22D illustrate the finding that digoxin reduces high fat feeding induced obesity in mice. Wild type C57BL/6 mice were supplied with high-fat diet food (Research diets D12451 45% fat) for 12 weeks with or without the concurrent IP injection of Digoxin (twice a week, 1.0 mg/kg) or PBS control. The body weight was carefully monitored as the change of each 3 day's average. A representative picture showed the morphological changes of mice that I.P. injected with or without digoxin (1 mg/kg) for 12 weeks.
Figure 22B:
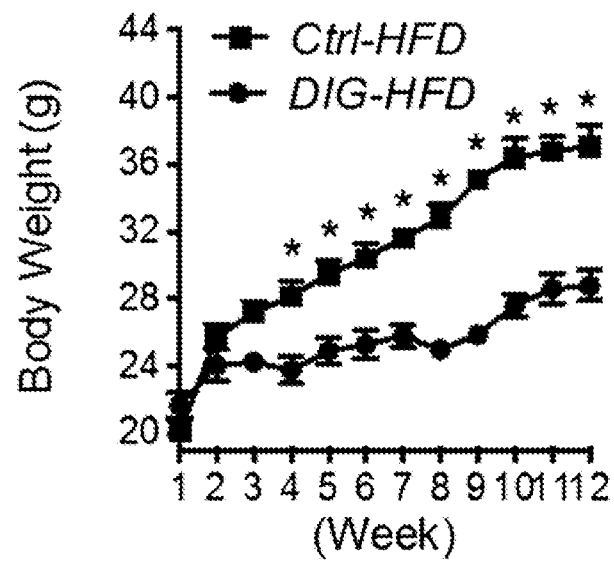
Figure 22C:
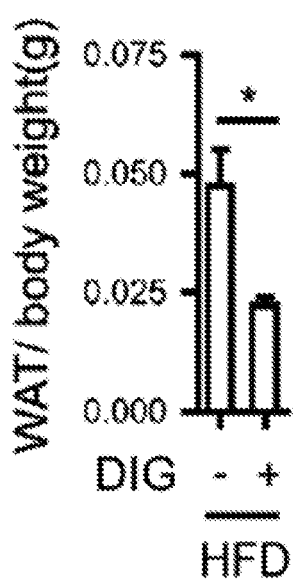
Figure 22D:
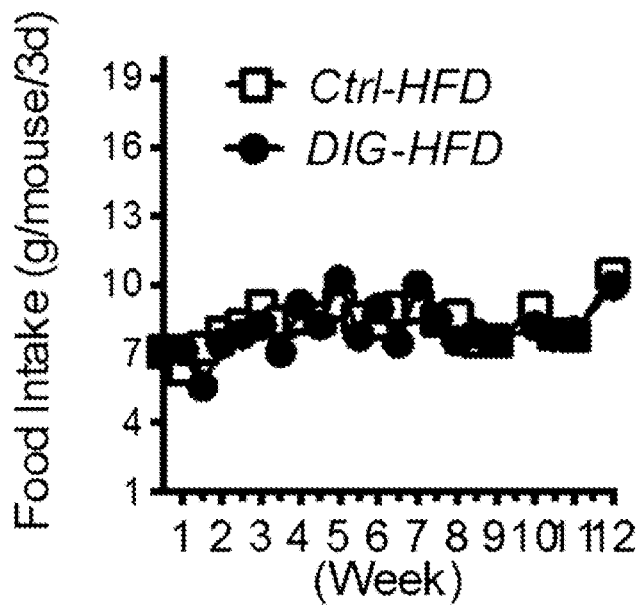
Figure 23A:
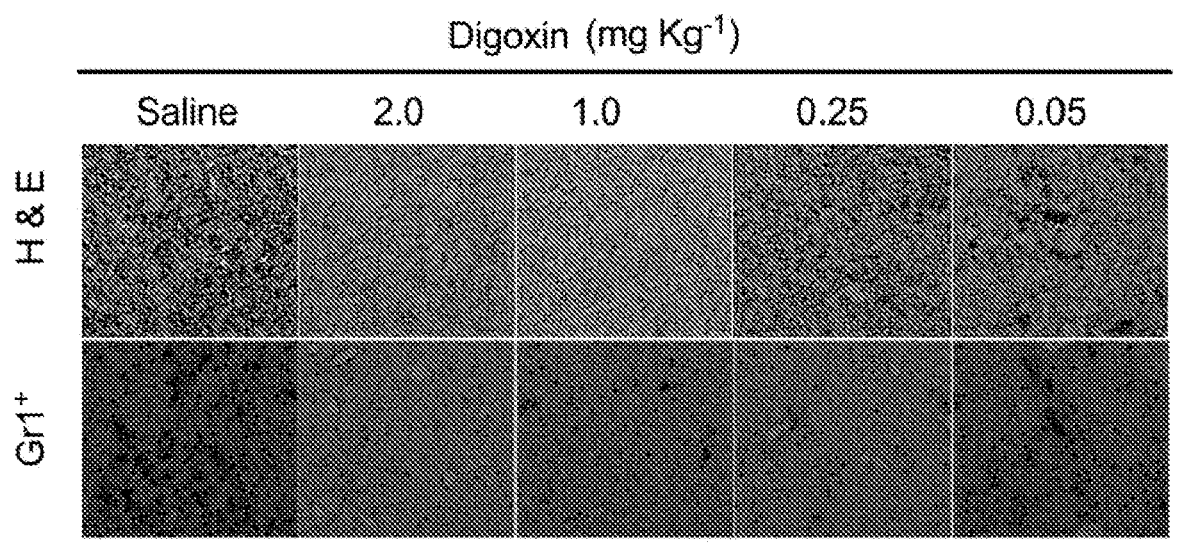
FIGS. 23A-23D illustrate the finding that digoxin protects the severity of experimental acute liver failure. Digoxin was administered intraperitoneally to C57BL/6 mice at dose level of 2, 1, 0.2, 0.05 mg/kg body weight and saline control for 1 hour, and then the mice were challenged with LPS (1 mg/kg body weight)/D-galactosamine (D-GalN) for 5 hours. The morphology of liver tissue was determined by H & E staining, and the inflammation was determined by the neutrophil infiltration of Gr-1 antibody staining Representative H & E stains (FIG. 23A, upper), and Gr-1 (FIG. 23A, lower) positive area of liver sections (original magnification ×100) from digoxin and saline control are illustrated. Graphs show quantification of injured (FIG. 23B) or Gr-1 (FIG. 23C) positive area by morphometry using Image J. *p<0.05 for each dosage of digoxin group versus saline control. The activity of the hepatic injury marker alanine transaminase (ALT) in serum level from digoxin versus saline control was measured (FIG. 23 D). All data throughout the figure are shown as the mean±SD. Statistical significance was determined by one-way ANOVA.
Figure 23B:
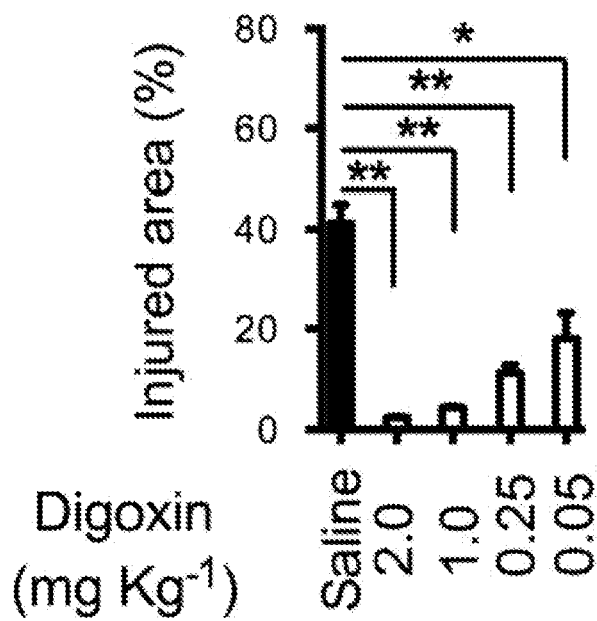
Figure 23C:
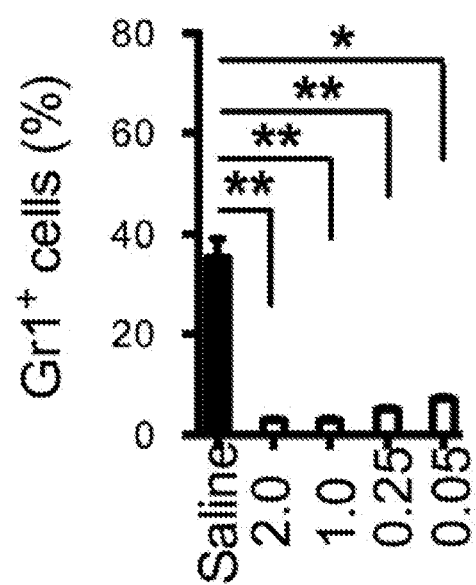
Figure 23D:
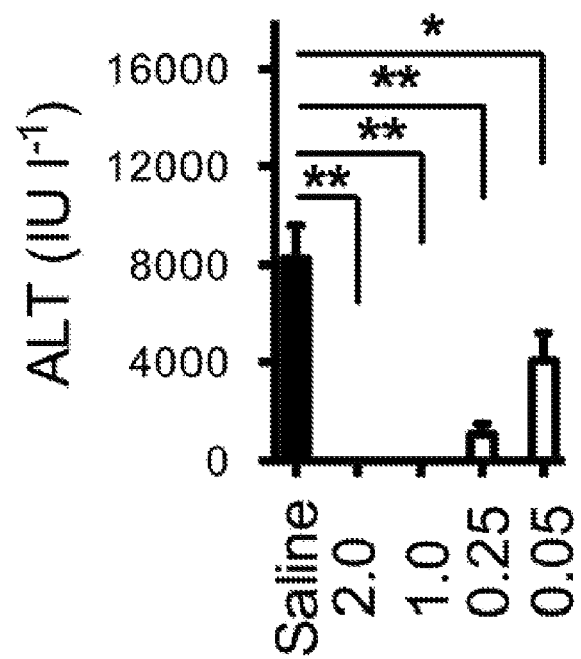
Figure 24A:
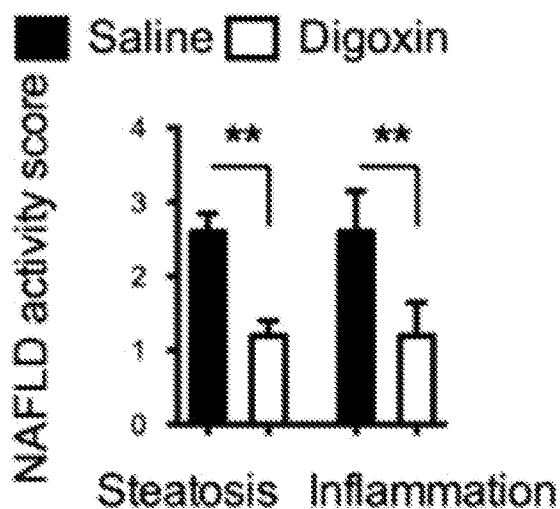
FIGS. 24A-24G illustrate the finding that digoxin limits hepatic steatosis and inflammation.
Figure 24B:
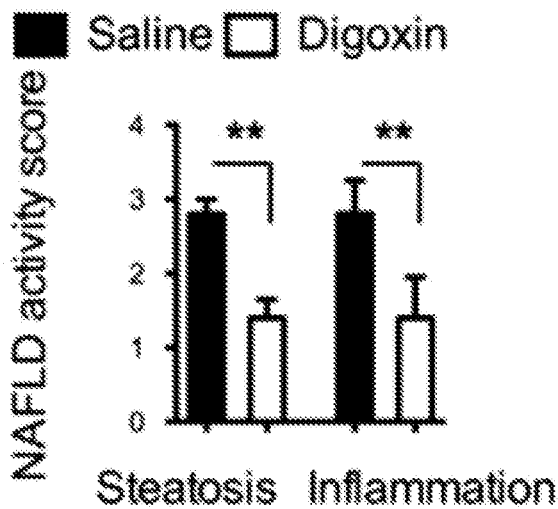
Figure 24C:
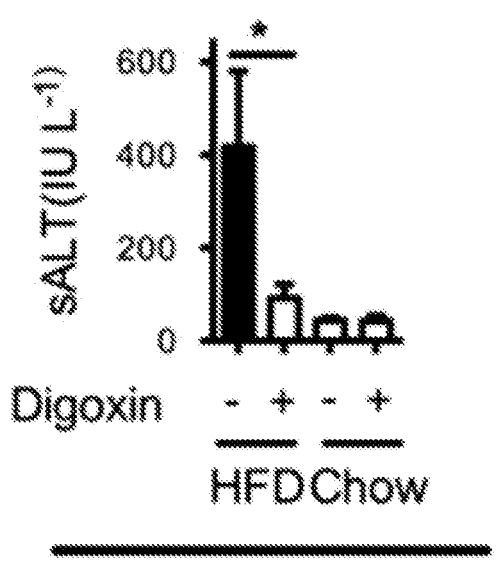
Figure 24D:
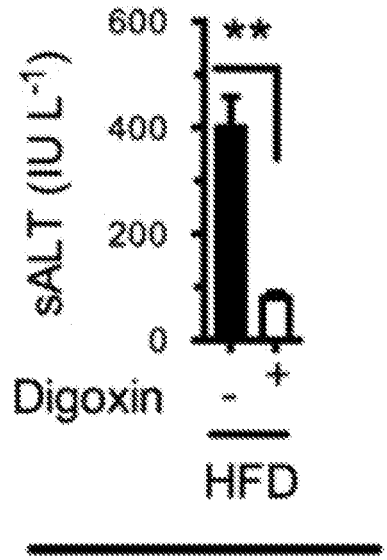
Figure 24E:
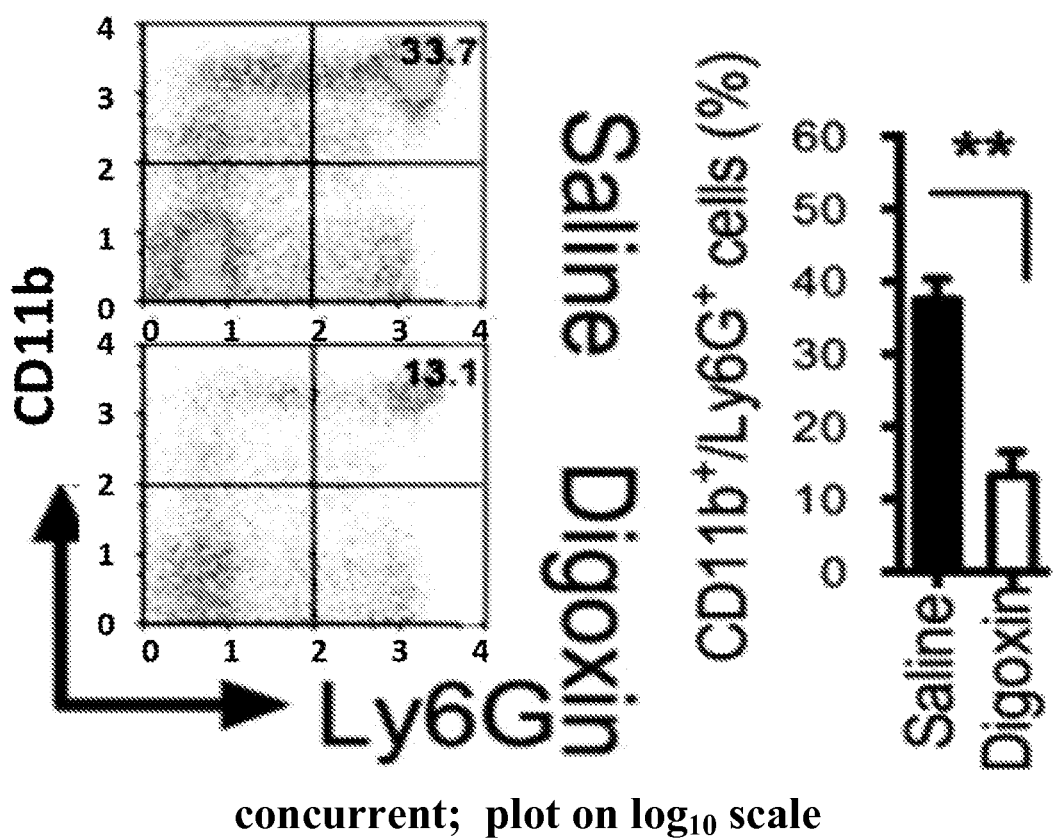
Figure 24F:
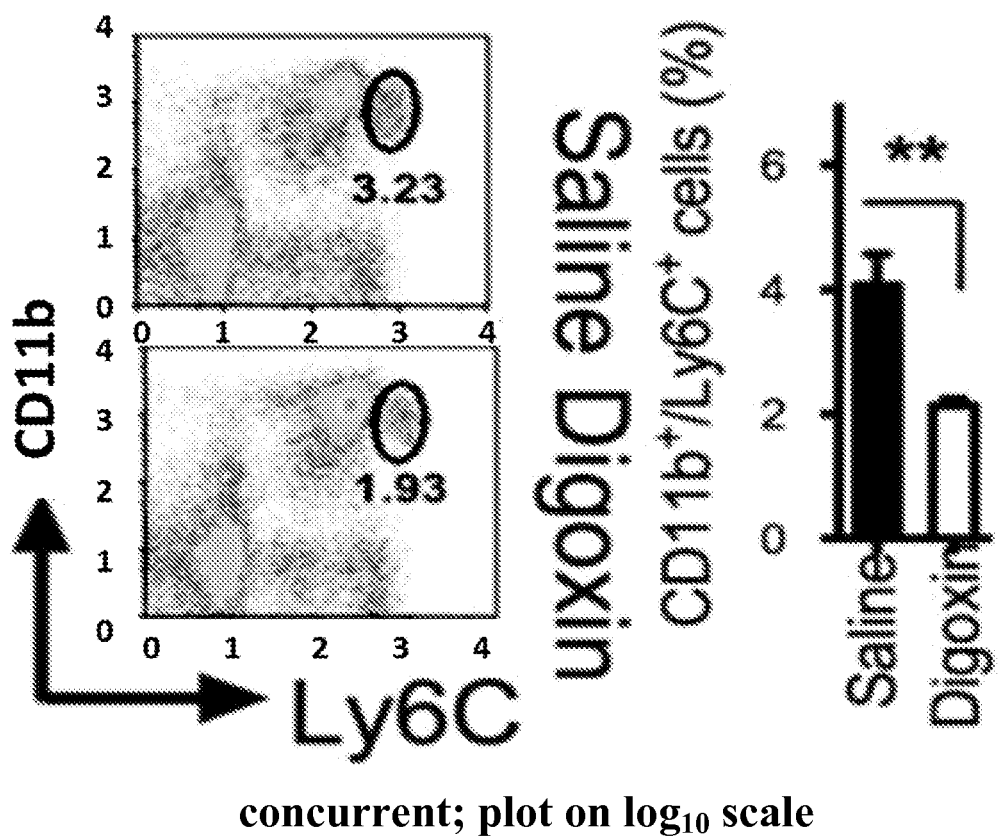
Figure 24G:
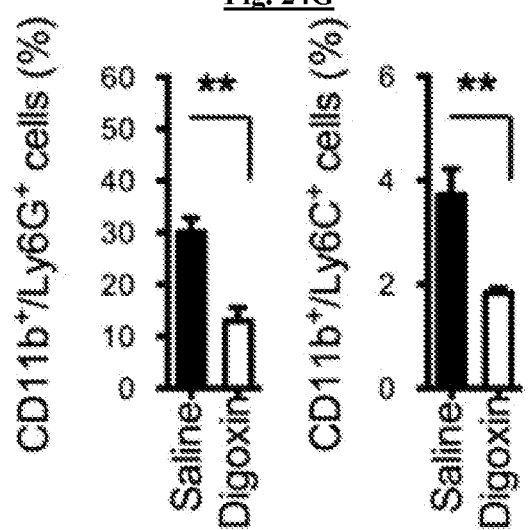
Figure 25C:
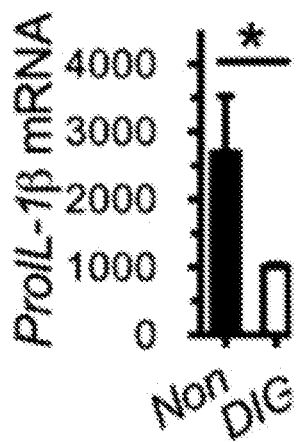
Figure 25D:
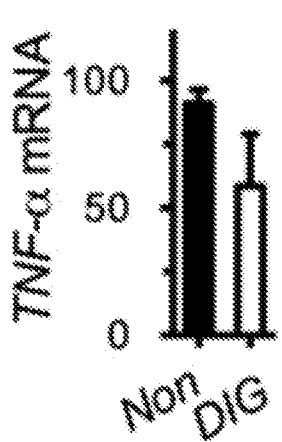
Figure 25E:
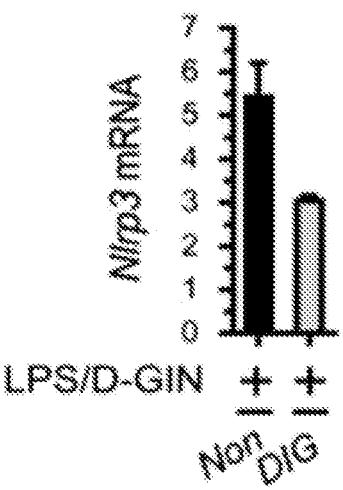
Figure 25F:
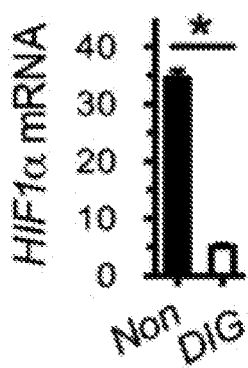
Figure 25G:
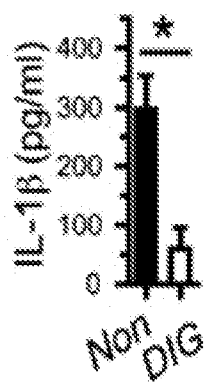
Figure 25H:
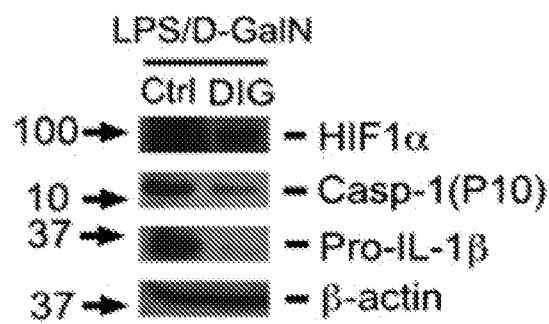
Figure 26:
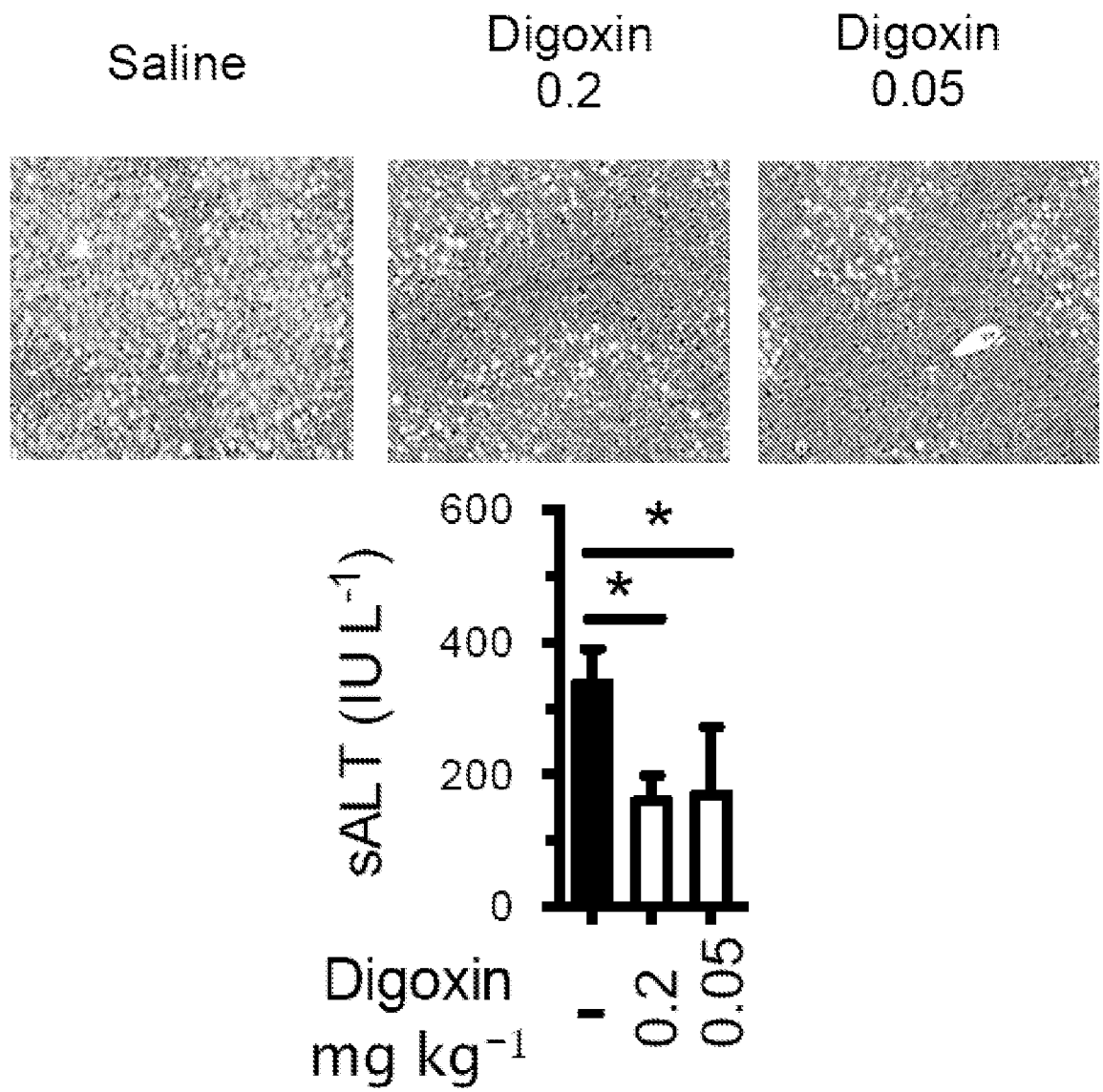
FIG. 26 illustrates the finding that digoxin limits hepatic steatosis and inflammation in a low dose-dependent manner. C57BL/6 mice were on HFD or chow concurrently with intraperitoneal injection of digoxin (0.2 and 0.05 mg/kg) and saline control twice a week for 12 weeks. The liver tissues were applied for H & E staining, and graphs show quantification of NAFLD histological activity score. Serum ALT level in digoxin versus saline control was measured. All data throughout the figure are illustrated as the mean±SD from 5 mice in each group. Statistical significance was determined by one-way ANOVA. *p<0.05, for each digoxin group versus saline control.
Figure 27:
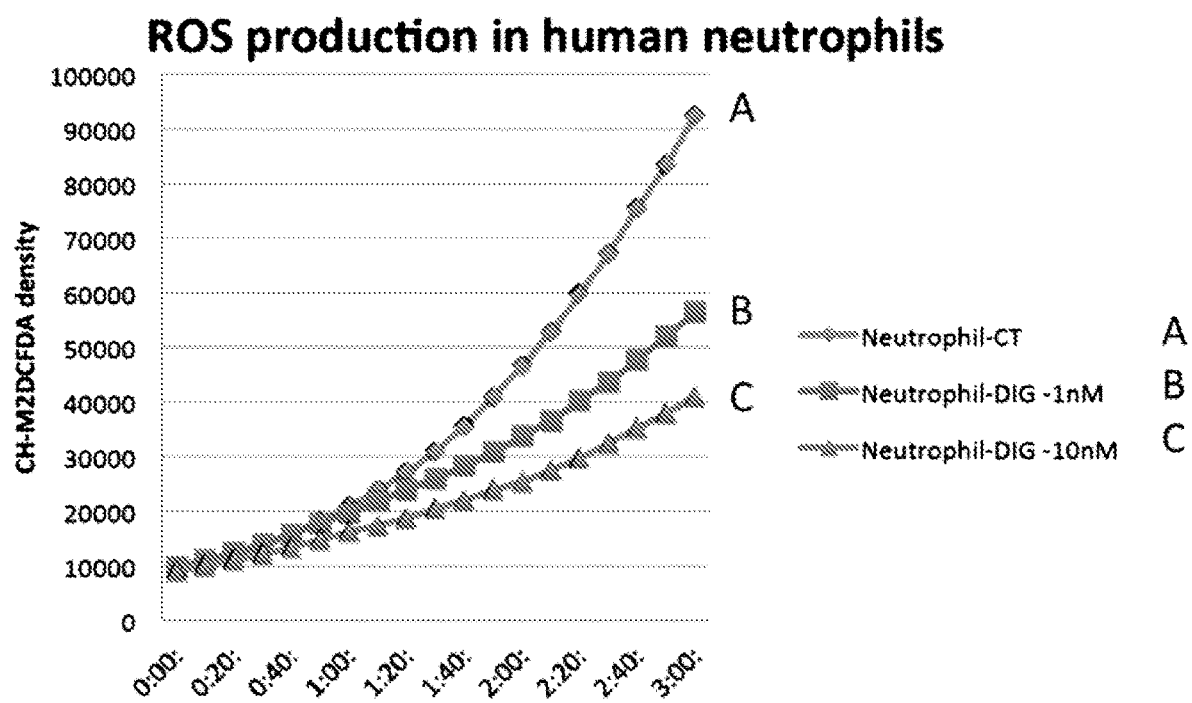
FIG. 27 comprises a graph illustrating ROS production in human neutrophils. Human neutrophils were treated with DIG as indicated dose for 3 hours and then CM-H2DCFDA (5-(and -6)-chloromethyl-2',7'-dichlorodihydrofluorescein diacetate, acetyl ester; a chloromethyl derivative of $H_2DCFDA$, useful as a fluorescent indicator for reactive oxygen species (ROS) in cells) for 20 min. The CM-H2DCFDA density was measured by plate reader kinetically.
Figure 28A:
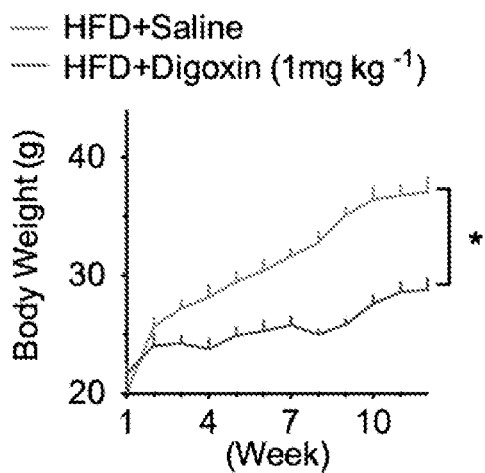
FIGS. 28A-28D comprise a set of graphs illustrating the finding that administration of digoxin changes the body weight of mice on HFD. C57BL/6 mice were on HFD or chow concurrently with digoxin as indicated dosages and saline control twice a week for 12 weeks (FIGS. 28A-28C), or on HFD for first 5 weeks and then started concurrently with digoxin (1 mg/kg) for further 3 weeks (FIG. 28D). The body weight was monitored twice a week (FIGS. 28A-28D). All data throughout the figure are shown as the mean±SD from 5 mice in each group. Statistical significance was determined. *p<0.05.
Figure 28B:
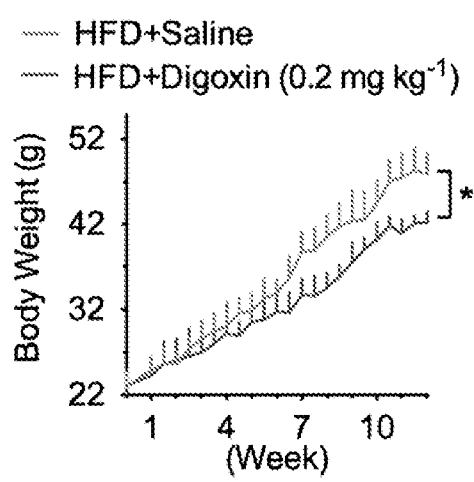
Figure 28C:
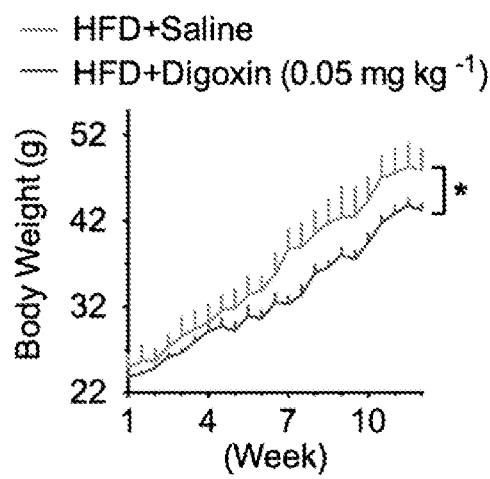
Figure 28D:
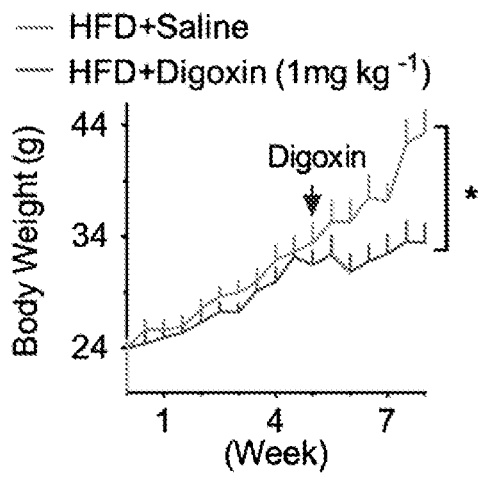
Figure 29A:
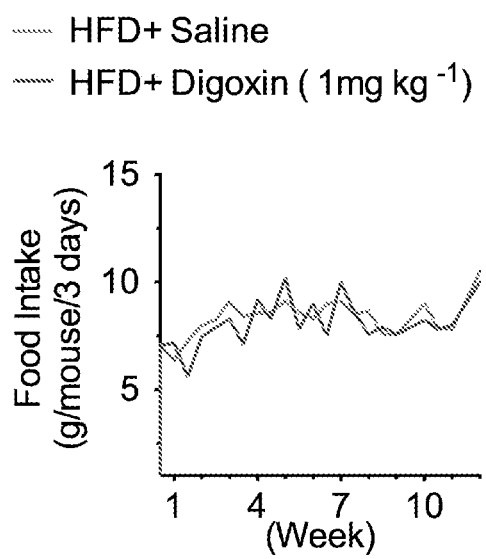
FIGS. 29A-29B comprise a set of graphs illustrating the finding that digoxin does not affect the food intake of HFD mice. C57BL/6 mice were on HFD or chow concurrently with digoxin as indicated dosages and saline control twice a week for 12 weeks (FIGS. 29A-29B). The food intake was measured twice a week (FIGS. 29A-29B). All data throughout the figure are from 5 mice in each group.
Figure 29B:
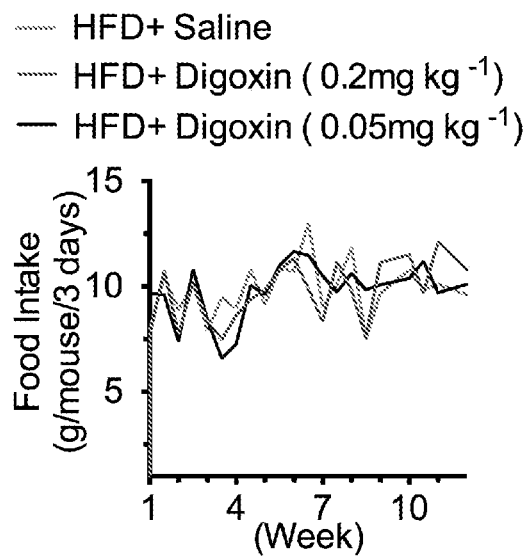
Figure 30A:
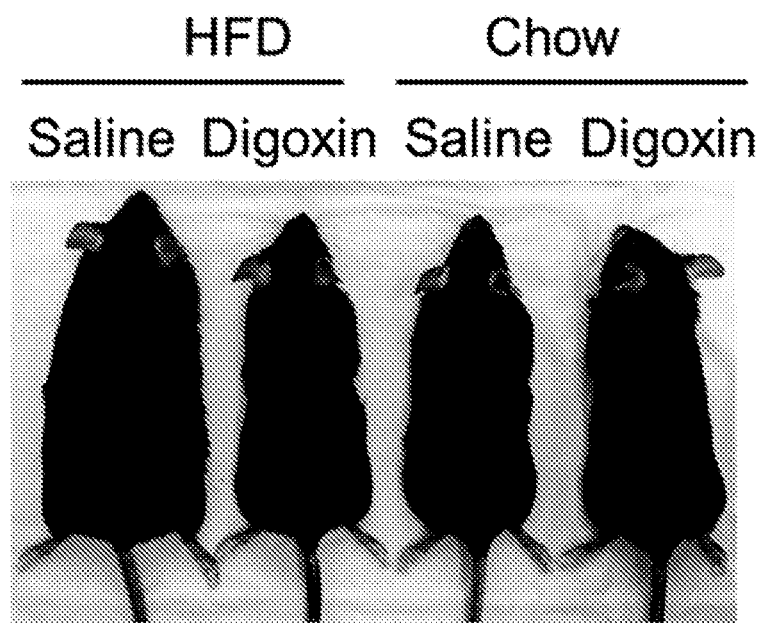
FIGS. 30A-30C comprise a set of images and graphs that illustrate the morphology of HFD mice after digoxin treatment. C57BL/6 mice were on HFD or chow concurrently with digoxin and saline control twice a week for 12 weeks (FIGS. 30A-30C). Representative morphological pictures of mouse, liver and white fat tissue are illustrated (FIGS. 30A-30B). The quantification of liver, white with weight body weight ration was measured (FIG. 30C). Statistical significance was determined. *p<0.05.
Figure 30B:
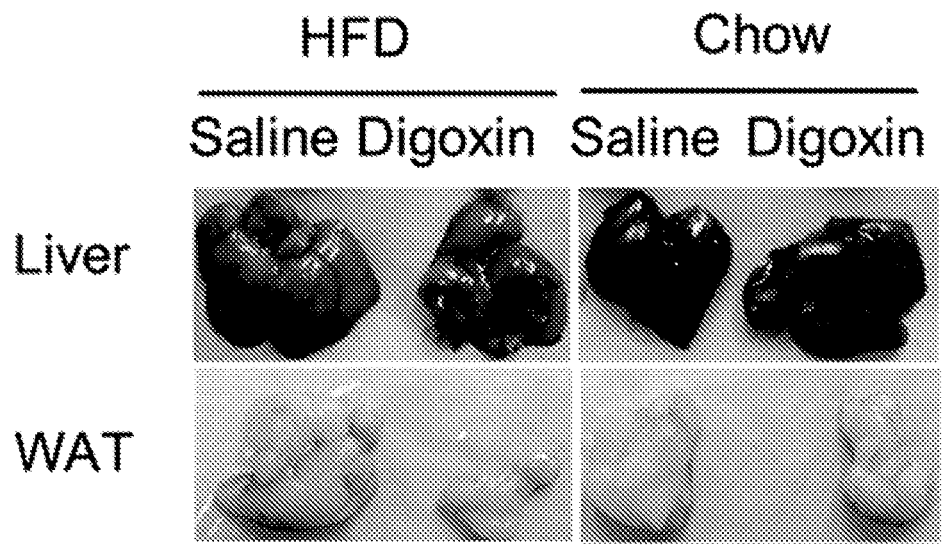
Figure 30C:
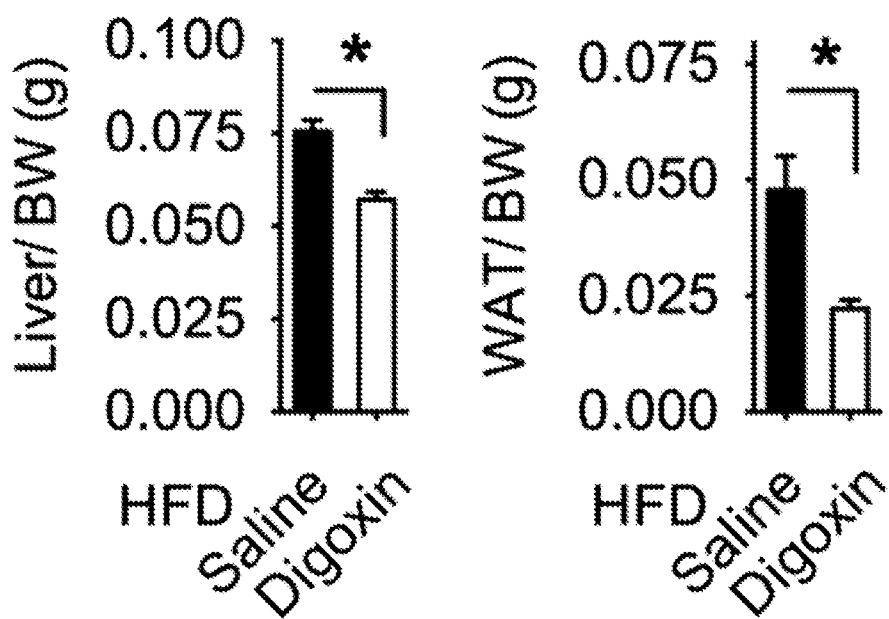
Figure 31A:
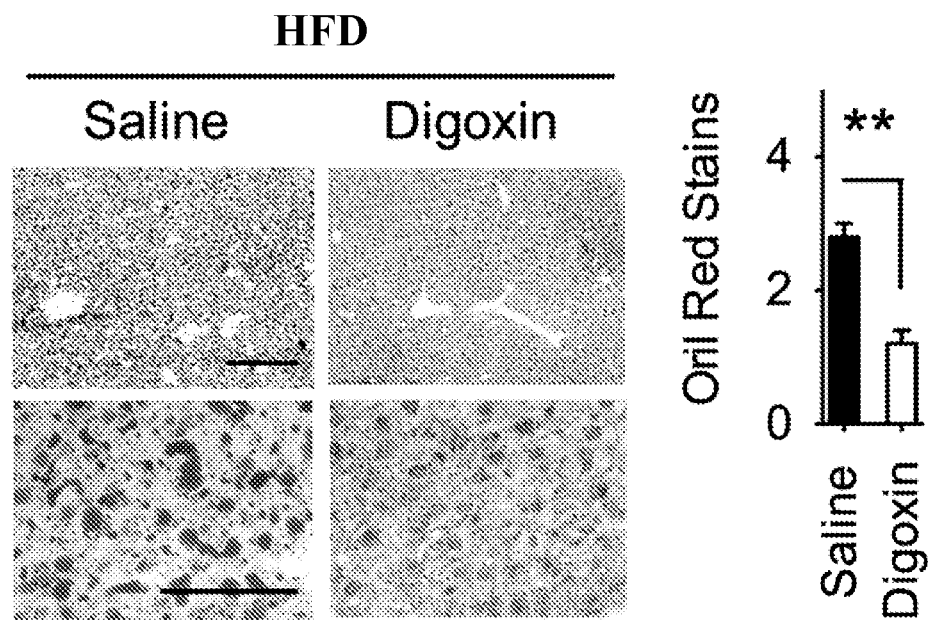
FIGS. 31A-31B comprise a set of images and graphs that illustrate the finding that digoxin reduces fat deposition. C57BL/6 mice were on HFD or chow concurrently with digoxin as digoxin (1 mg/kg) and saline control twice a week for 12 weeks (FIGS. 31A-31B). The liver section was stained with oil red. The representative stains of oil red was shown (FIG. 31A, left) and the quantification of oil red positive area was measured using Image J (FIG. 31A, right). The liver TG content was measured by ELISA (FIG. 31B). All data throughout the figure are from 5 mice in each group. Statistical significance was determined. *p<0.05.
Figure 31B:
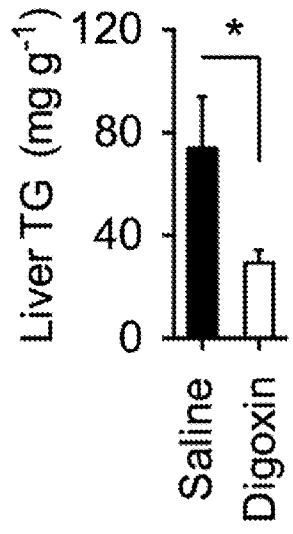

As demonstrated herein, there are additional regulatory signals, which are independent of the ligands that provide signal 1 and 2. The additional advantage of such signals is that they may provide distinct functional information. The present studies address the role of adenosine in the regulation of inflammasome activation (FIG. 17B). Extracellular adenosine concentrations are elevated in response to tissue damage, and adenosine is rapidly removed from tissues by cellular uptake and adenosine deaminase-mediated metabolism. This provides for a rapidly responsive mechanism that signals local tissue ischemia and injury. Adenosine, however, has not been considered as a DAMP (damage-associated molecular pattern molecule) because it coordinates the adaptive responses to tissue injury in many ways in addition to inflammation, and most of the immunological effects have been to reduce cytokine production.

As demonstrated herein, adenosine acting via the $A_{2A}$ receptor is a key regulator of inflammasome activity. Concentrations of adenosine found during tissue injury increase the maximal amplitude and duration of the inflammasome response. Inflammasome regulation by adenosine does not replace either signal 1 or 2, but regulates inflammasome activity initiated by a wide range of PAMPs (pathogen-associated molecular pattern molecules) and DAMPs. A cAMP/PKA/CREB/HIF-1α signaling pathway downstream $A_{2A}$ receptor is activated, and results in up-regulation of Pro-IL1β and NLRP3, and greater caspase-1 activation. In addition to regulation of inflammasome activity by pathological concentrations of adenosine, there is a requirement for physiological levels of adenosine for maximal IL-1β production. Finally, after macrophages have received signals 1 and 2, adenosine can regulate further IL-1β production, without the need for either initiating signal. This demonstrates that such cells are not simply tolerant or unresponsive to further signals, but are in a post-activation state where they have switched from an initial DAMP-driven phenotype, to a subsequent adenosine, cAMP driven phenotype.

In one aspect, the invention provides a method of treating or preventing non-alcoholic steatohepatitis (NASH) in a mammal. In another aspect, the present invention provides a method of treating or preventing a disease or disorder such as liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions in a mammal. In yet another aspect, the present invention provides a method of treating or preventing autoimmune hepatitis, primary biliary cirrhosis, and other toxic and/or inflammatory liver conditions in a mammal. In yet another aspect, the present invention provides a method of promoting weight loss in a mammal.

In certain embodiments, the method comprises administering a therapeutically effective low dose of at least one cardiac glycoside, or at least one biologically active metabolite thereof, to the mammal. In certain embodiments, the cardiac glycoside inhibits HIF-1α synthesis in the liver of the mammal. In other embodiments, the cardiac glycoside inhibits inflammation in the mammal's liver. In other embodiments, the cardiac glycoside inhibits liver steatosis in the mammal. In yet other embodiments, the cardiac glycoside reduces liver damage and/or glycolysis in the mammal. In yet other embodiments, the cardiac glycoside reduces fat-induced obesity in the mammal. In yet other embodiments, the cardiac glycoside does not have significant, deleterious and/or measurable cardiac activity in the mammal, as measured for example as occurrence of atrial tachycardia, atrioventricular block, reduction in atrioventricular node conduction, and/or increase in effective refractory period within the atrioventricular node. In certain embodiments, the mammal undergoes weight loss without concomitant reduction in food intake.

The cardiac glycosides useful within the methods of the invention include, but are not limited to, acetyldigitoxin, bufalin, cinobufagerin, convallatoxin, cymarin, digitoxigenin, digotoxin, digoxigerin, digoxin, gitoxigenin, gitoxin, marinobufagenin, nerifolin, oleandrin, ouabain, periplocymarin, peruvoside, proscillaridin A, strophanthin K and/or UNBS1450, and derivatives, prodrugs, salts or solvates thereof.

The dose of the cardiac glycoside contemplated within the invention affords a cardiac glycoside plasma level that is equal to or lower than the cardiac glycoside plasma level required to treat or prevent cardiac diseases, such as heart failure and/or atrial arrhythmia. In certain embodiments, the cardiac glycoside is digoxin and the dose useful within the methods affords a cardiac glycoside plasma level that is equal to or lower than the digoxin plasma level required to treat cardiac diseases (about 0.8 ng/ml).

In certain embodiments, the cardiac glycoside is digoxin and the dose useful within the methods affords a digoxin plasma level ranging from about 0.02 to about 0.8 ng/ml. In other embodiments, the digoxin dose useful within the methods affords a digoxin plasma level ranging from about 0.02 to about 0.05 ng/ml. In yet other embodiments, the digoxin dose useful within the methods affords a digoxin plasma level ranging from about 0.05 to about 0.1 ng/ml. In yet other embodiments, the digoxin dose useful within the methods affords a digoxin plasma level ranging from about 0.05 to about 0.15 ng/ml. In yet other embodiments, the digoxin dose useful within the methods affords a digoxin plasma level ranging from about 0.05 to about 0.2 ng/ml. In yet other embodiments, the digoxin dose useful within the methods affords a digoxin plasma level ranging from about 0.05 to about 0.25 ng/ml. In yet other embodiments, the digoxin dose useful within the methods affords a digoxin plasma level ranging from about 0.05 to about 0.3 ng/ml. In yet other embodiments, the digoxin dose useful within the methods affords a digoxin plasma level ranging from about 0.05 to about 0.35 ng/ml. In yet other embodiments, the digoxin dose useful within the methods affords a digoxin plasma level ranging from about 0.05 to about 0.4 ng/ml. In yet other embodiments, the digoxin dose useful within the methods affords a digoxin plasma level ranging from about 0.05 to about 0.45 ng/ml. In yet other embodiments, the digoxin dose useful within the methods affords a digoxin plasma level ranging from about 0.05 to about 0.5 ng/ml. In yet other embodiments, the digoxin dose useful within the methods affords a digoxin plasma level ranging from about 0.05 to about 0.55 ng/ml. In yet other embodiments, the digoxin dose useful within the methods affords a digoxin plasma level ranging from about 0.05 to about 0.6 ng/ml. In yet other embodiments, the digoxin dose useful within the methods affords a digoxin plasma level ranging from about 0.05 to about 0.65 ng/ml. In yet other embodiments, the digoxin dose useful within the methods affords a digoxin plasma level ranging from about 0.05 to about 0.7 ng/ml. In yet other embodiments, the digoxin dose useful within the methods affords a digoxin plasma level ranging from about 0.05 to about 0.75 ng/ml. In yet other embodiments, the digoxin dose useful within the methods affords a digoxin plasma level ranging from about 0.05 to about 0.8 ng/ml. In yet other embodiments, the digoxin dose useful within the methods affords a digoxin plasma level selected from the group consisting of about 0.02 ng/ml, about 0.05 ng/ml, about 0.1 ng/ml, about 0.15 ng/ml, about 0.2 ng/ml, about 0.25 ng/ml, about 0.3 ng/ml, about 0.35 ng/ml, about 0.4 ng/ml, about 0.45 ng/ml, about 0.5 ng/ml, about 0.55 ng/ml, about 0.6 ng/ml, about 0.65 ng/ml, about 0.7 ng/ml, about 0.75 ng/ml, and about 0.8 ng/ml.

In certain embodiments, the oral digoxin dose ranges from about 0.0025 mg/day to about 0.125 mg/day. In other embodiments, the oral digoxin dose ranges from about 0.0025 mg/day to about 0.0075 mg/day. In yet other embodiments, the oral digoxin dose ranges from about 0.0075 mg/day to about 0.015 mg/day. In yet other embodiments, the oral digoxin dose ranges from about 0.0075 mg/day to about 0.0225 mg/day. In yet other embodiments, the oral digoxin dose ranges from about 0.0075 mg/day to about 0.030 mg/day. In yet other embodiments, the oral digoxin dose ranges from about 0.0075 mg/day to about 0.0375 mg/day. In yet other embodiments, the oral digoxin dose ranges from about 0.0075 mg/day to about 0.045 mg/day. In yet other embodiments, the oral digoxin dose ranges from about 0.0075 mg/day to about 0.0525 mg/day. In yet other embodiments, the oral digoxin dose ranges from about 0.0075 mg/day to about 0.060 mg/day. In yet other embodiments, the oral digoxin dose ranges from about 0.0075 mg/day to about 0.0675 mg/day. In yet other embodiments, the oral digoxin dose ranges from about 0.0075 mg/day to about 0.075 mg/day. In yet other embodiments, the oral digoxin dose ranges from about 0.0075 mg/day to about 0.0825 mg/day. In yet other embodiments, the oral digoxin dose ranges from about 0.0075 mg/day to about 0.090 mg/day. In yet other embodiments, the oral digoxin dose ranges from about 0.0075 mg/day to about 0.0975 mg/day. In yet other embodiments, the oral digoxin dose ranges from about 0.0075 mg/day to about 0.105 mg/day. In yet other embodiments, the oral digoxin dose ranges from about 0.0075 mg/day to about 0.113 mg/day. In yet other embodiments, the oral digoxin dose ranges from about 0.0075 mg/day to about 0.120 mg/day.

In certain embodiments, the cardiac glycoside is administered to the mammal about once a day, about every other day, about every third day, about every fourth day, about every fifth day, about every sixth day and/or about once a week.

In certain embodiments, the mammal is further administered at least one additional agent that reduces the symptoms of, treats or prevents NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions.

In certain embodiments, the mammal is further administered at least one additional agent that reduces the symptoms of, treats or prevents autoimmune hepatitis, primary biliary cirrhosis, and other toxic and/or inflammatory liver conditions.

In certain embodiments, the mammal is further administered at least one additional agent that promotes weight loss.

In certain embodiments, the mammal is a human.

In certain embodiments, the composition is administered to the mammal by at least one route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous.

Kits

The invention includes a kit comprising at least a cardiac glycoside, an applicator, and an instructional material for use thereof.

In certain embodiments, the instructional material included in the kit comprises instructions for preventing or treating a liver disease or disorder such as NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions in a mammal. The instructional material recites the amount of, and frequency with which, the at least one cardiac glycoside should be administered to the mammal. In other embodiments, the kit further comprises at least one additional agent that treats, prevents or reduces the symptoms of a liver disease or disorder such as NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions.

In certain embodiments, the instructional material included in the kit comprises instructions for preventing or treating autoimmune hepatitis, primary biliary cirrhosis, and other toxic and/or inflammatory liver conditions in a mammal. The instructional material recites the amount of, and frequency with which, the at least one cardiac glycoside should be administered to the mammal. In other embodiments, the kit further comprises at least one additional agent that treats, prevents or reduces the symptoms of autoimmune hepatitis, primary biliary cirrhosis, and other toxic and/or inflammatory liver conditions.

In certain embodiments, the instructional material included in the kit comprises instructions for promoting weight loss. The instructional material recites the amount of, and frequency with which, the at least one cardiac glycoside should be administered to the mammal. In other embodiments, the kit further comprises at least one additional agent that promotes weight loss.

Combination Therapies

In certain embodiments, the compounds contemplated within the invention are useful within the methods of the invention in combination with at least one additional agent useful for treating or preventing a liver disease or disorder such as NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions. This additional compound may comprise compounds identified herein or compounds, e.g., commercially available compounds, known to treat, prevent or reduce the symptoms of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions.

In certain embodiments, the compounds contemplated within the invention are useful within the methods of the invention in combination with at least one additional agent useful for treating or preventing autoimmune hepatitis, primary biliary cirrhosis, and other toxic and/or inflammatory liver conditions. This additional compound may comprise compounds identified herein or compounds, e.g., commercially available compounds, known to treat, prevent or reduce the symptoms of autoimmune hepatitis, primary biliary cirrhosis, and other toxic and/or inflammatory liver conditions.

In certain embodiments, the compounds contemplated within the invention are useful within the methods of the invention in combination with at least one additional agent useful for promoting weight loss. This additional compound may comprise compounds identified herein or compounds, e.g., commercially available compounds, known to promote weight loss.

In certain embodiments, the additional agent is an anti-diabetic medication or abeticholic acid (also known as ($3\alpha,5\beta,6\alpha,7\alpha$)-6-ethyl-3,7-dihydroxycholan-24-oic acid; or (4R)-4-[(3R,5S,6R,7R,8S,9S,10S,13R,14S,17R)-6-ethyl-3,7-dihydroxy-10,13-dimethyl-2,3,4,5,6,7,8,9,11,12,14,15,16,17-tetradecahydro-1H-cyclopenta[a]phenanthren-17-yl] pentanoic acid), or derivatives, prodrugs, salts or solvates thereof.

Non-limiting examples of weight loss medications contemplated within the invention include orlistat, sibutramine, phendimetrazine tartrate, methamphetamine, IONAMIN™, phentermine, fenfluramine, dexfenfluramine, chitosan, chromium picolinate, conjugated linoleic acid, green tea extract, guar gum, hoodia, a combination of topiramate and phentermine, a combination of bupropion and zonisamide, a combination of bupropion and naltrexone, a combination of phentermine and fluoxetine, a combination of phentermine and sertraline, a combination of phentermine and citalopram, a combination of phentermine and escitalopram, or a combination of phentermine and trazodone.

Non-limiting examples of anti-diabetic medications contemplated within the invention include:

α-glucosidase inhibitors: inhibit upper GI enzymes (α-glucosidases) responsible for digesting carbohydrates, slowing absorption of glucose; also cause slower rise in postprandial blood glucose concentrations. Non-limiting examples: acarbose (Precose, Glucobay); miglitol (Glyset); voglibose (Vogseal, Volix, Basen);

lipase inhibitors: inhibit pancreatic and gastric lipases, blocking fat absorption. Non-limiting examples: orlistat (Xenical, Alli);

sulfonyl ureas: act as insulin secretagogues, triggering insulin release by interacting with the ATP-dependent potassium channel of the pancreatic β-cells. The net result is that more insulin is released at all blood glucose concentrations. They are the most commonly used drugs for treatment of patients with type 2 diabetes, but, since they trigger release of insulin itself, the combination of insulin & sulfonyl ureas is not common. Non-limiting examples: $1^{st}$ generation of sulfonyl ureas—acetohexamide, chlorpropamide (Diabinese), tolbutamide (Orinase), tolazamide; $2^{nd}$ generation of sulfonyl ureas—gliclazide (Diamicron R, Diamicron MR), glyburide or glibenclamide (Diabeta, Micronase, Glynase), glipizide (Glucotrol, Glucotrol XL), glimepiride (Amaryl), gliquidone (Glurenorm);

meglitinides: short-acting glucose-lowering drugs, acting by regulating ATP-dependent potassium channels in pancreatic β-cells like sulfonyl ureas; structurally different from sulfonylureas and act via different receptors as well. Non-limiting examples: mitiglinide (Glufast); nateglinide (Starlix); repaglinide (Prandix);

biguanides: reduce glucose release from the liver and increase glucose uptake by skeletal muscle. Metformin is the preferred initial treatment of type 2 diabetes, with good glycemic efficacy, absence of weight gain and hypoglycemia, general tolerability and low cost. The combination of metformin & insulin is generally associated with lower weight gain than insulin by itself or the combination of insulin & sulfonylureas. The triple combination of a sulfonyl urea, metformin and insulin glargine has been shown to have fewer adverse effects, fewer lipid profile problems and lower cost than the triple combination of a sulfonyl urea, metformin and rosiglitazone. Non-limiting examples: metformin (Glucophage); phenformin (DBI); buformin (Glybigid, Glybigidum);

thiazolidinediones: increase insulin sensitivity by acting on adipose, muscle and liver tissue to increase glucose utilization and decrease glucose production. The mechanism of action is not fully understood, but they seem to bind and activate one or more peroxisome proliferator-activated receptors (PPARs), regulating gene expression. Non-limiting examples: rosiglitazone (Avandia); pioglitazone (Actos); troglitazone (Rezulin); tesaglitazar (Pargluva);

pramlintide (Symlin): also known as islet amyloid polypeptide, is a synthetic analog of human amylin that slows gastric emptying and suppresses glucagon, reducing postprandial rises in blood glucose levels; approved by the FDA to lower blood sugar in type 1 diabetes patients;

incretin mimetics: these insulin secretagogues act as glucagon-like peptide-1 (GLP-1) membrane-receptor agonists. They act in a glucose-dependent manner, stimulating insulin secretion only when blood glucose levels are higher than normal. They also promote β-cell regeneration in animal models. Incretin mimetics decrease gastric motility and cause nausea. Non-limiting examples: exenatide, exedin-4 or AC2993 (Byetta); liraglutide, NN2211, or NNC 90-1170; it consists of a lipid conjugate of GLP-1, with high protein binding and a half-life of ~10 h in man;

DPP-IV inhibitors: affect glucose regulation, inhibiting degradation of GLP-1. They generally cause fewer problems with hypoglycemia or weight gain as compared to standard treatments. Non-limiting examples: sitagliptin (Januvia); sitagliptin & metformin (Janumet); vildagliptin (Galvus); vildagliptin & metformin (Eucreas);

SGLT2 inhibitors: they supress SGLT2 protein, causing excess glucose to be excreted from the body rather than reabsorbed. Non-limiting examples: dapaglifozin.

A synergistic effect may be calculated, for example, using suitable methods such as, for example, the Sigmoid-$E_{max}$ equation (Holford & Scheiner, 1981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Compositions

The invention includes a pharmaceutical composition comprising a cardiac glycoside, or a solvate, salt, prodrug or derivative thereof, wherein the cardiac glycoside comprises digoxin, whereby administration of the composition to the mammal affords a digoxin plasma level that is equal to or lower than about 0.8 ng/ml.

The invention further includes a pharmaceutical composition comprising a cardiac glycoside, or a solvate, salt, prodrug or derivative thereof, and at least one additional agent that treats, prevents or reduces the symptoms of NASH, liver injury associated with and/or caused by alcohol consumption in a mammal afflicted with NASH, alcoholic hepatitis, drug induced liver injury, primary sclerosing cholangitis, viral hepatitis, liver fibrosis, liver cirrhosis, and/or other toxic liver conditions, or a solvate, salt, prodrug or derivative thereof.

The invention further includes a pharmaceutical composition comprising a cardiac glycoside, or a solvate, salt, prodrug or derivative thereof, and at least one additional agent that treats, prevents or reduces the symptoms of autoimmune hepatitis, primary biliary cirrhosis, and other toxic and/or inflammatory liver conditions, or a solvate, salt, prodrug or derivative thereof.

The invention further includes a pharmaceutical composition comprising a cardiac glycoside, or a solvate, salt, prodrug or derivative thereof, and at least one additional agent that promotes weight loss, or a solvate, salt, prodrug or derivative thereof.

In certain embodiments, the at least one cardiac glycoside is selected from the group consisting of acetyldigitoxin, bufalin, cinobufagerin, convallatoxin, cymarin, digitoxigenin, digotoxin, digoxigerin, digoxin, gitoxigenin, gitoxin, marinobufagenin, nerifolin, oleandrin, ouabain, periplocymarin, peruvoside, proscillaridin A, strophanthin K, and UNBS1450. In other embodiments, the at least one additional agent comprises an anti-diabetic medicament or abeticholic acid. In yet other embodiments, the at least one cardiac glycoside comprises digoxin, whereby administration of the composition to the mammal affords a digoxin plasma level that is equal to or lower than about 0.8 to 2.0 ng/ml.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The therapeutically effective amount or dose of a compound of the present invention depends on the age, sex and weight of the patient, the current medical condition of the patient and the progression of a disease or disorder contemplated in the invention.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds of the invention for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In certain embodiments, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions of the invention include nasal, inhalational, topical, oral, buccal, rectal, pleural, peritoneal, vaginal, intramuscular, subcutaneous, transdermal, epidural, intratracheal, otic, intraocular, intrathecal and intravenous route administration.

Suitable compositions and dosage forms include, for example, dispersions, suspensions, solutions, syrups, granules, beads, powders, pellets, liquid sprays for nasal or oral administration, dry powder or aerosolized formulations for inhalation, and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a brain-related disease or disorder. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Materials & Methods

Animals and Macrophages:

C57BL/6 mice were purchased from the National Cancer Institute. ASC−/−, Caspase-1−/−, Nlrp3−/− and P2xr7−/− mice have been described (Rock et al., 2010, Annu Rev Immunol. 28:321-42). A2ora2a flox/flox mice and LysMcre mice were purchased from Jackson Laboratories. HIF-1a flox/flox mice were kindly provided by Dr. Ruslan M Medzhitov (Yale University). 7- to 12-week-old males with a variety of genetic manipulations were used in most experiments. The number of mice in each experimental group was chosen based on previous experience with these experimental models. Mouse peritoneal macrophages (PECs) were isolated by peritoneal lavage 3 days after intraperitoneal injection of 4% thioglycollate solution (B2551, Fluka,). Cells were plated at the density of $3 \times 10^6$ cells in 12-well dishes and non-adherent cells were removed after 3 h. Cells primed overnight with 100 ng/ml LPS or 10 ng/ml Pam3CSK4 were treated with various chemicals and followed stimulation. Cells were cultured in DMEM medium complemented with 10% FBS, penicillin/streptomycin and L-glutamine. Mouse bone marrow derived macrophages were isolated from bone marrow cells, and were differentiated for 7 days in complete RPMI-1640 medium supplemented with 2 mM L-glutamine, 100 U/ml penicillin, 100 μg/ml streptomycin, 50 μM 2-mercaptoethanol (all from Invitrogen), 10% heat-inactivated FBS and 20 ng/ml M-CSF (PeproTech). Kupffer cells (KC) were isolated by the density gradient separation of Optiprep (Sigma), and then plates were gently washed and media was replenished after seeding cells for 2 hours to raise KC purity.

Reagents:

ATP, LPS from *Salmonella minnesota* Re-595, Forskolin (cAMP analogue), SQ22536 (AC inhibitor), H-89 (PKA inhibitor), MRS1523 (A3 antagonist), adenosine, EHNA (adenosine deaminase inhibitor), 5'-(N-ethylcarboxamido) adenosine (NECA) (nonselective adenosine receptor agonist), N6,2'-O-Dibutyryladenosine 3',5'-cyclic monophosphate sodium salt (dbcAMP) and Apyrase were obtained from Sigma (St. Louis, Mo.). Adenosine deaminase was obtained from Worthington Biochemical corporation (Lakewood, N.J.). CGS21680 ($A_{2A}$ agonist), DPCPX (A1 antagonist), ZM241385 ($A_{2A}$ antagonist), and MRS 1706 (A2B antagonist) were obtained from TOCRIS (Ellisville, Mich.). Nigericin was purchased from Calbiochem, Pam3CSK4 and type B CpG oligonucleotide (ODN 1668, CpG-B) were purchased from Invivogen (San Diego, Calif.). CAY10585 (HIF-1α inhibitor) was purchased from Cayman Chemical (Ann Arbor, Mich.). TRIZOL and Dulbecco's modified Eagle's medium (DMEM) were purchased from GIBCO/Invitrogen (Carlsbad, Calif.). All reagents were of the highest quality grade commercially available. MSU crystals were produced as previously described (Martinon et al., 2009, Annu Rev Immunol. 27:229-65). Briefly, 4 mg/ml uric acid (Sigma-Aldrich, St. Louis, Mo.) was dissolved in 0.1 M borate buffer by continuously adjusting the pH to 8.0. The solution was filtered, and the crystals precipitated after 7 days were washed twice with absolute alcohol and once with acetone and air dried in a tissue culture hood before use.

Quantitative Real-Time RT-PCR:

Total RNA was extracted using TRIZOL reagent (Invitrogen), and cDNA was generated with an oligo (dT) primer and the Superscript II system (Invitrogen, USA) followed by analysis using LightCycler 480 system (Roche). q-PCR was performed for Il1b using commercial primer-probe sets (Applied Biosystems Inc.) with DNA master Mix (Roche). Expression of GAPDH was used to standardize the samples, and the results were expressed as a ratio relative to control; q-PCR was performed for tnfa, Il6, Txnip, Nlrp3, Hif1a, Timp1, using LightCycler 480 SYBR Green I master mix (Roche). Results were normalized based on the expression of β-actin. Primer sequences are listed in Table 1.

TABLE 1

Primer Sequences for qRT-PCR Experiments

| Items | Direction | Sequences |
|---|---|---|
| tnfa | Forward | aaatggcctccctctcat (SEQ ID NO: 1) |
|  | Reverse | cctccacttggtggtttg (SEQ ID NO: 2) |
| Nlrp3 | Forward | tgcaggaggaagactttgtg (SEQ ID NO: 3) |
|  | Reverse | cacgtggtccattctggtag (SEQ ID NO: 4) |
| Hif1a | Forward | ccaggccttgacaagcta (SEQ ID NO: 5) |
|  | Reverse | cgcggagaaagagacaag (SEQ ID NO: 6) |
| il6 | Forward | tgcaagagacttccatccag (SEQ ID NO: 7) |
|  | Reverse | tgaagtctectctccggact (SEQ ID NO: 8) |
| Txnip | Forward | caagagcctcagagtgcag (SEQ ID NO: 9) |
|  | Reverse | ccagggacactgacgtaga (SEQ ID NO: 10) |
| Timp1 | Forward | agtaaggcctgtagctgtgc (SEQ ID NO: 11) |
|  | Reverse | cgctggtataaggtggtctc (SEQ ID NO: 12) |

Transfection and Luciferase Reporter Assay:

THP-1 cells (Sigma-Aldrich) were transiently transfected with human IL-1β promoter (−1 to −4000) luciferase or HRE-luciferase construct in the presence of CREBΔ plasmid or empty vector. For each transfection, the total of 2.0 μg of plasmid was mixed with 200 μl of Opti-MEMO I medium (without serum and antibiotics) and 8.0 μl of X-tremeGENE HP DNA Transfection Reagent (Roche, Indianapolis, Ind.) according to the manufacturer's instructions. The mixture was incubated at room temperature for 20 minutes and added to 6-well plates containing cells and complete medium in a dropwise manner. The cells were incubated for 48 hours and harvested using reporter lysis buffer (Promega) for determination of luciferase activity. Cells were co-transfected with β-galactosidase reporter plasmid to normalize experiments for transfection efficiency. 293T cells (InvivoGen) were transiently transfected with NFkB promoter luciferase reporter construct together with *Renilla* luciferase (Rluc) control reporter vector by Lipofectamine™ 2000 reagent. All the luciferase activities were measured and normalized to Rluc or β-galactosidase activity and the normalized value with the percentage of control group was indicated.

Flow Cytometry:

Liver non-parenchymal cells were isolated and antibodies were conjugated to FITC, PE, allophycocyanin (APC) specific for CD11b (1:200, M1/70), GR-1 (1:200, RB6-8C5) (BD Biosciences-Pharmingen), Ly6-C (1:200, HK1.4) and F4/80 (1:200, BM8, eBioscience), were used. Stained cells were analyzed using FACScalibur (BD Biosciences).

Cytokine ELISA Measurements:

Primed PECs were both pulsed for 20 min with 5 mM ATP or 10 μM nigericin, and left untreated until culture supernatants were collected. Secretion of IL-1β was determined by enzyme-linked immunoabsorbent assay (ELISA; R&D Systems).

Western Blot Analysis:

Liver tissue lysates or PECs were lysed in RIPA buffer (10 mM phosphate buffer pH 7.4, 150 mM NaCl, 1% NP-40, 0.5% sodium deoxycholate, 0.1% SDS) supplemented with complete protease inhibitor cocktail (Roche) and 2 mM dithiothreitol. Lysates were resolved in 4-12% Tris-glycine gradient gels (Invitrogen) and transferred to nitrocellulose (Invitrogen) by electro-blotting. The following antibodies were used: rabbit anti-caspase-1 p10 (SC-514, Santa Cruz), goat anti-mouse IL-1β (BAF401, R&D Systems), Rabbit antimouse HIF-1α (NB100-449, Novus Biologicals, Littleton, Colo.).

Statistical Analysis:

All data were expressed as mean±SD. Student's t test was used for statistical evaluation of the results. Significance was set at $p<0.05$.

Example 1: Adenosine Stimulates IL-1β in an Inflammasome-Dependent Manner

It was tested whether adenosine can increase IL-1β production above that produced by LPS and ATP, both of which activate signals 1 and 2 respectively. The combination of LPS and ATP resulted in a high level of IL-1β production as assayed 5 hours after ATP, and this was significantly increased by adenosine (FIG. 1A). To confirm that metabolites such as inosine produced via degradation of adenosine were not responsible for the elevated IL-1β, the metabolism of adenosine from cellular sources was inhibited by using the adenosine deaminase inhibitor EHNA (erythro-9-(2-hydroxy-3-nonyl) adenine, and this also resulted in a significant increase in IL-1β production (FIG. 1A). Adenosine and EHNA in the absence of either LPS or ATP did not result in any detectable IL-1β. To determine the effect of experimentally reducing adenosine concentration, adenosine deaminase was added and resulted in a significant reduction in IL-1β release (FIG. 1A).

Figure 1B:
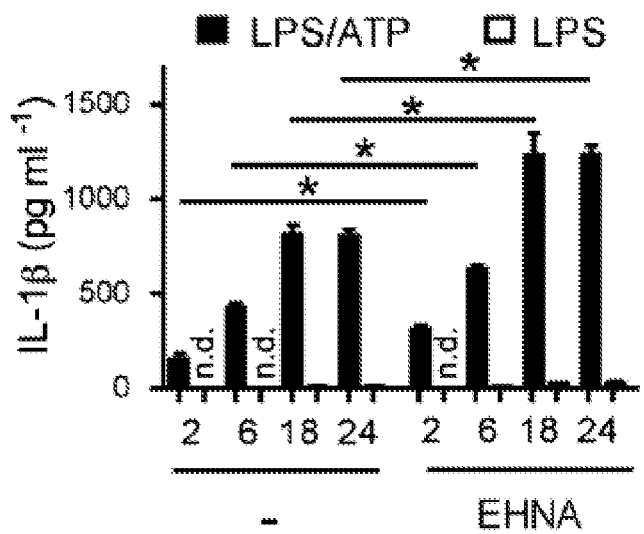
Figure 1C:
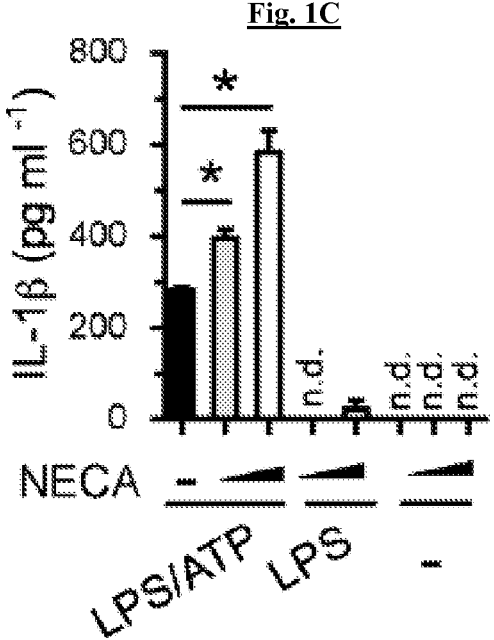
Figure 1D:
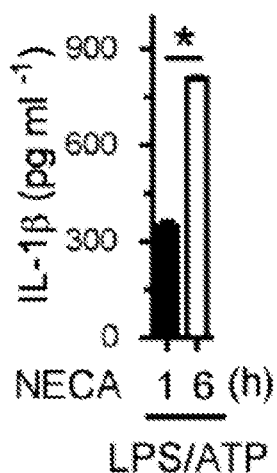
Figure 1E:
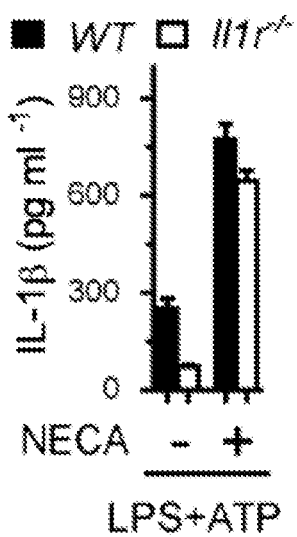
Figure 1F:
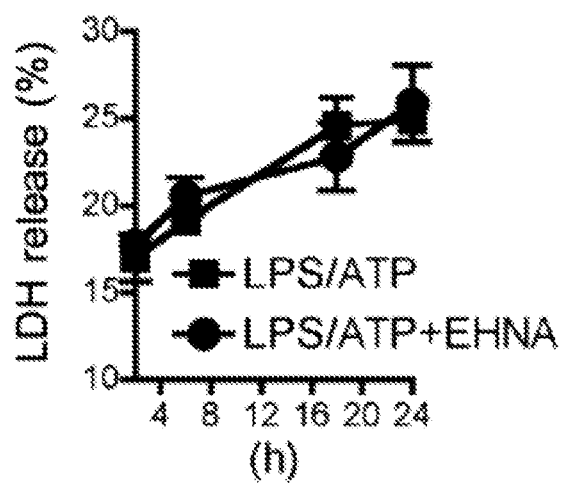
Figure 6A:
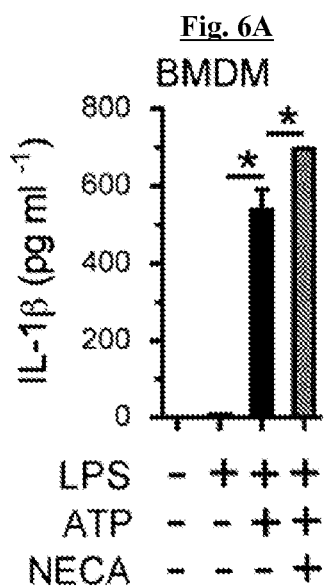
FIGS. 6A-6B illustrate the finding that bone marrow macrophages and liver Kupffer cells increase IL-1β in response to adenosine signaling.
Figure 6B:
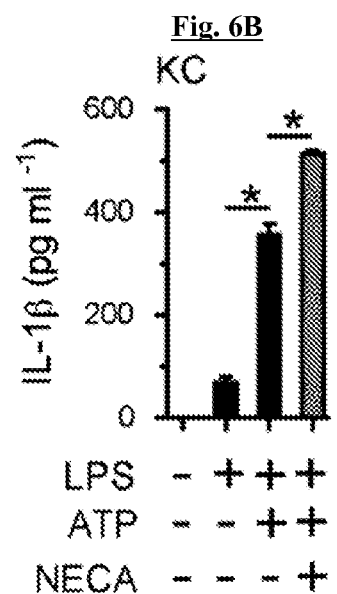

A time course demonstrated a sustained increase in IL-1β production by inhibition of adenosine deaminase (FIG. 1B). To further confirm that adenosine metabolites were not responsible for the increase in IL-1β via some other pathway, the non-degradable pan-adenosine receptor agonist NECA (5'-N-ethylcarboxamidoadenosine) was used, and also stimulated an increase in IL-1β production in LPS and ATP, and time-dependent manner (FIGS. 1C-1D). The IL-1 receptor uses the same Myd88 adaptor protein used as most TLRs and can increase IL-1β production via an autocrine loop. To rule out that NECA was enhancing this autocrine pathway, it was shown that NECA can increase IL-1β production in macrophages from wild-type and IL-1 receptor deficient mice to a similar degree (FIG. 1E). It was then tested whether this phenomenon had applicability to other types of macrophages. LPS and ATP induced stimulation of bone marrow derived macrophages and Kupffer cells resulting in production of IL-1β, and this was significantly increased by NECA (FIGS. 6A-6B). Cell death was examined by the assay of LDH (lactate dehydrogenase) release, and did not show correlation with the secretion of IL-1β in the presence or absence of EHNA, indicating that differences in macrophage survival are not the reason for the increased IL-1β production (FIG. 1F).

Figure 1G:
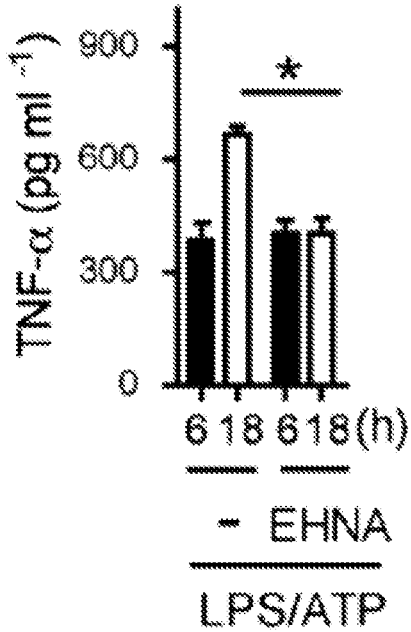
Figure 1H:
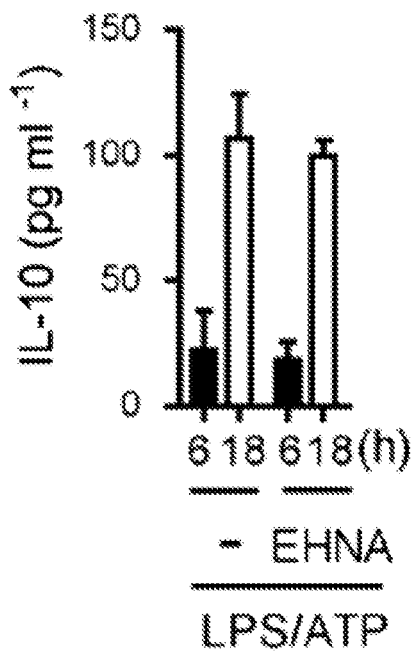
Figure 7A:
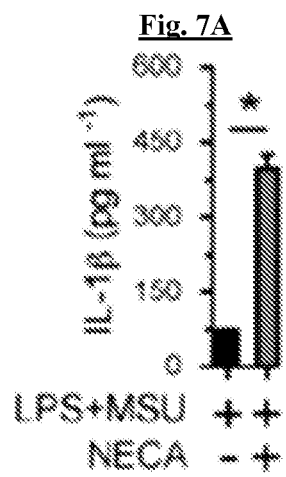
FIGS. 7A-7H illustrate the finding that adenosine signaling is important in up-regulating broad types of inflammasome stimuli.
Figure 7B:
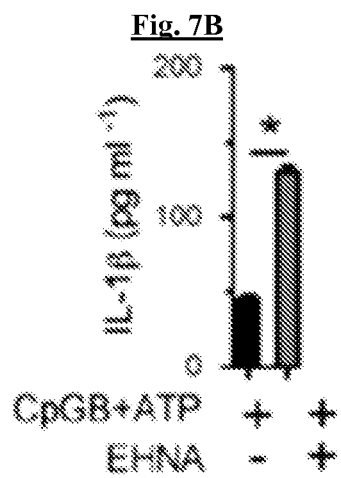
Figure 7C:
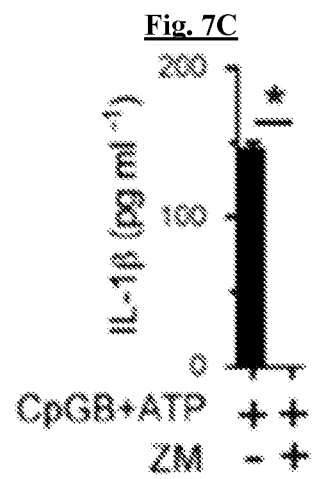
Figure 7D:
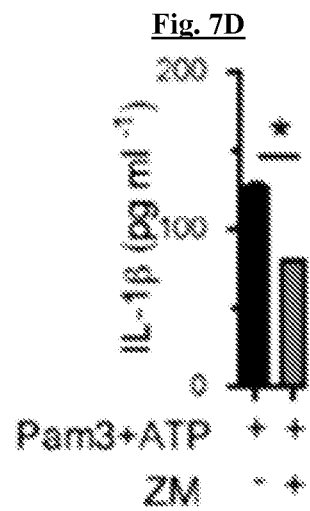
Figure 7E:
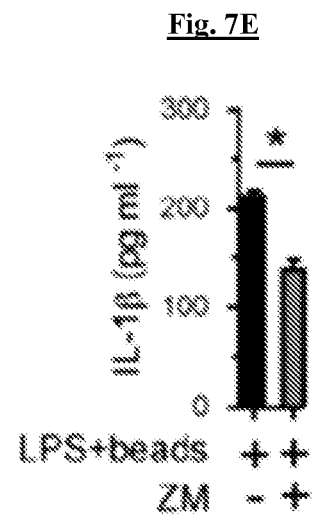
Figure 7F:
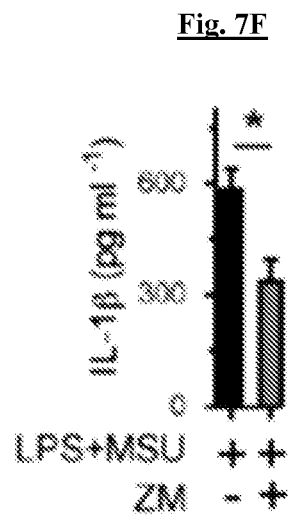
Figure 7G:
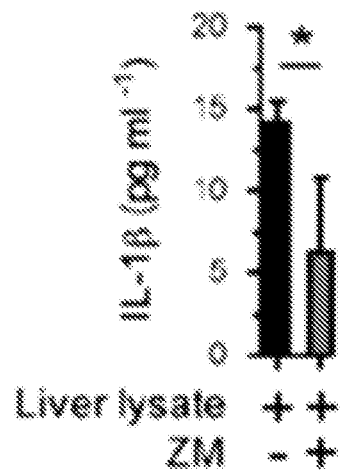

The effect of the adenosine pathway on the production of other cytokines was tested and inhibition of adenosine deaminase resulted in a reduction in the production of TNF-α, no effect on IL-10 and an increase in IFN-γ (FIGS. 1G-1I). It was then tested if the observed increase in IL-1β production was dependent on caspase-1, NLRP3, ASC and P2x7 receptor. In the absence of any of these molecules stimulation of the adenosine signal by adding the pan-adenosine receptor agonist (NECA) or inhibiting adenosine deaminase (EHNA) did not result in significant production of IL-1β by LPS and ATP (FIG. 1J). NECA also increased IL-1β production by the combination of LPS and monosodium urate (MSU) crystals (FIG. 7A). This was supported by data from different manipulations with inhibition of adenosine metabolism resulting in an increase in CpG-B and ATP induced increase in IL-1β (FIG. 7B). The reverse question of the contribution of $A_{2A}$ receptor signaling to IL-1β production was tested by using the $A_{2A}$ receptor antagonist ZM241385 in inflammasome activation by a variety of stimuli (CpG-B and ATP, Pam3 and ATP, LPS and beads, LPS and MSU and liver cell lysate) (FIGS. 7C-7G).

Figure 7H:
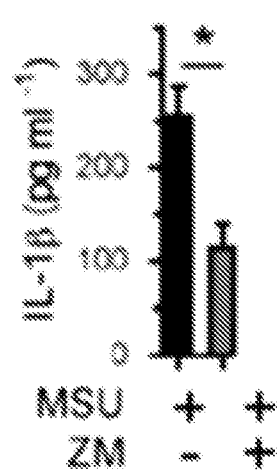

The contribution of $A_{2A}$ receptor signaling in vivo was tested in the inflammasome dependent model of MSU induced intraperitoneal sterile inflammation, which demonstrated a significant reduction in the presence of $A_{2A}$ receptor antagonism (FIG. 7H). These data show that activation of an adenosine pathway enhances the amount and duration of LPS and ATP induced IL-1β production in a NLRP3 inflammasome dependent manner, and this is not due to an IL-1β autocrine loop.

Example 2: A+ Receptor Activation Amplifies Signal 1 and 2 Pathways

Figure 2D:
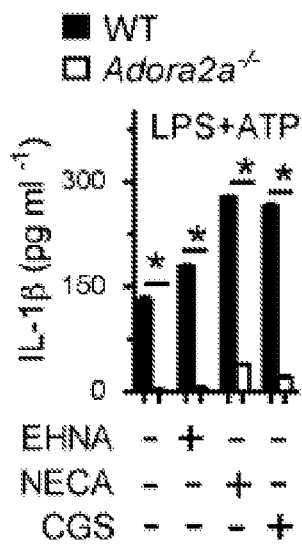
Figure 2E:
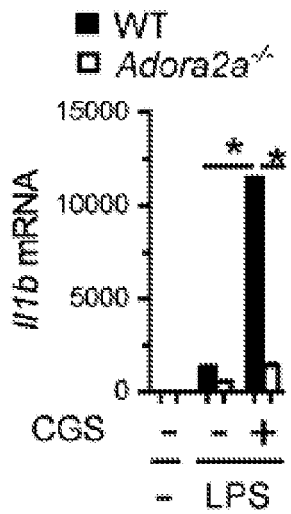
Figure 2F:
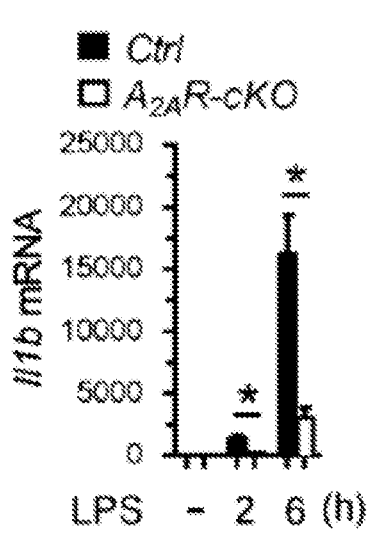
Figure 2G:
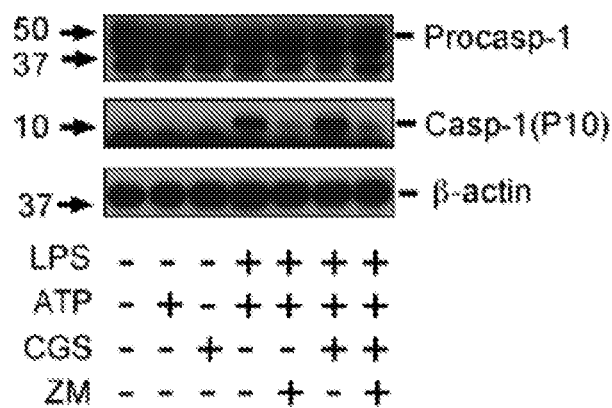
Figure 2H:
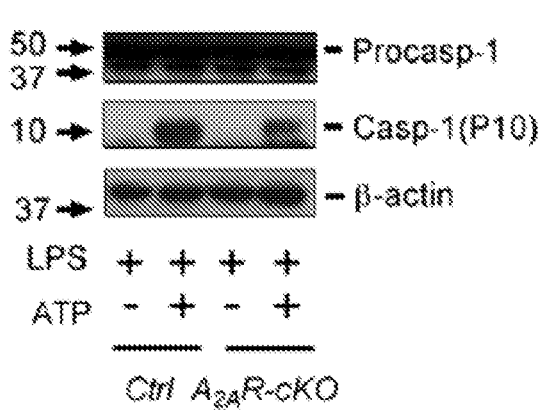
Figure 8A:
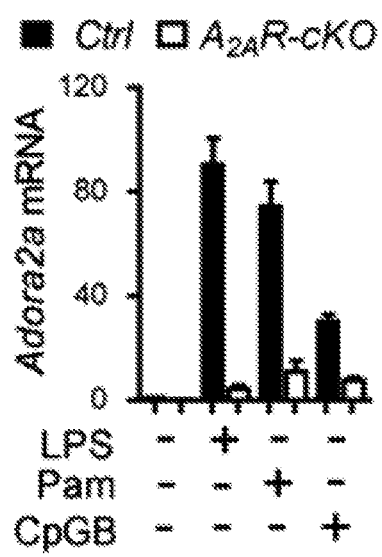
FIGS. 8A-8B illustrate the reduction in peritoneal macrophages in the expression of $A_{2A}$R and HIF-1α using the Cre/flox system.

There are four identified adenosine receptors ($A_1$, $A_{2A}$, $A_{2B}$, and $A_3$). These receptors are widely distributed and are coupled to stimulatory ($A_{2A}$, $A_{2B}$) or inhibitory ($A_1$ and $A_3$) adenylate cyclases. NECA increased IL-1β production, and this was inhibited by $A_{2A}$R antagonist (ZM241395), but not $A_1$R (DPCPX), $A_{2B}$R (MRS1706) and $A_3$R (MRS1523) specific receptor antagonists (FIG. 2A). This result was replicated by examining the ability an $A_{2A}$ receptor agonist (CGS21680) to increase IL-1β production to a comparable degree to NECA and EHNA. All of these stimuli were inhibited by ZM241395 (FIG. 2B). LDH assay indicates that the inhibitory function of ZM241395 on LPS and ATP induced IL-1β secretion was not due to its cell toxicity (FIG. 2C). To confirm the role of the $A_{2A}$ receptor, the ability of stimulation of the adenosine pathway to increase IL-1β production was tested in macrophages from $A_{2A}$ receptor deficient mice (Adora2a−/−). In the absence of $A_{2A}$ receptor there was virtually no production of IL-1β by LPS and ATP, and this was not increased by stimulation of several components related to broad activation of adenosine pathways (FIG. 2D). To identify if the increased production of IL-1β was due to adenosine induced stimulation of signal 1 and signal 2, up-regulation of Il1b gene in peritoneal macrophages from wild-type and $A_{2A}$ deficient mice in response to CGS21680 was examined (FIGS. 2E-2F). The requirement for $A_{2A}$ receptor was confirmed by a conventional strain of Adora2a knockout mice and Adora2a$^{flox/flox}$/Lysozyme M-(LysM)-Cre ($A_{2A}$RcKO) mice which had significant reduction in $A_{2A}$ receptor expression in macrophages (FIGS. 8A-8B), the macrophage from both strains had significantly less upregulation of Il1b mRNA in response to LPS (FIGS. 2E-2F). To examine the role of $A_{2A}$ receptor activation on signal 2 activated inflammasome pathway, the effect of activation of $A_{2A}$ receptor on the formation of active caspase-1 was examined. The $A_{2A}$ receptor agonist CGS21680 alone did not result in detectable active caspase-1 (FIG. 2G). In response to LPS/ATP, active caspase-1 was detected, and this was decreased by blocking $A_{2A}$ receptor with ZM241385 and increased by activating $A_{2A}$ receptor with CGS21680. The increase in active caspase-1 by CGS21680 was also inhibited by ZM241385. In addition, the clear reduction of active caspase-1 was also detected in $A_{2A}$R-cKO macrophages in response to LPS/ATP (FIG. 2H). Collectively, these data show that adenosine induced increase in LPS and ATP stimulated IL-1β production is via $A_{2A}$ receptor and is due to an increase in both signal 1 and signal 2 pathways.

Example 3: Adenosine Supersedes LPS Tolerance Via a CAMP-PKA Pathway

Figure 3A:
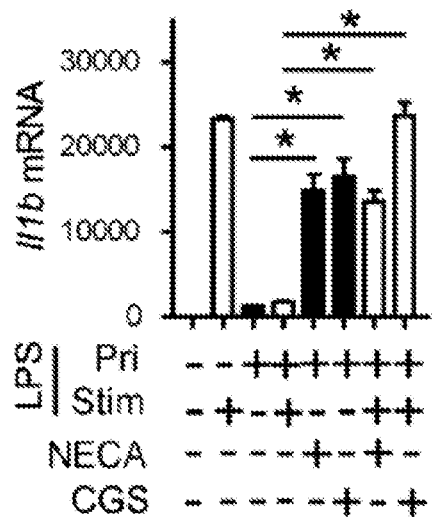
FIGS. 3A-3I illustrate the finding that adenosine supersedes LPS induced tolerance and increases IL-1β production by upregulating transcription of pro-IL-1β via cAMP-PKA pathway. PECs were used in all of the following experiments.

The demonstration that adenosine signaling can increase not just the amplitude but also the duration of IL-1β production directly impacts the well characterized phenomenon of LPS tolerance. In this phenomenon, exposure to LPS results in hypo-responsiveness to subsequent stimulation by LPS and other TLR agonists, and occurs in-part by a lack of upregulation in pro-IL-1β5. The ability of activation of the adenosine pathway to regulate Pro-IL-1β induction from PECs with previous exposure to LPS was tested. As expected, 3 hours after initial stimulation of PECs with LPS (Stim) there wa up-regulation of Il1b mRNA expression (FIG. 3A). PECs pretreated with LPS (Pri) for 16 hours had low levels of pro-IL-1β, and did not respond to a repeat stimulation with LPS (FIG. 3A). In sharp contrast to a lack of response of LPS pretreated PECs to repeat LPS stimulation, there was a dramatic increase in Il1b mRNA expression in response to either NECA or CGS21680 (FIG. 3A). These results demonstrate that after an initial signal 1, when PECs are un-responsive to further signal 1 ligands, they become highly responsive to adenosine by up-regulating Il1b. It was then tested whether this ability of adenosine to supersede LPS tolerance was true for other cytokines. Over 6 and 24 hours CGS21680 and NECA were able to increase the expression levels of Il1b, IL6, Il4 but not tnfa (FIGS. 9A-9D). Analysis of expression of relevant genes showed a consistent ability of CGS21680 and NECA to supersede LPS tolerance for tissue inhibitor of metalloproteinases-1 (TIMP-1), vascular endothelial growth factor (VEGF), and Glucose transporter 1 (GLUT-1) (FIGS. 9E-9H). In contrast, other antimicrobial gene like macrophage receptor Marco was up-regulated by adenosine signal activation, and this was found to be dependent on $A_{2A}$ and IL-1 receptor signaling (FIGS. 10A-10F).

Figure 3B:
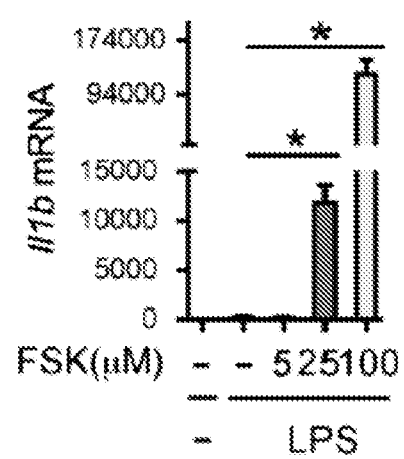
Figure 3C:
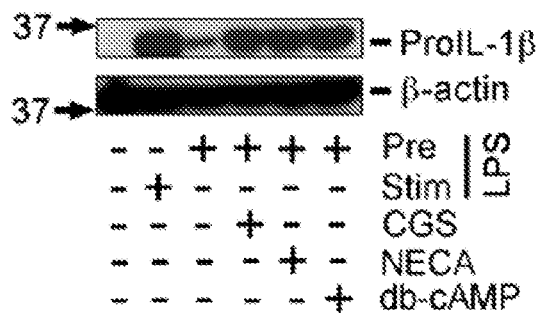
Figure 3D:
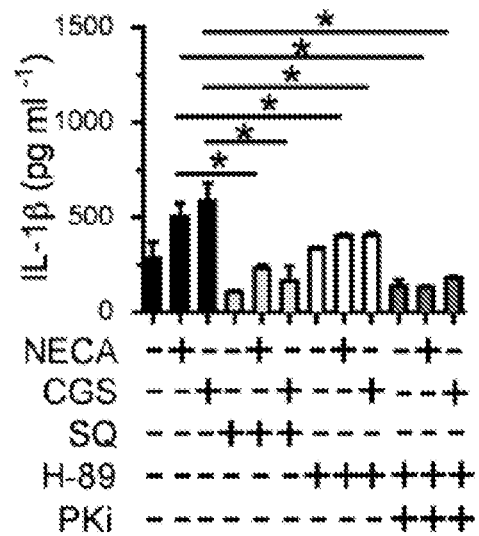
Figure 3E:
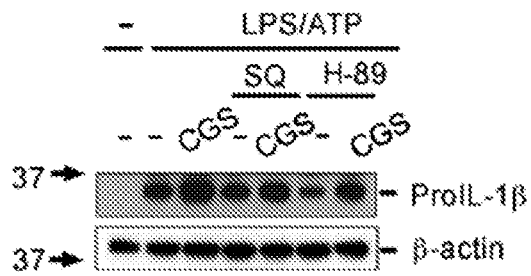
Figure 3F:
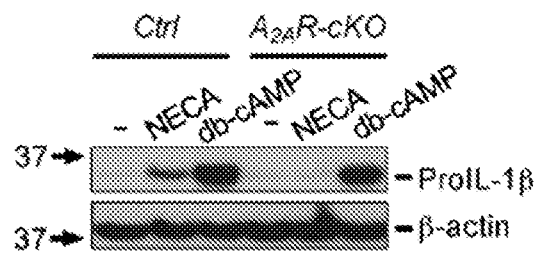

The $A_{2A}$ receptor is coupled to a stimulatory adenylate cyclase, which results in upregulation of cAMP and activation of protein kinase A (PKA). To test this pathway, the adenylate cyclase activator forskolin, which induced the induction of Il1b gene in a dose dependent manner, was used (FIG. 3B). This was confirmed by directly using a stable analogue of cAMP (db-cAMP), which along with NECA and CGS induced up-regulation of Pro-IL-1β (FIG. 3C). To test the requirement for the edentate cyclase/cAMP/PKA pathway on $A_{2A}$ receptor signal induced IL-1β production, an adenylate cyclase inhibitor (SQ22536) was tested and was able to block the increase in IL-1β induced by CGS21680 and EHNA (FIG. 3D). The requirement of PKA downstream of cAMP activation was tested using the specific inhibitors of H-89 and PKI 14-22 amide (PKi). PKA inhibition significantly reduced the IL-1β production in response to NECA and CGS21680 (FIG. 3D). This was confirmed for pro-IL-1β protein level by western blot (FIG. 3E). The lack of response in cells from A2A receptor deficient mice (FIG. 2e) was not due to developmental effects, as demonstrated by testing the ability of db-cAMP to increase pro-IL1β protein levels in $A_{2A}$R-cKO mice (FIG. 3F).

Figure 3G:
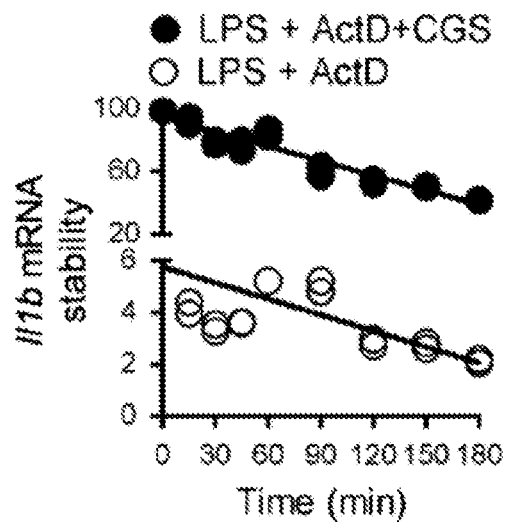
Figure 3H:
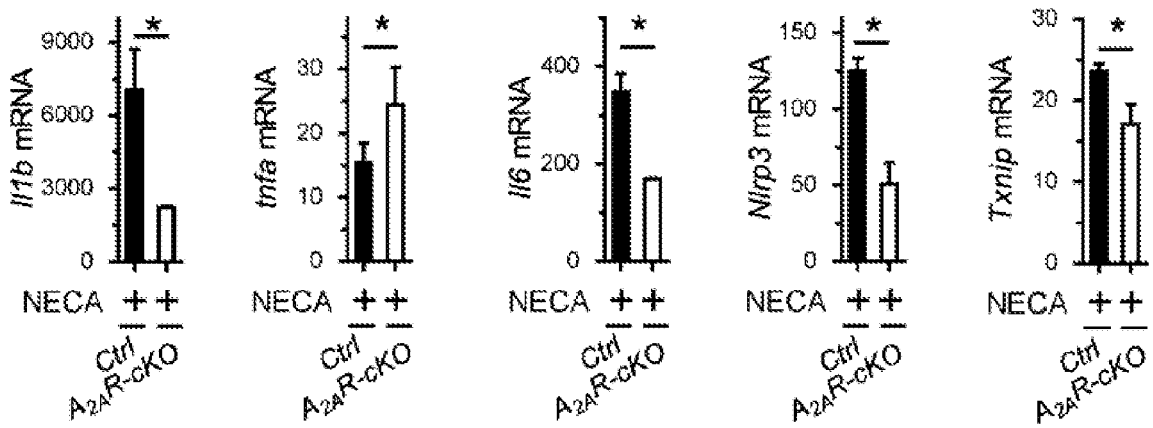
Figure 3I:
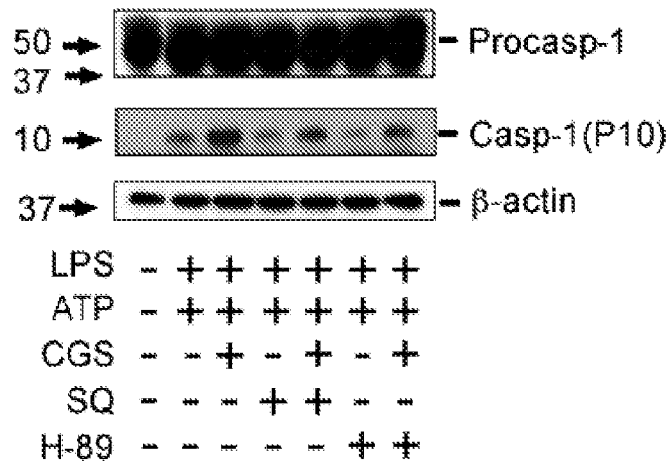

To determine if the greater amounts of Pro-IL-1β transcripts after $A_{2A}$ receptor activation were due to increased transcript stability, actinomycin D was used to inhibit transcription, and examined the effect of CGS21680 on the loss of Pro-IL-1β transcript. The rate of loss of Il1b mRNA expression was identical showing that CGS did not affect transcript stability (FIG. 3G). To confirm the role of $A_{2A}$ receptor in increasing TLR induced Pro-IL-1β upregulation, the response of macrophages from $A_{2A}$ receptor deficient mice was tested. In the absence of $A_{2A}$ receptor there was minimal increase in LPS induced up-regulation of Il1b mRNA expression (FIG. 3H). The role of adenosine signaling and $A_{2A}$ receptor in the changes associated with a number of cytokine and inflammasome related transcripts was tested (FIG. 3H). In contrast to decreased Il1b and Il6 mRNA in $A_{2A}$ receptor deficient cells, there was a higher level of tnfa. Of interest there were also lower levels of Nlrp3 and Txnip transcripts in $A_{2A}$ receptor deficient cells. It was further tested whether the adenylate cyclase/cAMP/PKA pathway was also required for the $A_{2A}$ receptor induced increase in active caspase-1. This was the case, with the CGS21680 induced up-regulation in LPS/ATP induced active caspase-1 being reduced by SQ22536 and H-89 (FIG. 3I). In contrast with these findings, under non-LPS tolerogenic condition, adenosine-cAMP signaling did not show increase in IL1β secretion by inflammasome activation indicating distinct role of adenosine in deriving IL-1β production (FIGS. 11A-11D). Collectively, these data show that adenosine signaling can supersede LPS tolerance of signal 1 via the A2A receptor, and does so via an adenylate cyclase/cAMP/PKA mediated pathway.

Example 4: Adenosine Induces Pro-IL-1β Via CREB and HIF-1α

Figure 4A:
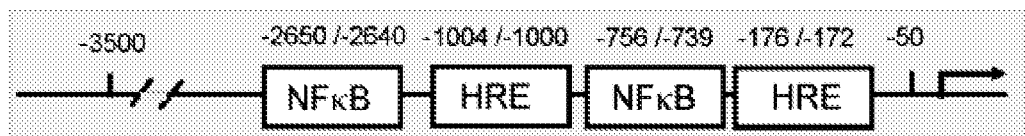
FIGS. 4A-4H illustrate the finding that adenosine mediates increase in pro-IL-1β via a HIF-1α-dependent pathway.
Figure 4B:
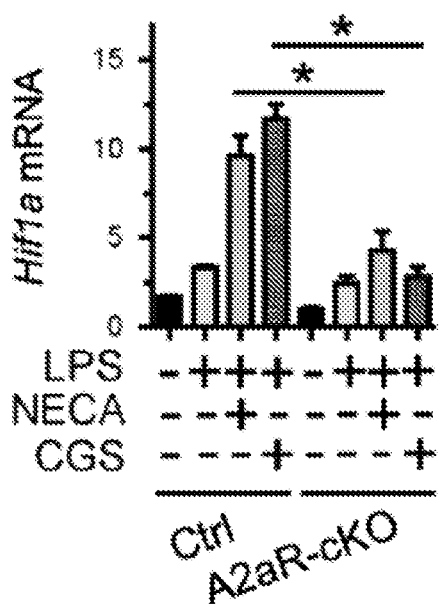
Figure 4C:
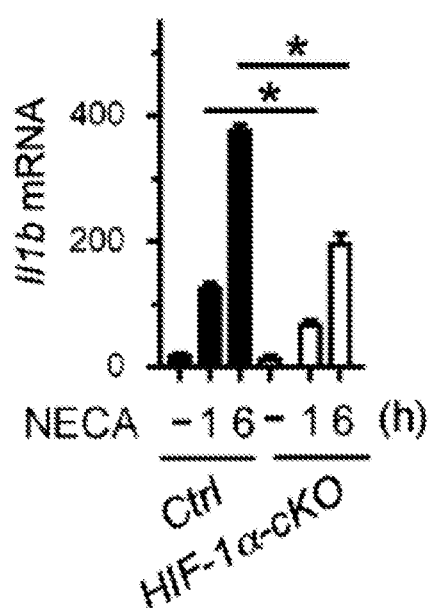
Figure 8B:
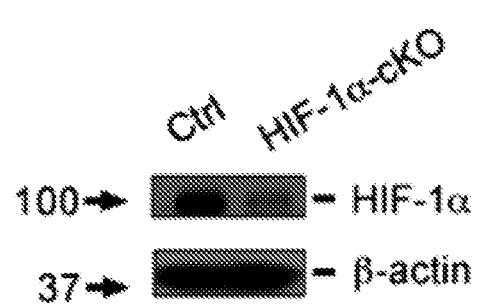
Figure 10D:
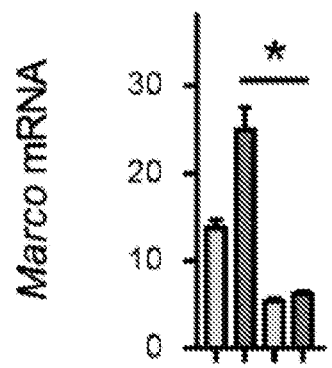
Figure 10E:
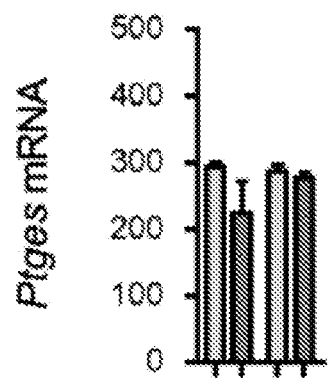
Figure 10F:
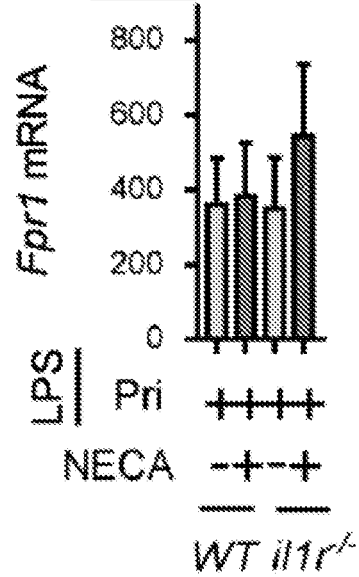
Figure 11A:
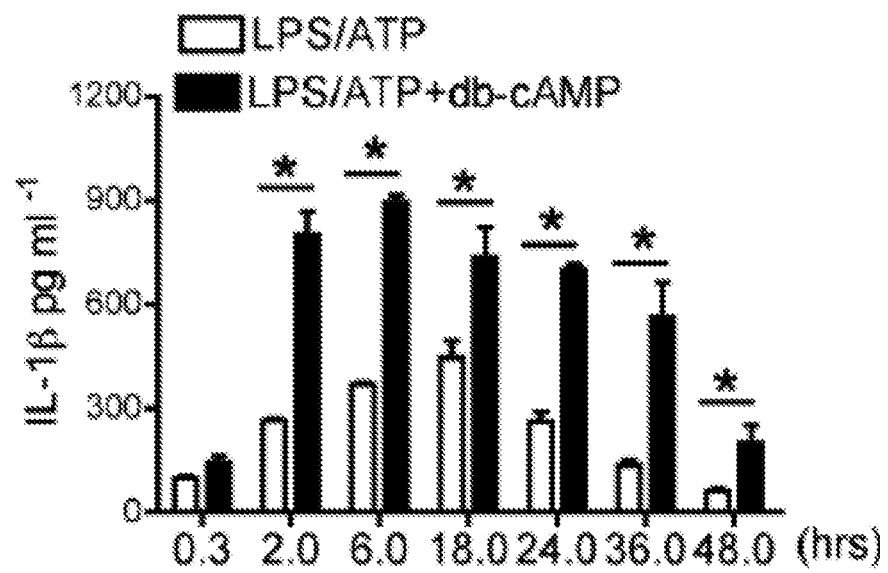
FIGS. 11A-11D illustrate the difference of IL-1β secretion by cAMP signaling under LPS tolerogenic and non-tolerogenic condition in inflammasome activity. In 16 hours LPS primed (FIG. 11A) or 3 hours primed BMDM (FIG. 11B) were treated with db-cAMP (200 μM) for 1 hour, and then pulsed with ATP. The cell supernatants were collected as indicated time-course after ATP pulsing for IL-1β assay by ELISA.
Figure 11B:
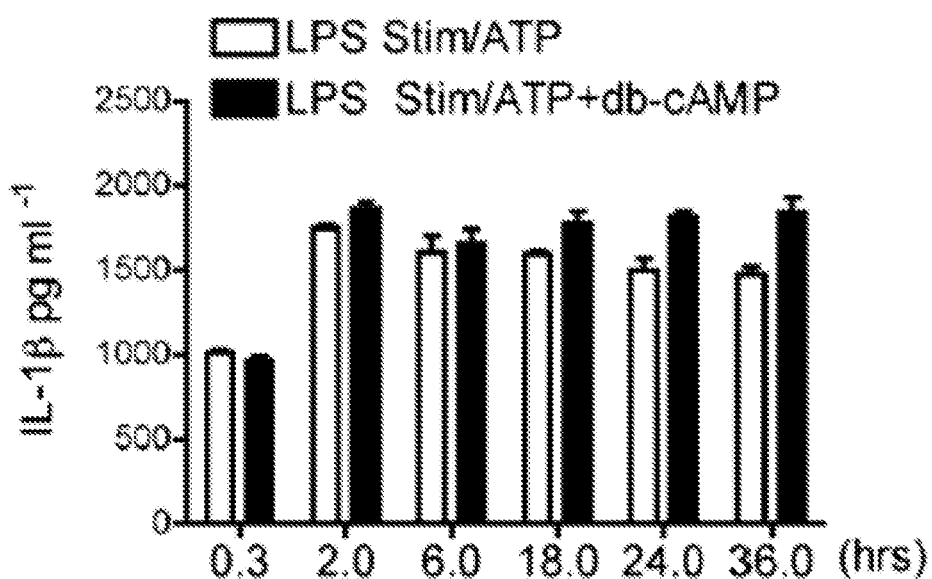
Figure 11C:
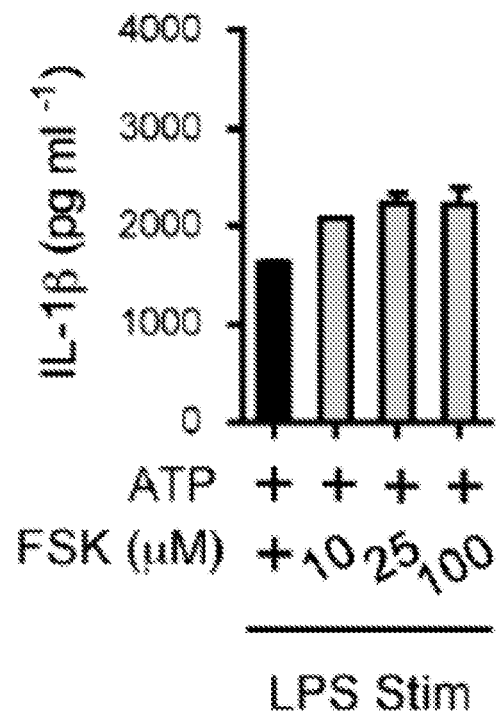
Figure 11D:
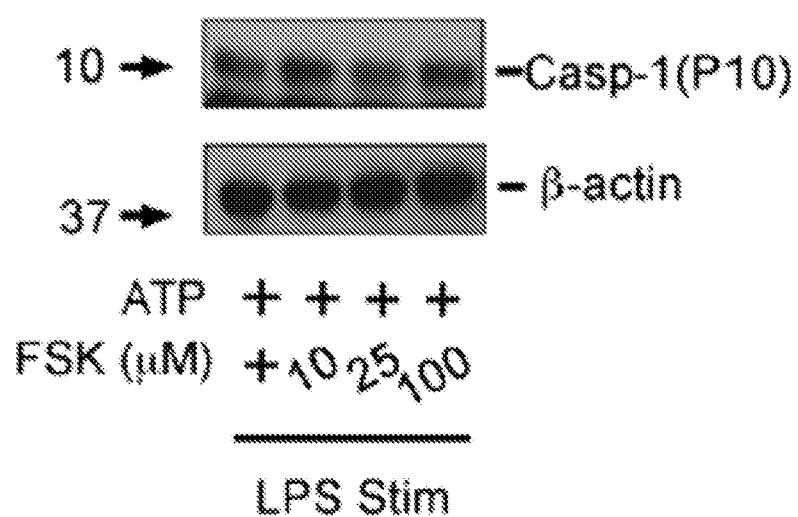
Figure 12A:
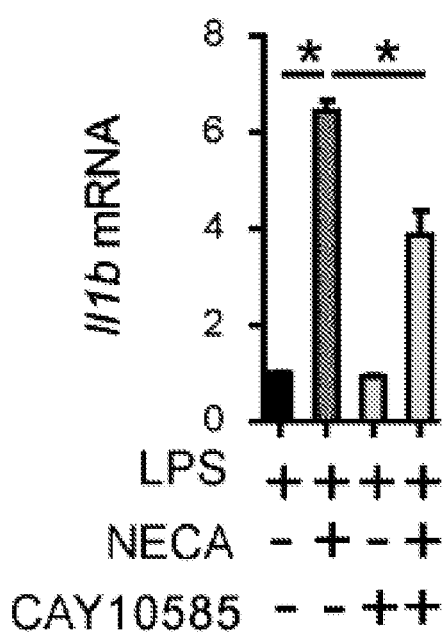
FIGS. 12A-12D illustrate the finding that HIF-1α is required for adenosine-induced up-regulation of Pro-IL-1β and NLRP3.
Figure 12B:
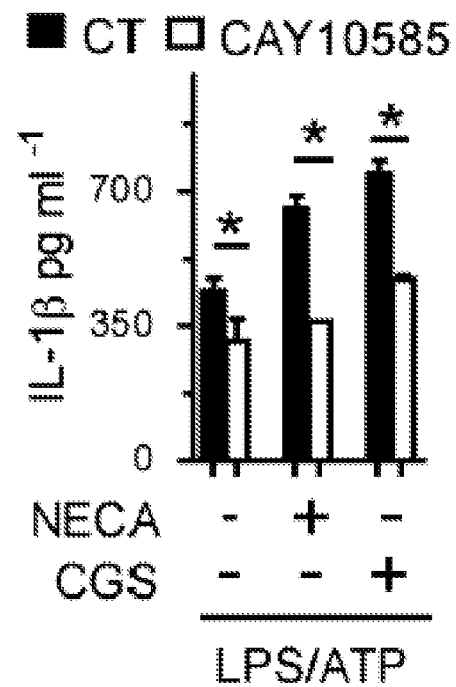
Figure 12C:
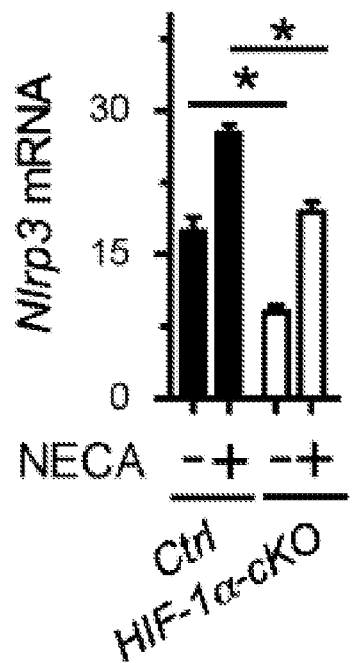
Figure 12D:
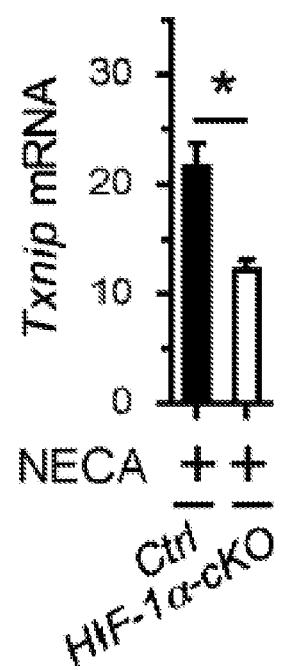

To understand the link between PKA activation and Pro-IL1β up-regulation, HIF-1α response elements were identified in the human and mouse Il1b promoter (FIG. 4A). This suggested that HIF-1α activation may be a central step in upregulating Pro-IL-1β. Studies showed that $A_{2A}$ receptor activation resulted in up-regulation of Hif1a mRNA (FIG. 4B). The HIF-1α inhibitor CAY10585 was able to significantly decrease adenosine agonist induced Il1b expression and IL-1β production (FIGS. 12A-12B). To specifically test the role of HIF-1α in $A_{2A}$ receptor activation induced upregulation of Il1b mRNA, HIF-1α$^{flox/flox}$/Lysozyme M (LysM)-Cre mice (HIF-1α-cKO) were generated, and high deletion efficiency was demonstrated in bone marrow derived macrophages (FIG. 8B). LPS primed HIF-1α-cKO macrophages had significantly less $A_{2A}$ receptor stimulation induced up-regulation of Il1b than wild-type macrophages (FIG. 4C). LPS primed HIF-1α-cKO macrophages had significantly less $A_{2A}$ receptor stimulation induced up-regulation of Nlrp3 and Txnip mRNA than wild-type macrophages (FIGS. 12C-12D).

Figure 4D:
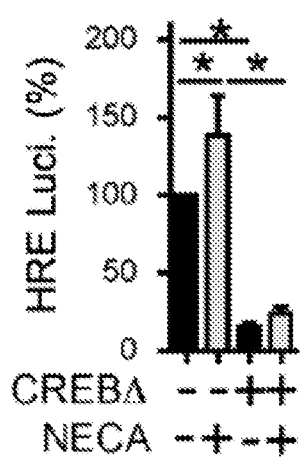
Figure 4E:
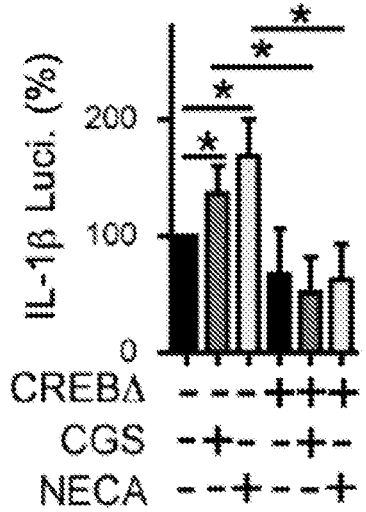
Figure 4F:
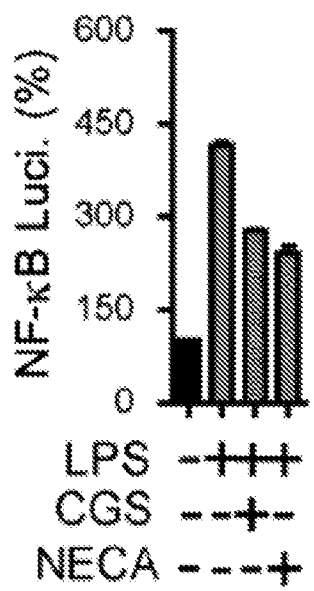
Figure 4G:
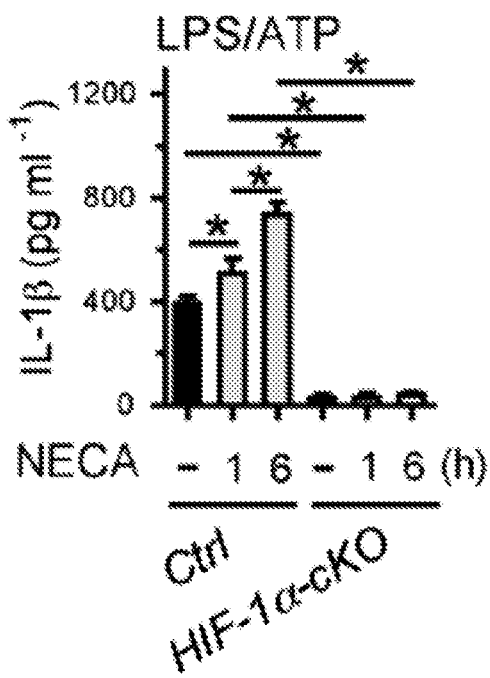
Figure 4H:
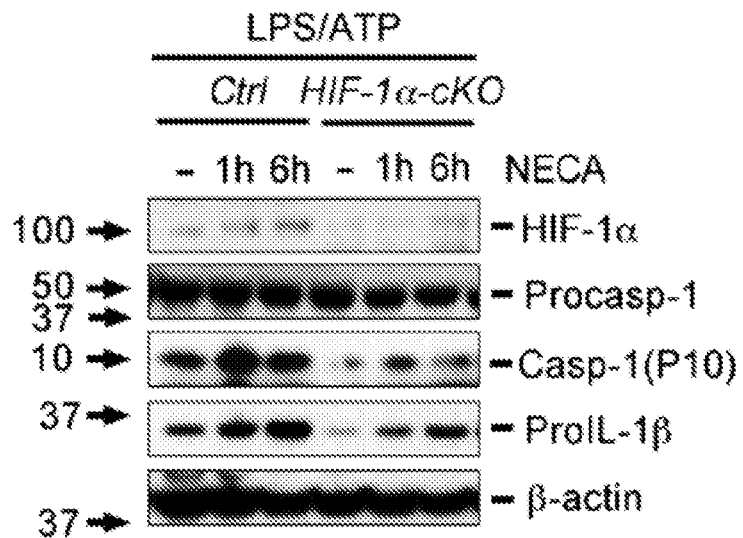

A direct link between PKA activation and HIF-1α upregulation is provided by cAMP response element-binding protein (CREB) which enhances two C-terminus trans activating domains in HIF-1α. The requirement for CREB in adenosine induced up-regulation of HIF-1α was tested by transfection of THP-1 human monocyte cell line with the HRE promoter luciferase construct and β-galactosidase plasmid in the presence or absence of CREB dominant negative plasmid (CREBΔ) for 24 hours, and then primed with LPS/PMA for 16 hours followed by NECA treatment over 8 hours. An adenosine stimulus resulted in HRE reporter luciferase activity, and this was inhibited by the presence of the dominant negative CREB plasmid (FIG. 4D). In an analogous manner transfection of the IL-1β promoter luciferase construct and β-galactosidase plasmid in the presence or absence of CREB dominant negative form demonstrated a requirement for CREB signaling for the production of IL-1β (FIG. 4E). Transcriptional up-regulation of Pro-IL-1β on initial LPS stimulation is via activation of the NF-kB pathway. Upon testing whether the subsequent transcriptional up-regulation of Pro-IL-1β also uses this pathway, adenosine agonists were found not to increase activity of the NF-kB pathway above that already induced by LPS (FIG. 4F). In the absence of HIF-1α, there was a significant reduction at the protein level in pro-caspase-1, activated caspase-1, pro-IL-1β, and ultimately active IL-1β (FIGS. 4G-4H). These data show that adenosine induced up-regulation of IL-1β is dependent on a CREB/HIF-1α pathway, which is distinct from the NF-kB pathway used for initial production of IL-1β in response to LPS.

Example 5: Liver Injury is Dependent on A+ Receptor in Macrophages

Figure 5A:
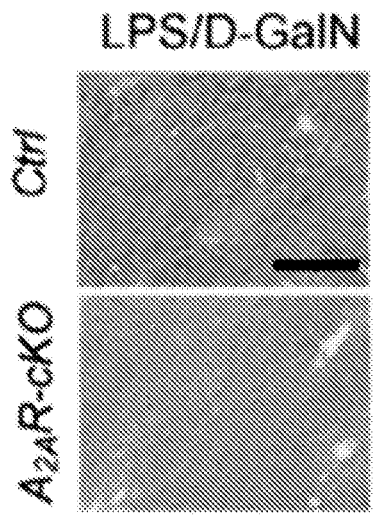
FIGS. 5A-5H illustrate the finding that liver injury and fibrosis is dependent on $A_{2A}$ receptor signaling in macrophages.
Figure 5B:
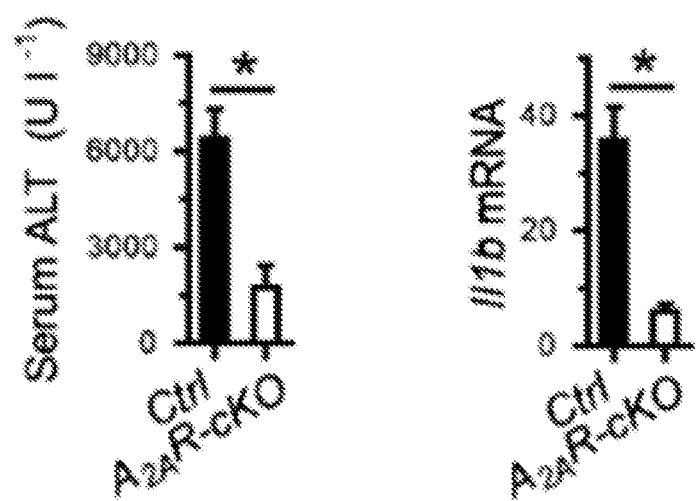
Figure 5C:
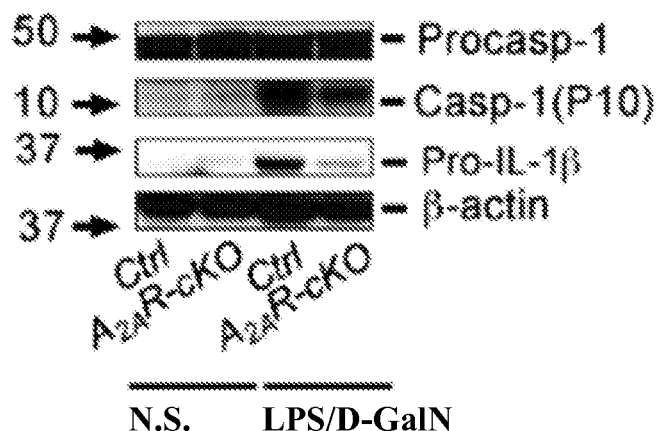
Figure 5D:
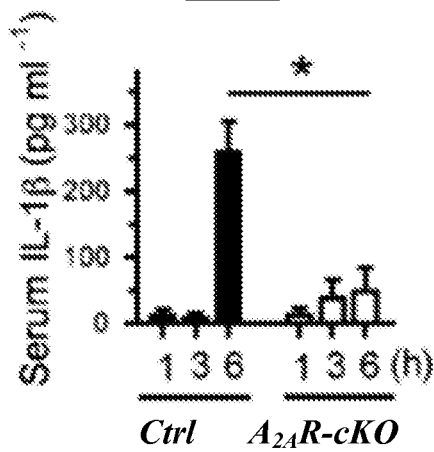
Figure 5E:
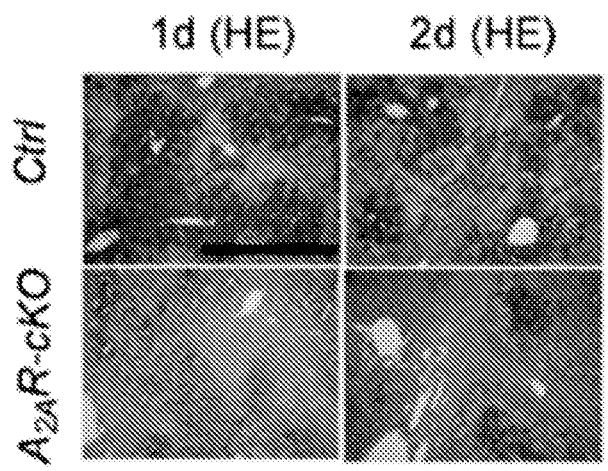
Figure 5F:
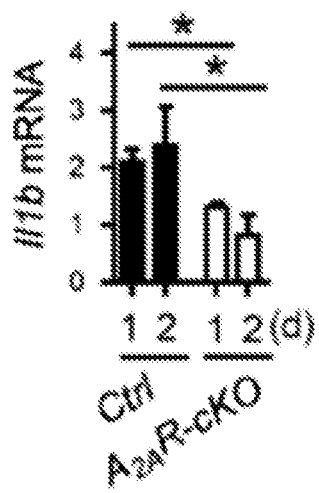
Figure 13:
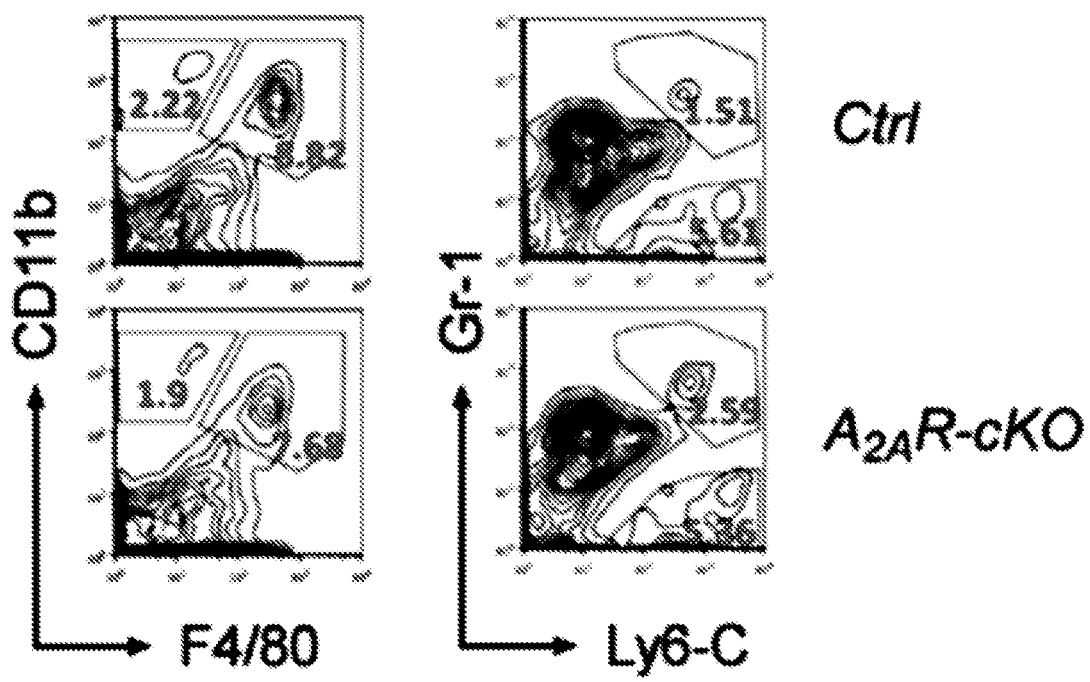
FIG. 13 is a set of images illustrating normal distribution of major hepatic cellular populations in $A_{3A}$R-cKO mice. Liver tissues were collected from $A_{2A}$R-cKO and control mice, and then the liver mononuclear cells were isolated. The frequencies of CD11b+, CD11b+/F4/80+, Gr1+/Ly6-C+ and Ly6-C+ subsets were determined by FACS.
Figure 14A:
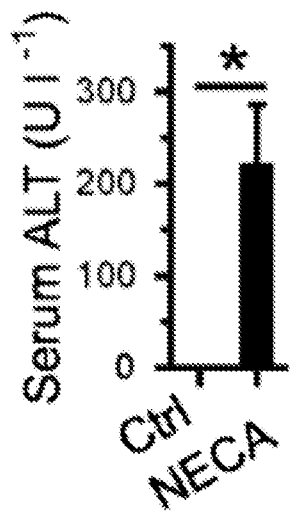
FIGS. 14A-14F illustrate increase in serum ALT and changes in liver gene expression in mice treated with LPS in the presence or absence of adenosine agonist. Wild type C57BL/6 mice were injected intraperitoneally with LPS (1 μg/mouse). 16 hours later mice received NECA (2.5 mg kg$^{-1}$ body weight) and D-galactosamine (500 mg kg$^{-1}$) by IP for 2 hours following liver tissue and serum collection. Serum ALT was determined (FIG. 14A), and the gene expression of Il1β (FIG. 14B), Il6 (FIG. 14C), Hif1α (FIG. 14D), Nlrp3 (FIG. 14E), and tnfα (FIG. 14F) was quantified by real-time PCR using each specific gene primer set as listed. Data are expressed as the mean±SD from 6 mice in each treatment group. *p<0.05 determined by Student's t-test.
Figure 14B:
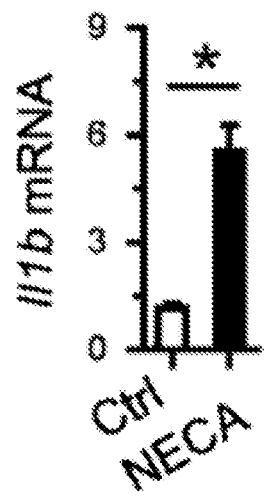
Figure 14C:
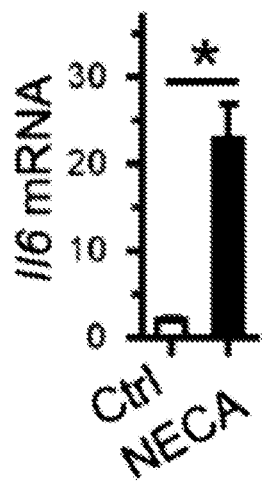
Figure 14D:
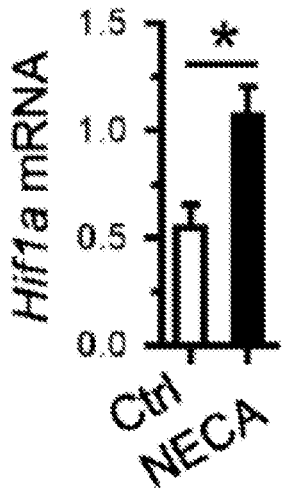
Figure 14E:
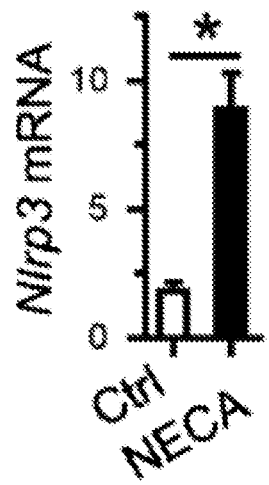
Figure 14F:
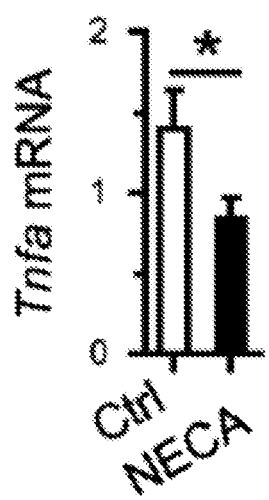

The results recited herein show a requirement for adenosine signaling via the $A_{2A}$ receptor for maximal production of IL-1β by macrophages in vitro. With tissue inflammation and injury extracellular adenosine levels are known to increase by a variety of means from the basal levels below 1 µM to levels up to 100 mM. It was tested whether $A_{2A}$ receptor driven inflammasome activity was relevant in vivo; two models of liver injury was used: one acute LPS driven model where liver injury was assessed in 6 hours after LPS, and a second model of sterile injury by a toxic metabolic insult to the liver by thioacetamide (TAA) in which injury was examined at days 1, 2 and 7. $A_{2A}$R-cKO mice that specifically delete Adora2a gene in macrophages were used. Liver immune populations were intact in these mice (FIG. 13). Six hours after LPS and D-galactosamine induced liver injury, there was significantly less hemorrhage and necrosis in the livers from $A_{2A}$R-cKO mice and this was confirmed by lower serum ALT values (FIG. 5A). Reduced activation of the inflammasome was confirmed by demonstrating that whole liver had lower levels of Il1b mRNA, less active caspase-1, and that there were lower levels of serum IL-1β (FIGS. 5B, 5C-5D). To test the effect of increasing adenosine signaling in vivo, wild-type mice were treated with LPS in the presence or absence of the adenosine agonist NECA. The presence of NECA resulted in a significant elevation in serum ALT, whole liver transcripts of Il1b, Il6, Hif1a and Nlrp3, and a reduction in the transcript for tnfa (FIGS. 14A-14F).

Figure 5G:
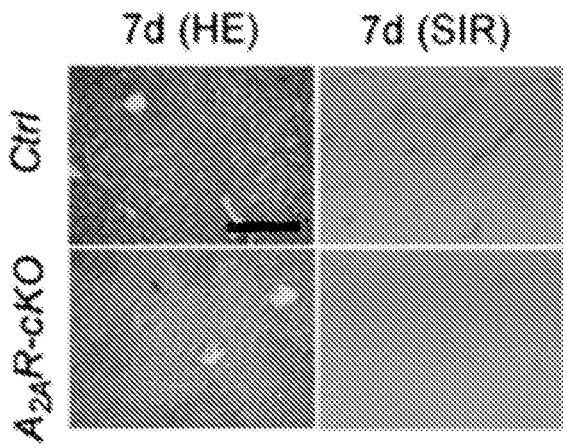
Figure 5H:
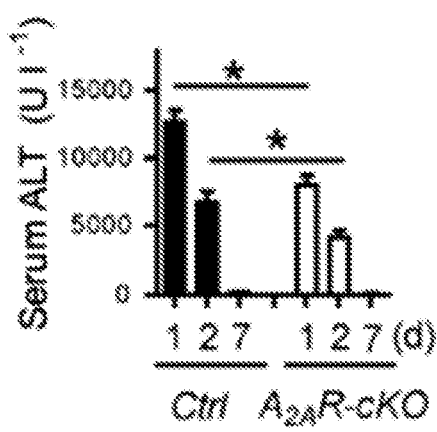
Figure 15A:
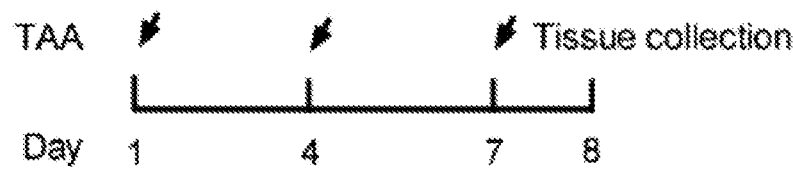
FIGS. 15A-15C illustrate sustained IL1β production by repeated TAA injection in A$_{2A}$R-cKO mice.
Figure 15B:
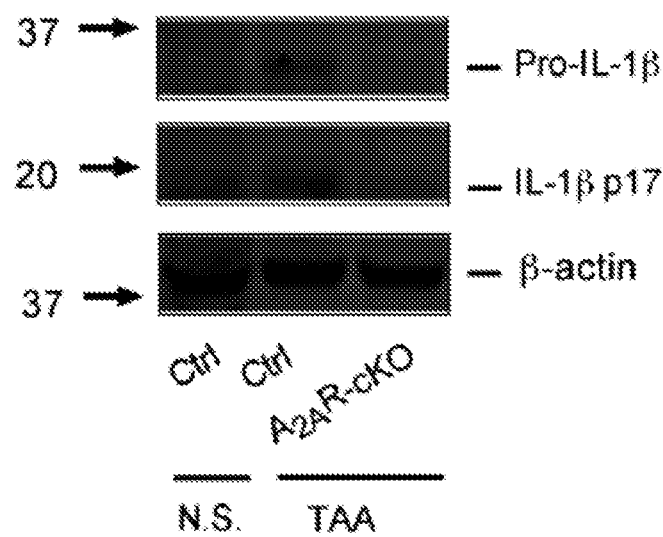
Figure 15C:
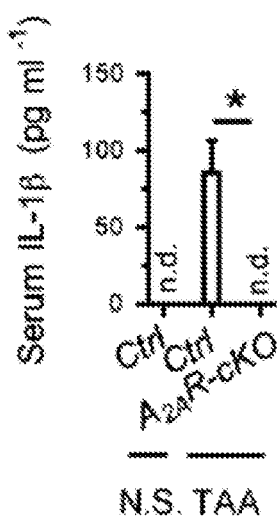

Toxic injury by TAA demonstrated maximal hemorrhage and necrosis at day 1. There was less liver hemorrhage and necrosis, and lower levels of liver Il1b mRNA and serum ALT in $A_{2A}$R-cKO mice (FIGS. 5E-5H). In addition to inflammation, inflammasome activity is required for the development of the fibrotic response in many organs. To assess if fibrosis was also affected in the absence of $A_{2A}$ receptor on tissue macrophages, liver tissues from 7 days after TAA were stained for collagen by Sirius Red. There was significantly less fibrosis in livers from $A_{2A}$R-cKO mice compared to wild-type (FIG. 5G). A sustained IL-1β production was also seen in liver tissue and serum after a course of repeated TAA injection in wild-type control, but not $A_{2A}$R-cKO mice (FIGS. 15A-15C).

Figure 16A:
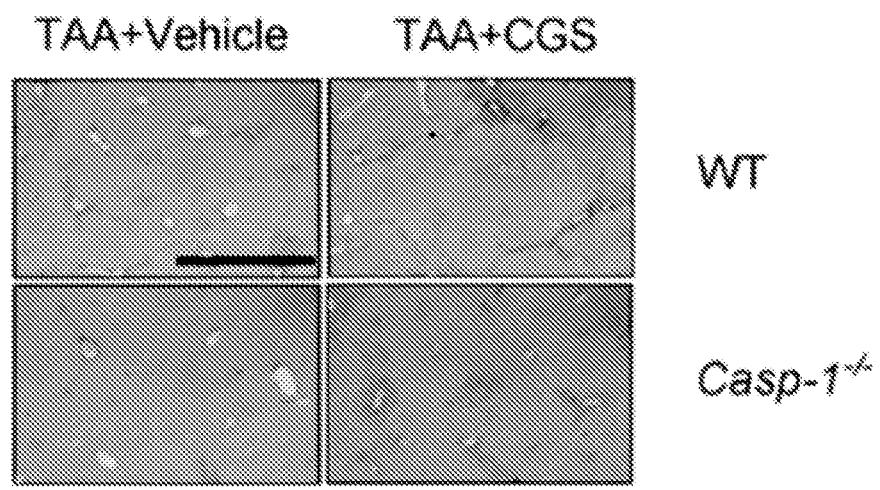
FIGS. 16A-16B illustrate increased liver fibrosis in wild-type control but not caspase-1-deficient mice in response to adenosine agonist.
Figure 16B:
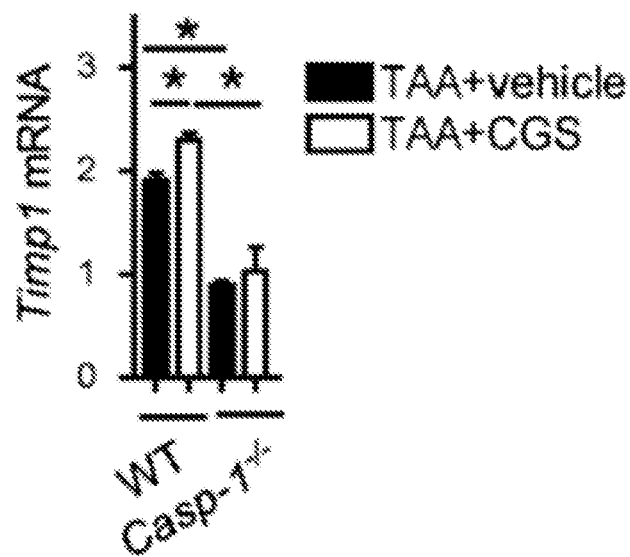

To further test the effect of increased adenosine signaling on fibrosis wild-type and caspase-1 deficient mice were injected with TAA with and without co-injection of the adenosine agonist CGS21680. After one week, liver tissues were stained for collagen with Sirus Red. CGS21680 increased TAA induced liver fibrosis and Timp1 expression in wildtype but not caspase-1 deficient mice (FIGS. 16A-16B). Collectively these data confirm that adenosine induced signaling via the $A_{2A}$ receptor is important for in vivo activation of the inflammasome in acute and chronic injury.

Example 6

The current model of inflammasome activation in macrophages is inadequate to explain how activity is sustained in chronic inflammation, repair and fibrosis. The issue is not only the self-limited inflammatory response induced by signals 1 and 2, but also the unresponsiveness of macrophages to similar subsequent signals. As macrophages are unresponsive to repeat exposure to the initiating signals, it was investigated whether further signals are qualitatively different, with signals from tissue injury being attractive candidates. Adenosine regulates tissue responses to stress and injury via activation of four widely distributed receptors. Adenosine levels rapidly increase in the extracellular environment in response to cell stress and death by release from cytosolic stores and sequential dephosporylation from ATP, and are rapidly reduced by uptake and metabolism. Manipulations that increase adenosine signaling result in increased release of IL-1β from conventionally activated PEC, and this is not due to enhancement of an IL-1 mediated positive feedback loop (FIGS. 1A-1E). Adenosine has a role concurrent with, or after conventional inflammasome activation. The in vivo implications are that during and after inflammasome activation the ambient adenosine concentration regulates the duration of inflammasome activation, and can restimulate it. The data presented herein are consistent with the original in vivo data from $A_{2A}$ receptor deficient mice, showing a lack of rise in serum IL-1β in response to LPS10.

The contribution of $A_{2A}$ receptor activation is to upregulate the transcript levels of Pro-IL-1β, NLRP3 and others. This means that an adenosine stimulus can up-regulate both arms of signal 1 and 2 pathways, as demonstrated by greater levels of pro-IL-1β protein and active caspase-1 (FIGS. 3E, 3I). Furthermore this is a broad response with adenosine increasing inflammasome activation in response to a range of TLR stimuli for signal 1, as well as ATP, monosodium urate and synthetic bead induced activation of signal 2 (FIGS. 7A-7H).

Initial activation of PEC by LPS results in high levels of Pro-IL1β, and subsequent exposure to LPS cannot stimulate a repeated elevation (LPS tolerance). As demonstrated herein, after initial activation PEC up-regulates Pro-IL-1β and produces IL-1β in response to adenosine signals without further exposure to conventional signals 1 and 2. These PEC are clearly not unresponsive in a global way, rather after initial activation by LPS and ATP they have switched their phenotype into a state in which Pro-IL1β production is regulated by adenosine signals (FIG. 3A). Without wishing to be limited by any theory, this is better characterized as a post-activation, rather than an unresponsive state. The effect of adenosine is however not uniform for all cytokines. In particular, adenosine results in downregulation of TNF-α production, and does not alter the genes for most antimicrobial proteins (FIGS. 10A-10F).

The initial steps downstream of the $A_{2A}$ receptor that are required for the increased IL-1β production are the signaling molecules cAMP, and PKA (FIGS. 3B-3F). Detailed investigation using HIF-1α inhibitors, reporter constructs and macrophage specific knockouts demonstrates that the ability of adenosine signals to upregulate pro-IL-1β is dependent on HIF-1α and CREB, with CREB being proximal to HIF-1α

(FIGS. 4B-4C). This is distinct from the NF-kB pathway utilized for pro-cytokine upregulation after initial TLR activation which is not reduced by adenosine signaling.

Without wishing to be limited by any theory, in the absence of $A_{2A}$ receptor signaling on macrophages, there is reduced inflammasome activation, with less tissue injury and fibrosis. This was the case in an acute and sustained model of LPS and TAA induced liver injury (FIG. 5). This provides valuable confirmation of the scale of the adenosine signal in vivo. In a number of experimental models, total $A_{2A}$ receptor deficient animals have greater organ injury. Without wishing to be limited by any theory, adenosine can be simultaneously functioning to enhance macrophage based inflammatory responses, and providing parenchymal cell protection—with both being part of an integrated response to tissue injury by pathogens and sterile insults.

The data disclosed herein demonstrate that macrophages after receiving conventional signals 1 and 2, are dependent on adenosine via the $A_{2A}$ receptor for initial and sustained inflammasome activity and IL-1β production.

Example 7: Low-Dose Cardiac Glycosides Protect from NASH and Alcoholic Hepatitis in Mice The inflammasome plays a crucial role in the pathogenesis of NASH and alcoholic hepatitis, and HIF-1α is required for sustained inflammasome activity. Digoxin was identified with potent HIF1α antagonist but its role in liver disease is unexamined. The present study was performed to assess whether a low dose of digoxin has therapeutic effects in NASH and alcoholic hepatitis in mice, and investigate the molecular mechanisms of the activity of digoxin.

C57BL/6J male mice were placed on a 45% high-fat diet (HFD) for 11 weeks with and without digoxin (ip 1 mg/kg twice a week). Digoxin, 1 mg/kg ip daily, in mice results in the therapeutic serum levels achieved in humans (0.5-2 ng/ml). Plasma ALT, liver histology, neutrophil staining, leukocytes profiling, mitochondrial reactive oxygen species (ROS) generation, and gene transcriptome microarrays were analyzed. The ability of digoxin to inhibit inflammasome in mouse and human macrophages was tested. The chronic plus binge model of alcoholic hepatitis and LPS/D-GalN hepatitis models were also performed.

In all three models digoxin resulted in reduced histological injury, neutrophilic infiltrate and lower serum ALT's (417±398 U/L in HFD vs 91±73 U/L in HFD+DIG, P<0.001). Starting digoxin after 4 weeks HFD still showed significant reduction in liver inflammation (neutrophil 24.6% in HFD vs 14.3% in HFD+DIG; monocytes 31.6% in HFD vs 19.1% in HFD+DIG) without a reduction in food intake. In LPS/DGalN hepatitis, a dose titration of twice, a quarter and a twentieth of the human equivalent dose resulted in improvement of liver hemorrhage and necrosis, reduction in liver HIF-1α and Pro-IL-1β transcripts as well as the proteins of IL-1β, HIF-1α, pro-IL-1β and cleaved (P10) caspase-1. Microarray analysis in HFD liver revealed significant changes of signal genes that digoxin downregulated ROS metabolism, antioxidant pathway and glycolysis.

In vitro data showed that digoxin dose-dependently inhibited mitochondrial ROS production under TLR and hydrogen peroxide stimulation in mouse and human macrophages. Digoxin also inhibited IL-1 β secretion and caspase-1 activation in mouse macrophages.

As demonstrated herein, low doses of digoxin reduce liver steatosis, and inflammation in experimental models of NASH and alcoholic hepatitis via a ROS-HIF1α-inflammasome pathway. Low dose digoxin thus has significant utility in the treatment of NASH and alcoholic hepatitis.

Example 8: Clinical Studies

Study

A randomized double blinded placebo controlled clinical trial is performed to evaluate the use of cardiac glycosides (such as digoxin) in the treatment of NASH.

The study comprises 25 patients in each arm, wherein each patient receives 48 weeks of digoxin (75 mcg/day) or placebo. Liver biopsies are performed at the start and end of the study. Entry criteria for the study subjects comprises BMI of 30-45 and histology proven NASH.

The primary end-point of the study comprises histological improvement in NASH. The secondary end points comprise radiological improvement in NASH, weight loss, and/or reduction in serum cholesterol.

Study

A randomized double blinded placebo controlled clinical trial is performed to evaluate the use of cardiac glycosides (such as digoxin) in the treatment of alcoholic hepatitis.

The study comprises 25 patients in each arm, wherein each patient receives 48 weeks of digoxin (75 μg/day) or placebo. Liver biopsies are performed at the start and end of the study. Entry criteria for the study subjects comprises BMI of 25-30 and alcoholic hepatitis on standard clinical criteria.

The primary end-point of the study comprises histological improvement in discriminant function.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed:

1. A method of treating a mammal afflicted with a liver disease or disorder, wherein the liver disease or disorder is selected from the group consisting of non-alcoholic steatohepatitis (NASH), liver injury associated with or caused by alcohol consumption in a mammal afflicted with NASH, alcoholic hepatitis, drug induced liver injury, primary sclerosing cholangitis, viral hepatitis, liver fibrosis, liver cirrhosis, and other toxic liver conditions, wherein the method comprises
administering to the mammal a therapeutically effective amount of at least one cardiac glycoside; and
inducing at least a 50% reduction in serum alanine transaminase (ALT) levels after administering the at least one cardiac glycoside compared with ALT levels in the serum before administration of the at least one cardiac glycoside; and
wherein administration of the at least one cardiac glycoside to the mammal affords a cardiac glycoside plasma level in the mammal that is equal to or lower than the cardiac glycoside plasma level required to treat a cardiac disease in mammals afflicted with the cardiac disease.

2. The method of claim 1, wherein administration of the at least one cardiac glycoside to the mammal does not cause a clinically significant cardiac effect in the mammal.

3. The method of claim 2, wherein the clinically significant cardiac effect is selected from the group consisting of occurrence of atrial tachycardia, occurrence of atrioventricular block, reduction in atrioventricular node conduction, increase in effective refractory period within the atrioventricular node, and any combination thereof.

4. The method of claim 1, wherein the cardiac glycoside inhibits at least one condition selected from the group consisting of HIF-1α synthesis in the liver of the mammal, inflammation in the liver of the mammal, and liver steatosis in the mammal.

5. The method of claim 1, wherein the cardiac glycoside reduces in the mammal at least one condition selected from the group consisting of liver damage, fat-induced obesity and glycolysis.

6. The method of claim 1, wherein the at least one cardiac glycoside is selected from the group consisting of acetyldigitoxin, bufalin, cinobufagerin, convallatoxin, cymarin, digitoxigenin, digotoxin, digoxigerin, digoxin, gitoxigenin, gitoxin, marinobufagenin, nerifolin, oleandrin, ouabain, periplocymarin, peruvoside, proscillaridin A, strophanthin K, UNBS1450, and any combination thereof.

7. The method of claim 1, wherein the at least one cardiac glycoside comprises digoxin.

8. The method of claim 1, wherein the at least one cardiac glycoside comprises digoxin, and administration of the at least one cardiac glycoside to the mammal affords a digoxin plasma level that is equal to or lower than about 0.8 ng/ml.

9. The method of claim 1, wherein the at least one cardiac glycoside comprises digoxin, and administration of the at least one cardiac glycoside to the mammal affords a digoxin plasma level selected from the group consisting of: about 0.02 to about 0.05 ng/ml; about 0.05 to about 0.1 ng/ml; about 0.05 to about 0.15 ng/ml; about 0.05 to about 0.2 ng/ml; about 0.05 to about 0.25 ng/ml; about 0.05 to about 0.3 ng/ml; about 0.05 to about 0.35 ng/ml; about 0.05 to about 0.4 ng/ml; about 0.05 to about 0.45 ng/ml; about 0.05 to about 0.5 ng/ml; about 0.05 to about 0.55 ng/ml; about 0.05 to about 0.6 ng/ml; about 0.05 to about 0.65 ng/ml; about 0.05 to about 0.7 ng/ml; about 0.05 to about 0.75 ng/ml; and about 0.05 to about 0.8 ng/ml.

10. The method of claim 1, wherein the at least one cardiac glycoside is administered to the mammal about once a day, about every other day, about every third day, about every fourth day, about every fifth day, about every sixth day, or about once a week.

11. The method of claim 1, wherein the mammal is further administered at least one additional agent that reduces the symptoms of or treats the liver disease or disorder.

12. A method of treating a mammal afflicted with a liver disease or disorder, the method comprising: administering to the mammal a therapeutically effective amount of a composition consisting of at least one cardiac glycoside and at least one pharmaceutically acceptable carrier; and wherein the liver disease or disorder is selected from the group consisting of non-alcoholic steatohepatitis (NASH), liver injury associated with or caused by alcohol consumption in a mammal afflicted with NASH, alcoholic hepatitis, drug induced liver injury, primary sclerosing cholangitis, viral hepatitis, liver fibrosis, liver cirrhosis, and other toxic liver conditions, and wherein administration of the composition to the mammal affords a cardiac glycoside plasma level in the mammal that is equal to or lower than the cardiac glycoside plasma level required to treat a cardiac disease in mammals afflicted with the cardiac disease.

* * * * *